US012065503B2

(12) United States Patent
Suemitsu et al.

(10) Patent No.: US 12,065,503 B2
(45) Date of Patent: Aug. 20, 2024

(54) PHARMACEUTICAL COMPOSITION CONTAINING TAGGED SITE-ANTIHUMAN ANTIBODY FAB FRAGMENT COMPLEX

(71) Applicant: ASTELLAS PHARMA INC., Tokyo (JP)

(72) Inventors: Jumpei Suemitsu, Tokyo (JP); Megumi Ikeda, Tokyo (JP); Moe Kohno, Tokyo (JP)

(73) Assignee: ASTELLAS PHARMA INC., Tokyo (JP)

( * ) Notice: Subject to any disclaimer, the term of this patent is extended or adjusted under 35 U.S.C. 154(b) by 462 days.

(21) Appl. No.: 17/283,988

(22) PCT Filed: Oct. 9, 2019

(86) PCT No.: PCT/JP2019/039793
§ 371 (c)(1),
(2) Date: Apr. 9, 2021

(87) PCT Pub. No.: WO2020/075746
PCT Pub. Date: Apr. 16, 2020

(65) Prior Publication Data
US 2021/0355233 A1   Nov. 18, 2021

(30) Foreign Application Priority Data
Oct. 10, 2018 (JP) ................. 2018-191605

(51) Int. Cl.
C07K 16/30 (2006.01)
A61K 47/10 (2017.01)
A61K 47/26 (2006.01)
A61K 51/04 (2006.01)
A61K 51/10 (2006.01)

(52) U.S. Cl.
CPC .......... *C07K 16/3007* (2013.01); *A61K 47/10* (2013.01); *A61K 47/26* (2013.01); *A61K 51/0446* (2013.01); *A61K 51/1051* (2013.01); *A61K 51/1093* (2013.01); *C07K 16/3092* (2013.01); *C07K 2317/55* (2013.01); *C07K 2317/71* (2013.01)

(58) Field of Classification Search
CPC ............ C07K 16/3007; C07K 16/3092; C07K 2317/55; C07K 2317/71; C07K 16/2803; C07K 2317/94; A61K 47/10; A61K 47/26; A61K 51/0446; A61K 51/1051; A61K 51/1093; A61K 39/39591; A61K 47/6851; A61K 47/6853; A61K 47/6803; A61K 9/08; A61K 9/19; A61K 47/02; A61K 47/12; A61K 47/18; A61K 47/20; A61K 47/22; A61K 51/1048; A61K 2039/505; A61K 2039/507; A61P 35/00
See application file for complete search history.

(56) References Cited

U.S. PATENT DOCUMENTS

| | | |
|---|---|---|
| 8,623,367 B2 | 1/2014 | Momm et al. |
| 2002/0146750 A1 | 10/2002 | Hoogenboom et al. |
| 2005/0118167 A1 | 6/2005 | Okada et al. |
| 2005/0244333 A1 | 11/2005 | Yazaki et al. |
| 2008/0069816 A1 | 3/2008 | Yazaki et al. |
| 2009/0081213 A1 | 3/2009 | Chevrier et al. |
| 2010/0034825 A1 | 2/2010 | Clausen et al. |
| 2010/0111856 A1 | 5/2010 | Gill et al. |
| 2011/0236398 A1 | 9/2011 | Momm et al. |
| 2012/0040375 A1 | 2/2012 | Nishimura et al. |
| 2012/0128676 A1 | 5/2012 | Danielczyk et al. |
| 2012/0219503 A1 | 8/2012 | Kumar et al. |
| 2012/0251529 A1 | 10/2012 | Hofer et al. |
| 2012/0294859 A1 | 11/2012 | Goletz et al. |
| 2012/0328514 A1 | 12/2012 | Cesati et al. |
| 2013/0045543 A1 | 2/2013 | Nishimura et al. |
| 2013/0123471 A1 | 5/2013 | Yang et al. |
| 2014/0212408 A1 | 7/2014 | Hofer et al. |

(Continued)

FOREIGN PATENT DOCUMENTS

| | | |
|---|---|---|
| CA | 3115747 A1 | 4/2020 |
| CN | 102482701 B | 5/2015 |

(Continued)

OTHER PUBLICATIONS

Wang W et al. "Antibody Structure, Instability, and Formulation", Journal of Pharmaceutical Sciences, 2007, 96(1) 1-26, DOI: 10.1002/JPS.207270 (Year: 2007).*
Perk LR et al. P-Isothiocyanatobenzyl-desferrioxamine: a new bifunctional chelate for facile radiolabeling of monoclonal antibodies with zirconium-89 for immuno-PET imaging. (Eur J Nucl Med Mol Imaging 2010 37, 250-259). (Year: 2010).*
Vagenende V et al. Mechanisms of Protein Stabilization and Prevention of Protein Aggregation by Glycerol (Biochemistry 2009, 48, 46, 11084-11096) (Year: 2009).*
Bhatt NB et al. A comprehensively revised strategy that improves the specific activity and long-term stability of clinically relevant 89Zr-immuno-PET agents. Dalton Trans. Oct. 7, 2018; 47(37): 13214-13221 (Year: 2018).*

(Continued)

*Primary Examiner* — Julie Wu
*Assistant Examiner* — John J Skoko, III
(74) *Attorney, Agent, or Firm* — MARSHALL, GERSTEIN & BORUN LLP

(57) ABSTRACT

Provided is a stable pharmaceutical composition comprising a labeling moiety-anti-human antibody Fab fragment conjugate, and the like. In the pharmaceutical composition comprising a labeling moiety-anti-human antibody Fab fragment conjugate, citric acid, phosphoric acid, 2-[4-(2-hydroxyethyl)-1-piperazinyl]ethanesulfonic acid or trishydroxymethyl aminomethane is added as a buffering agent, sucrose or glycerin is added as a stabilizer, a nonionic surfactant is added, and the pH is adjusted to 6.5 to 7.5. This enables suppression of generation of multimers and insoluble subvisible particles during preservation of the labeling moiety-anti-human antibody Fab fragment conjugate.

14 Claims, No Drawings

Specification includes a Sequence Listing.

(56) References Cited

U.S. PATENT DOCUMENTS

| | | |
|---|---|---|
| 2015/0005474 A1 | 1/2015 | Goletz et al. |
| 2015/0056134 A1 | 2/2015 | Sawada et al. |
| 2015/0078997 A1 | 3/2015 | Cesati et al. |
| 2016/0011217 A1 | 1/2016 | Matsumura et al. |
| 2016/0108131 A1 | 4/2016 | Berne et al. |
| 2016/0229923 A1 | 8/2016 | Hofer et al. |
| 2017/0198056 A1 | 7/2017 | Nishimura et al. |
| 2018/0022817 A1 | 1/2018 | Berne et al. |
| 2018/0079827 A1 | 3/2018 | Hofer et al. |
| 2018/0221512 A1 | 8/2018 | Yazaki et al. |
| 2019/0091353 A1 | 3/2019 | Arano et al. |
| 2019/0185583 A1 | 6/2019 | Hofer et al. |
| 2019/0269804 A1 | 9/2019 | Morinaka et al. |
| 2020/0102401 A1 | 4/2020 | Berne et al. |
| 2020/0123270 A1 | 4/2020 | Doihara et al. |
| 2020/0268913 A1 | 8/2020 | Arano et al. |

FOREIGN PATENT DOCUMENTS

| | | | |
|---|---|---|---|
| CN | 109952375 A | | 6/2019 |
| EP | 2083868 A2 | | 8/2009 |
| EP | 2347769 A1 | | 7/2011 |
| EP | 2351777 A1 | | 8/2011 |
| EP | 2480665 A1 | | 8/2012 |
| EP | 2565268 A1 | | 3/2013 |
| EP | 2567982 A1 | | 3/2013 |
| EP | 3256494 A1 | | 12/2017 |
| EP | 3543337 A1 | | 9/2019 |
| EP | 3795590 A1 | | 3/2021 |
| EP | 3865154 A1 | | 8/2021 |
| EP | 3909606 A1 | | 11/2021 |
| EP | 3909608 A1 | | 11/2021 |
| JP | 2010-505775 A | | 2/2010 |
| JP | 2012-511540 A | | 5/2012 |
| JP | 2012-532868 A | | 12/2012 |
| JP | 2013-500703 A | | 1/2013 |
| JP | 2013-505702 A | | 2/2013 |
| JP | 2013-510093 A | | 3/2013 |
| JP | 2013-517487 A | | 5/2013 |
| JP | 2016-506370 A | | 3/2016 |
| JP | 2016520075 | * | 7/2016 ........... A61K 39/395 |
| JP | 2016-534735 A | | 11/2016 |
| KR | 10-2019-0078573 A | | 7/2019 |
| TW | 201920273 A | | 6/2019 |
| WO | 00/66160 A1 | | 11/2000 |
| WO | 01/75110 A2 | | 10/2001 |
| WO | 2005/086875 A2 | | 9/2005 |
| WO | 2007/019232 A2 | | 2/2007 |
| WO | 2008/040362 A2 | | 4/2008 |
| WO | 2010/050528 A1 | | 5/2010 |
| WO | 2010/066762 A1 | | 6/2010 |
| WO | 2011/005322 A2 | | 1/2011 |
| WO | 2011/012309 A1 | | 2/2011 |
| WO | 2011/034660 A1 | | 3/2011 |
| WO | 2011/037271 A1 | | 3/2011 |
| WO | 2011/056983 A1 | | 5/2011 |
| WO | 2011/089004 A1 | | 7/2011 |
| WO | 2011/135869 A1 | | 11/2011 |
| WO | 2012/015912 A1 | | 2/2012 |
| WO | 2012/117002 A1 | | 9/2012 |
| WO | 2013/081091 A1 | | 6/2013 |
| WO | 2014/079886 A1 | | 5/2014 |
| WO | 2014/133093 A1 | | 9/2014 |
| WO | 2014/177568 A1 | | 11/2014 |
| WO | 2015/053871 A2 | | 4/2015 |
| WO | 2015/094900 A1 | | 6/2015 |
| WO | 2015/157286 A1 | | 10/2015 |
| WO | 2015/166934 A1 | | 11/2015 |
| WO | 2016/073915 A1 | | 5/2016 |
| WO | 2016/130726 A1 | | 8/2016 |
| WO | WO-2017129585 A1 | * | 8/2017 ......... A61K 39/3955 |
| WO | 2017/150549 A1 | | 9/2017 |
| WO | 2018/092885 A1 | | 5/2018 |
| WO | 2019/009388 A1 | | 1/2019 |
| WO | 2019/065774 A1 | | 4/2019 |
| WO | 2019/221269 A1 | | 11/2019 |
| WO | 2020/075746 A1 | | 4/2020 |
| WO | 2020/145227 A1 | | 7/2020 |
| WO | 2020/145228 A1 | | 7/2020 |

OTHER PUBLICATIONS

Summer D et al. Cyclic versus Noncyclic Chelating Scaffold for 89Zr-Labeled ZEGFR:2377 Affibody Bioconjugates Targeting Epidermal Growth Factor Receptor Overexpression. (Mol Pharm. 2018 15(1): 175-185. (Year: 2018).*

Van Brummelen et al., 89Zr-labeled CEA-targeted IL-2 variant immunocytokine in patients with solid tumors: CEA-mediated tumor accumulation and role of IL-2 receptor-binding, Oncotarget., 9(37):24737-24749 (2018).

Singapore Office Action issued on Oct. 17, 2022; Singapore Application No. 11202103670X.

Shire, Formulation of proteins and monoclonal antibodies mAbs, Monoclonal Antibodies: Meeting the Challenges in Manufacturing, Formulation, Delivery and Stability of Final Drug Product, 93-120: (2015).

Supplementary European Search Report and Opinion, European Application No. 19870506.3, mailed Oct. 7, 2022.

Zhu et al., Formulation and protein- and peptide-based parenteral products, In: Parental Medications Third Edition, 222-253: (2010).

Akizawa et al., Renal brush border enzyme-cleavable linkages for low renal radioactivity levels of radiolabeled antibody fragments, Bioconjugate Chem., 24(2):291-299 (2013).

Araki et al., Examination of renal brush border membrane enzyme recognition of Illin-DOTA derivative binding peptide for reduction of renal accumulation of RI-labeled antibody fragment, Abstract of the Annual Meeting of the Pharmaceutical Society of Japan, 138:27PA-am401 (2018).

Arano et al., Chemical design of radiolabeled antibody fragments for low renal radioactivity levels, Cancer Research, 59(1):128-134 (1999).

Chevallier et al., BCR-ABL1 molecular remission after 90Y-epratuzumab tetraxetan radioimmunotherapy in CD22+ Ph+ B-ALL: proof of principle, European Journal of Hematology, 91(6):552-556 (2013).

Giannini et al., Synthesis and preliminary in vitro evaluation of DOTA-Tenatumomab conjugates for theranostic applications in tenascin expressing tumors, Bioorganic Med. Chem., 27(15):3248-3253 (2019).

International Application No. PCT/JP19/039793, International Preliminary Report on Patentability received for mailed on Apr. 22, 2021.

International Application No. PCT/JP2017/041486, International Preliminary Report on Patentability, mailed May 31, 2019.

International Application No. PCT/JP2017/041486, International Search Report and Written Opinion, mailed Feb. 13, 2018.

International Application No. PCT/JP2019/019663, International Preliminary Report on Patentability, mailed Nov. 26, 2020.

International Application No. PCT/JP2019/019663, International Search Report and Written Opinion, mailed Aug. 13, 2019.

International Application No. PCT/JP2020/000036, International Search Report and Written Opinion, mailed Mar. 24, 2020.

International Application No. PCT/JP2020/000037, International Search Report and Written Opinion, mailed Apr. 7, 2020.

Li et al., Reduction of kidney uptake in radiometal labeled peptide linkers conjugated to recombinant antibody fragments. Site-specific conjugation of DOTA-peptides to a Cys-diabody, Bioconjugate Chem., 13(5):985-995 (2002).

Russian Office Action Patent Application No. 2019118653 issued on Aug. 20, 2021.

Study to Evaluate the Safety and Preliminary Efficacy of 177Lu-OPS201 in NETs, ClinicalTrials.gov Identifier_NCT02592707 (2015).

Tsai et al., Metabolism and renal clearance of 111In-labeled DOTA-conjugated antibody fragments, Bioconjugate Chem., 12(2):264-270 (2001).

Uehara et al., (67/68)Ga-labeling agent that liberates (67/68)Ga-NOTA-methionine by lysosomal proteolysis of parental low molecu-

(56) References Cited

OTHER PUBLICATIONS lar weight polypeptides to reduce renal radioactivity levels, Bioconjugate Chem., 25(11):2038-2045 (2014).
Uehara et al., A Gallium-67/68-Labeled Antibody Fragment for Immuno-SPECT/PET Shows Low Renal Radioactivity Without Loss of Tumor Uptake, Clin. Cancer Res., 24(14):3309-3316 (2018).
Uehara et al., Design, synthesis, and evaluation of [188Re]organorhenium-labeled antibody fragments with renal enzyme-cleavable linkage for low renal radioactivity levels, Bioconjugate Chem., 18(1):190-198 (2007).
Wu et al., Biodistribution and catabolismof Ga-67-labeled anti-Tac dsFv fragment, Bioconjugate Chem., 8(3):365-369 (1997).
Yarilin, Fundamentals of Immunology: Textbook.-M: Medicine, 608s, p. 171 second paragraph, pp. 172-173 (1999).
Oppposition dated Dec. 15, 2021 against corresponding Colombian Application No. NC2021/0010115, 32 pages (16 pages of English Translation and 16 pages of Original Document).
Lu et al., Linkers Having a Crucial Role in Antibody—Drug Conjugates, Int. J. Mol. Sci., 17(4):561 (2016).
Nakada et al., Novel antibody drug conjugates containing exatecan derivative-based cytotoxic payloads, Bioorg. Med. Chem. Lett., 26(6):1542-1545 (2016).
Office Action, mailed Nov. 25, 2022, Russian Patent Application No. 2020141476.
Supplementary European Application No. 19870506.3, European Search Report and Opinion, mailed Oct. 7, 2022.
Ambrosini et al., 68Ga-DOTA-peptides in the diagnosis of NET, PET Clin., 9 (1): 37-42 (2014).
Jorgensen, L., et al., Recent trends in stabilising peptides and proteins in pharmaceutical formulation—considerations in the choice of excipients, Expert Opinion on Drug Delivery, 6(11):1219-1230 (2009).
RU Office Action Mailed on Jan. 13, 2023 for RU Application No. 2021112023.
Wang et al., Antibody Structure, Instability, and Formulation, Journal of Pharmaceutical Sciences, 96(1):1-26 (2007).
Wang, Instability, stabilization, and formulation of liquid protein pharmaceuticals, Int. J. Phann., 185(2):129-88 (1999).
Taiwanese Office Action issued May 27, 2022 in Taiwanese Patent Application No. 107123231 12 pages (6 pages of English Translation and 6 pages of Original Document).
Akizawa et al., Renal uptake and metabolism of radiopharmaceuticals derived from peptides and proteins, Advanced drug deliver reviews, 60:1319-1328 (2008).
Arakawa, How do additives stabilize proteins in freezing operations, Protein, nucleic acid and enzyme, 37(9):1517-1523 (1992) (Non-official translation).
CEA-SCAN (Registered), For the Preparation of Technetium Tc 99m Arcitumomab, Sterile, Non-Pyrogenic, Lyophilized Powder for Intravenou s Use Only, URL https://pharmacyce.unm.edu/nuclear_program/neolibrary/libraryfiles/package_inserts/cea-scan.pdf, 11 pages.
Cheng, 99mTc-arcitumomab—Molecular Imaging and Contrast Agent Database, (MICAD) Update: Mar. 17, 2008, , <URL:https://www.ncbi.nlm.nih.gov/books/NBK23676/> 6 pages.
Danielczyk et al., PankoMab: a potent new generation anti-tumour MUCI antibody, Cancer Immunol. Immunother., 55(11):1337-1347 (2006).
Extended European Search Report European Application No. 18827622.4, European Search Report, mailed Feb. 22, 2021.
Extended European search Report European Application No. 17870672.7, European Search Report, mailed Jul. 6, 2020.
Hughes et al., Use of carcinoembryonic antigen radioimmunodetection and computed tomography for predicting the resectability of recurrent colorectal cancer, Ann. Surg., 226:621-631 (1997).
Imabori et al., Biochemical Dictionary, 3rd edition, Tokyo Kagaku Dojin KK, 1267 (2002), ISBN 4-8079-0480-9, left column, "HEPES", (non-official translation).
International Application No. PCT/JP19/039793, International Search Report and Written Opinion, mailed Dec. 24, 2019.
International Application No. PCT/JP2017/041486, International Search Report, mailed Feb. 13, 2018.
International Application No. PCT/JP2018/025618, International Preliminary Report on Patentability, mailed Jan. 16, 2020.
International Application No. PCT/JP2018/025618, International Search Report and Written Opinion, mailed Sep. 18, 2018.
International Application No. PCT/JP2019/019663, International Search Report, mailed Aug. 13, 2019.
Kamigaki et al., Improved tumor detection by anti-cea chimeric fab oligomers with disulfide linkages in a pancreatic-carcinoma-xenograft model, Int. J. Cancer, 66(2):261-267 (1996).
Kiyoshi et al., Affinity improvement of a therapeutic antibody by structure-based computational design: generation of electrostatic interactions in the transition state stabilizes the antibody-antigen complex, PLOS ONE, 9(1):1-9, e87099, (2014).
Lavrsen et al., Aberrantly glycosylated MUCI is expressed on the surface of breast cancer cells and a target for antibody-dependent cell-mediated cytotoxicity, Glycoconj. J., 30(3):227-236 (2013).
Li et al., A versatile bifunctional chelate for radiolabeling humanized anti-CEA antibody with In-111 and Cu-64 at either thiol or amino groups: PET Imaging of CEA-Positive Tumors with Whole Antibodies, Bioconjug. Chem., 19:89-96 (2008).
Nittka et al., Radioimmunoimaging of Liver Metastases with PET Using a 64Cu-Labeled CEA Antibody in Transgenic Mice, PLOS ONE, 9(9):e106921 (2014).
Perk et al., P-Isothiocyanatobenzyl-desferrioxamine: a new bifunctional chelate for facile radiolabeling of monoclonal antibodies with zirconium-89 for immuno-PET imaging, Eur. J. Nucl. Med. Mol. Imaging, 37(2):250-259 (2010).
Rosenthal et al., Sensitivity and specificity of cetuximab-IRDyeSOOCW to identify regional metastatic disease in head and neck cancer, Clinical Cancer Research, 23(16):4744-4752 (2017).
Shirai et al., High-resolution modeling of antibody structures by a combination of bloinformatics, expert knowledge, and molecular simulations, 82(8):1624-1635 (2014).
Susumu et al., Solution Properties of Antibody Pharmaceuticals, Journal of Pharmaceutical Science and Technology, Japan, 74(1):12-18 (2014).
Uchiyama, Analytical tips for biopharmaceutics: foundation and application for quality assessment Part 6: property of protein solution, Pharm tech Japan, 34(1):109-120 (2018), (Non-official translation).
Van De Watering et al., Zirconium-89 labeled antibodies: a new tool for molecular imaging in cancer patients, BioMed. Research International, 2014, Article ID 203601:1-13 (2014).
Willkomm et al., FDG PET and immunoscintigraphy with 99mTc-labeled antibody fragments for detection of the recurrence of colorectal carcinoma, J. Nucl. Med., 41:1657-1663 (2000).
Yazaki et al., Humanization of the anti-CEA T84.66 antibody based on crystal structure data, Protein engineering design and selection, 17(5):481-489 (2004).
Almagro et al., "Humanization of antibodies", Frontiers in Bioscience, Albertson, NY, US, vol. 13, pp. 1619-1633 (2008).
Extended European Search Report in Application No. 19804452.1 issued Apr. 5, 2022.
Gold et al., "Combined 90Yttrium-dota-labeled PAM4 Antibody Radioimmunotherapy and Gemcitabine Radiosensitization for the Treatment of a Human Pancreatic Cancer Xenograft", International Journal of Cancer, vol. 109, No. 4, pp. 618-626 (2004).

* cited by examiner

SEQUENCE LISTING

<160> NUMBER OF SEQ ID NOS: 19

<210> SEQ ID NO 1

```
<211> LENGTH: 678
<212> TYPE: DNA
<213> ORGANISM: Artificial Sequence
<220> FEATURE:
<223> OTHER INFORMATION: DNA encoding PB009-1 Fab heavy chain fragment
<220> FEATURE:
<221> NAME/KEY: CDS
<222> LOCATION: (1)..(678)

<400> SEQUENCE: 1
```

| | | | | | | | | | | | | | | | | |
|---|---|---|---|---|---|---|---|---|---|---|---|---|---|---|---|---|
| gaa | gtg | cag | ctg | gtg | gaa | tct | ggc | ggc | gga | ctg | gtg | cag | cct | ggc | gga | 48 |
| Glu | Val | Gln | Leu | Val | Glu | Ser | Gly | Gly | Gly | Leu | Val | Gln | Pro | Gly | Gly | |
| 1 | | | | 5 | | | | | 10 | | | | | 15 | | |
| tct | ctg | aga | ctg | agc | tgt | gcc | gcc | agc | ggc | ttc | aac | atc | cgg | gac | acc | 96 |
| Ser | Leu | Arg | Leu | Ser | Cys | Ala | Ala | Ser | Gly | Phe | Asn | Ile | Arg | Asp | Thr | |
| | | | 20 | | | | | 25 | | | | | 30 | | | |
| tac | atg | cac | tgg | gtg | cgc | cag | gcc | cct | ggc | aag | gga | ctg | gaa | tgg | gtg | 144 |
| Tyr | Met | His | Trp | Val | Arg | Gln | Ala | Pro | Gly | Lys | Gly | Leu | Glu | Trp | Val | |
| | | 35 | | | | | 40 | | | | | 45 | | | | |
| gcc | aga | atc | gac | ccc | gcc | aac | ggc | aac | agc | aga | tac | gtg | ccc | aag | ttc | 192 |
| Ala | Arg | Ile | Asp | Pro | Ala | Asn | Gly | Asn | Ser | Arg | Tyr | Val | Pro | Lys | Phe | |
| 50 | | | | | 55 | | | | | 60 | | | | | | |
| cag | ggc | cgg | ttc | acc | atc | agc | gcc | gac | acc | agc | aga | aac | acc | gcc | tac | 240 |
| Gln | Gly | Arg | Phe | Thr | Ile | Ser | Ala | Asp | Thr | Ser | Arg | Asn | Thr | Ala | Tyr | |
| 65 | | | | 70 | | | | | 75 | | | | | 80 | | |
| ctg | cag | atg | aac | agc | ctg | cgg | gcc | gag | gac | acc | gcc | gtg | tac | tac | tgt | 288 |
| Leu | Gln | Met | Asn | Ser | Leu | Arg | Ala | Glu | Asp | Thr | Ala | Val | Tyr | Tyr | Cys | |
| | | | | 85 | | | | | 90 | | | | | 95 | | |
| gcc | ccc | ttc | ggc | tac | tac | gtg | tcc | gac | tac | gcc | atg | gcc | tat | tgg | ggc | 336 |
| Ala | Pro | Phe | Gly | Tyr | Tyr | Val | Ser | Asp | Tyr | Ala | Met | Ala | Tyr | Trp | Gly | |
| | | | 100 | | | | | 105 | | | | | 110 | | | |
| cag | ggc | acc | ctc | gtg | aca | gtg | tcc | tca | gcc | tcc | acc | aag | ggc | cca | tcg | 384 |
| Gln | Gly | Thr | Leu | Val | Thr | Val | Ser | Ser | Ala | Ser | Thr | Lys | Gly | Pro | Ser | |
| | | 115 | | | | | 120 | | | | | 125 | | | | |
| gtc | ttc | ccc | ctg | gca | ccc | tcc | tcc | aag | agc | acc | tct | ggg | ggc | aca | gcg | 432 |
| Val | Phe | Pro | Leu | Ala | Pro | Ser | Ser | Lys | Ser | Thr | Ser | Gly | Gly | Thr | Ala | |
| 130 | | | | | 135 | | | | | 140 | | | | | | |
| gcc | ctg | ggc | tgc | ctg | gtc | aag | gac | tac | ttc | ccc | gaa | ccg | gtg | acg | gtg | 480 |
| Ala | Leu | Gly | Cys | Leu | Val | Lys | Asp | Tyr | Phe | Pro | Glu | Pro | Val | Thr | Val | |
| 145 | | | | 150 | | | | | 155 | | | | | 160 | | |
| tcg | tgg | aac | tca | ggc | gcc | ctg | acc | agc | ggc | gtg | cac | acc | ttc | ccg | gct | 528 |
| Ser | Trp | Asn | Ser | Gly | Ala | Leu | Thr | Ser | Gly | Val | His | Thr | Phe | Pro | Ala | |
| | | | | 165 | | | | | 170 | | | | | 175 | | |
| gtc | cta | cag | tcc | tca | gga | ctc | tac | tcc | ctt | agt | agc | gtg | gtg | acc | gtg | 576 |
| Val | Leu | Gln | Ser | Ser | Gly | Leu | Tyr | Ser | Leu | Ser | Ser | Val | Val | Thr | Val | |
| | | | 180 | | | | | 185 | | | | | 190 | | | |
| ccc | tcc | agc | agc | ttg | ggc | acc | cag | acc | tac | atc | tgc | aac | gtg | aat | cac | 624 |
| Pro | Ser | Ser | Ser | Leu | Gly | Thr | Gln | Thr | Tyr | Ile | Cys | Asn | Val | Asn | His | |
| | | 195 | | | | | 200 | | | | | 205 | | | | |
| aag | ccc | agc | aac | acc | aag | gtg | gac | aag | aaa | gtt | gag | ccc | aaa | tct | tgt | 672 |
| Lys | Pro | Ser | Asn | Thr | Lys | Val | Asp | Lys | Lys | Val | Glu | Pro | Lys | Ser | Cys | |
| 210 | | | | | 215 | | | | | 220 | | | | | | |
| gac | tga | | | | | | | | | | | | | | | 678 |
| Asp | | | | | | | | | | | | | | | | |
| 225 | | | | | | | | | | | | | | | | |

```
<210> SEQ ID NO 2
<211> LENGTH: 225
<212> TYPE: PRT
<213> ORGANISM: Artificial Sequence
<220> FEATURE:
<223> OTHER INFORMATION: Synthetic Construct
```

<400> SEQUENCE: 2

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Asp Thr
            20                  25                  30

Tyr Met His Trp Val Arg Gln Ala Pro Gly Lys Gly Leu Glu Trp Val
        35                  40                  45

Ala Arg Ile Asp Pro Ala Asn Gly Asn Ser Arg Tyr Val Pro Lys Phe
    50                  55                  60

Gln Gly Arg Phe Thr Ile Ser Ala Asp Thr Ser Arg Asn Thr Ala Tyr
65                  70                  75                  80

Leu Gln Met Asn Ser Leu Arg Ala Glu Asp Thr Ala Val Tyr Tyr Cys
                85                  90                  95

Ala Pro Phe Gly Tyr Tyr Val Ser Asp Tyr Ala Met Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp
225
```

<210> SEQ ID NO 3
<211> LENGTH: 657
<212> TYPE: DNA
<213> ORGANISM: Artificial Sequence
<220> FEATURE:
<223> OTHER INFORMATION: DNA encoding PB009-1 Fab light chain
<220> FEATURE:
<221> NAME/KEY: CDS
<222> LOCATION: (1)..(657)

<400> SEQUENCE: 3

```
gac atc cag ctg acc cag agc cct agc agc ctg tct gcc agc gtg ggc    48
Asp Ile Gln Leu Thr Gln Ser Pro Ser Ser Leu Ser Ala Ser Val Gly
1               5                   10                  15 gac aga gtg acc atc acc tgt aga gcc ggc gag agc gtg gac atc ttc    96
Asp Arg Val Thr Ile Thr Cys Arg Ala Gly Glu Ser Val Asp Ile Phe
            20                  25                  30 ggc gtg gga ttt ctg cac tgg tat cag cag aag ccc ggc aag gcc ccc   144
Gly Val Gly Phe Leu His Trp Tyr Gln Gln Lys Pro Gly Lys Ala Pro
        35                  40                  45 aag ctg ctg atc tac aga gcc agc aac ctg gaa agc ggc atc ccc agc   192
Lys Leu Leu Ile Tyr Arg Ala Ser Asn Leu Glu Ser Gly Ile Pro Ser
    50                  55                  60 aga ttc agc ggc agc ggc tcc aga acc gac ttc acc ctg acc atc agc   240
Arg Phe Ser Gly Ser Gly Ser Arg Thr Asp Phe Thr Leu Thr Ile Ser
65                  70                  75                  80
```

```
agc ctg cag ccc gag gac ttc gcc acc tac tac tgc cag cag acc aac     288
Ser Leu Gln Pro Glu Asp Phe Ala Thr Tyr Tyr Cys Gln Gln Thr Asn
            85                  90                  95 gag gac ccc tac acc ttt ggc cag ggc acc aag gtg gaa atc aag cgt     336
Glu Asp Pro Tyr Thr Phe Gly Gln Gly Thr Lys Val Glu Ile Lys Arg
        100                 105                 110 acg gtg gct gca cca tct gtc ttc atc ttc ccg cca tct gat gag cag     384
Thr Val Ala Ala Pro Ser Val Phe Ile Phe Pro Pro Ser Asp Glu Gln
    115                 120                 125 ttg aaa tct gga act gcc tct gtt gtg tgc ctg ctg aat aac ttc tat     432
Leu Lys Ser Gly Thr Ala Ser Val Val Cys Leu Leu Asn Asn Phe Tyr
130                 135                 140 ccc aga gag gcc aaa gta cag tgg aag gtg gat aac gcc ctc caa tcg     480
Pro Arg Glu Ala Lys Val Gln Trp Lys Val Asp Asn Ala Leu Gln Ser
145                 150                 155                 160 ggt aac tcc cag gag agt gtc aca gag cag gac agc aag gac agc acc     528
Gly Asn Ser Gln Glu Ser Val Thr Glu Gln Asp Ser Lys Asp Ser Thr
                165                 170                 175 tac agc ctg agc agc acc ctg acg ctg agc aaa gca gac tac gag aaa     576
Tyr Ser Leu Ser Ser Thr Leu Thr Leu Ser Lys Ala Asp Tyr Glu Lys
            180                 185                 190 cac aaa gtc tac gcc tgc gaa gtc acc cat cag ggc ctg agc tcg ccc     624
His Lys Val Tyr Ala Cys Glu Val Thr His Gln Gly Leu Ser Ser Pro
        195                 200                 205 gtc aca aag agc ttc aac agg gga gag tgt tag                         657
Val Thr Lys Ser Phe Asn Arg Gly Glu Cys
    210                 215

<210> SEQ ID NO 4
<211> LENGTH: 218
<212> TYPE: PRT
<213> ORGANISM: Artificial Sequence
<220> FEATURE:
<223> OTHER INFORMATION: Synthetic Construct

<400> SEQUENCE: 4

Asp Ile Gln Leu Thr Gln Ser Pro Ser Ser Leu Ser Ala Ser Val Gly
1               5                   10                  15

Asp Arg Val Thr Ile Thr Cys Arg Ala Gly Glu Ser Val Asp Ile Phe
            20                  25                  30

Gly Val Gly Phe Leu His Trp Tyr Gln Gln Lys Pro Gly Lys Ala Pro
        35                  40                  45

Lys Leu Leu Ile Tyr Arg Ala Ser Asn Leu Glu Ser Gly Ile Pro Ser
    50                  55                  60

Arg Phe Ser Gly Ser Gly Ser Arg Thr Asp Phe Thr Leu Thr Ile Ser
65                  70                  75                  80

Ser Leu Gln Pro Glu Asp Phe Ala Thr Tyr Tyr Cys Gln Gln Thr Asn
            85                  90                  95

Glu Asp Pro Tyr Thr Phe Gly Gln Gly Thr Lys Val Glu Ile Lys Arg
        100                 105                 110

Thr Val Ala Ala Pro Ser Val Phe Ile Phe Pro Pro Ser Asp Glu Gln
    115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175
```

```
Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 5
<211> LENGTH: 669
<212> TYPE: DNA
<213> ORGANISM: Artificial Sequence
<220> FEATURE:
<223> OTHER INFORMATION: DNA encoding P10-1 Fab heavy chain fragment

<400> SEQUENCE: 5
caggtgcagc tggtgcagtc tggcgccgaa gtgaagaaac aggcgccag cgtgaaggtg      60 tcctgcaagg ccagcggcta caccttcacc aactacggcc tgagctgggt gcgccaggct     120
cctggacagg gactggaatg gatgggcgag aaccaccctg gcagcggcat catctaccac     180
aacgagaagt tccggggcag agtgaccctg accgccgacc ggagcaccag caccgcctac     240
atggaactga gcagcctgcg gagcgaggac accgccgtgt actactgtgc cagaagcagc     300
ggcaccagag gctttgccta ttggggacag ggcaccctcg tgaccgtgtc ctcagcctcc     360
accaagggcc catcggtctt ccccctggca ccctcctcca agagcacctc tgggggcaca     420
gcggccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctta gtagcgtggt gaccgtgccc tccagcagct gggcaccca gacctacatc      600 tgcaacgtga atcacaagcc cagcaacacc aaggtggaca gaaagttga gcccaaatct     660 tgtgactga                                                             669

<210> SEQ ID NO 6
<211> LENGTH: 222
<212> TYPE: PRT
<213> ORGANISM: Artificial Sequence
<220> FEATURE:
<223> OTHER INFORMATION: P10-1 Fab heavy chain fragment

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Leu Ser Trp Val Arg Gln Ala Pro Gly Gln Gly Leu Glu Trp Met
        35                  40                  45

Gly Glu Asn His Pro Gly Ser Gly Ile Ile Tyr His Asn Glu Lys Phe
    50                  55                  60

Arg Gly Arg Val Thr Leu Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Ser Ser Gly Thr Arg Gly Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
```

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp
    210                 215                 220

<210> SEQ ID NO 7
<211> LENGTH: 669
<212> TYPE: DNA
<213> ORGANISM: Artificial Sequence
<220> FEATURE:
<223> OTHER INFORMATION: DNA encoding P10-2 Fab heavy chain fragment

<400> SEQUENCE: 7
caggtgcagc tggtgcagtc tggcgccgaa gtgaagaaac caggcgccag cgtgaaggtg      60
tcctgcaagg ccagcggcta caccttcacc aactacggcc tgagctgggt gcgccaggct     120
cctggacagg gactggaatg gatgggcgag aaccacccctg cagcggcat catctaccac     180 aacgagaagt tccggggcag agtgaccctg accgccgacc ggagcaccag caccgcctac     240
atggaactga gcagcctgcg gagcgaggac accgccgtgt actactgtgc cagaagcagc     300
ggcaccagag gctttgacta ttggggacag ggcaccctcg tgaccgtgtc ctcagcctcc     360
accaagggcc catcggtctt ccccctggca ccctcctcca agagcacctc tgggggcaca     420
gcggccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctta gtagcgtggt gaccgtgccc tccagcagct gggcaccca gacctacatc     600 tgcaacgtga atcacaagcc cagcaacacc aaggtggaca agaaagttga gcccaaatct     660
tgtgactga                                                            669

<210> SEQ ID NO 8
<211> LENGTH: 222
<212> TYPE: PRT
<213> ORGANISM: Artificial Sequence
<220> FEATURE:
<223> OTHER INFORMATION: P10-2 Fab heavy chain fragment

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Leu Ser Trp Val Arg Gln Ala Pro Gly Gln Gly Leu Glu Trp Met
            35                  40                  45

Gly Glu Asn His Pro Gly Ser Gly Ile Ile Tyr His Asn Glu Lys Phe
    50                  55                  60

Arg Gly Arg Val Thr Leu Thr Ala Asp Arg Ser Thr Ser Thr Ala Tyr
65              70                  75                  80

Met Glu Leu Ser Ser Leu Arg Ser Glu Asp Thr Ala Val Tyr Tyr Cys
                85                  90                  95

Ala Arg Ser Ser Gly Thr Arg Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp
    210                 215                 220

<210> SEQ ID NO 9
<211> LENGTH: 660
<212> TYPE: DNA
<213> ORGANISM: Artificial Sequence
<220> FEATURE:
<223> OTHER INFORMATION: DNA encoding P10-1 and P10-2 Fab light chain

<400> SEQUENCE: 9
gacgtcgtga tgacccagac ccctctgagc ctgagcgtga cacctggaca gcctgccagc      60
atcagctgca gatccagcca gagcatcgtg cacagcaacg gcaacaccta cctggaatgg     120
tatctgcaga gcccggccga gcccccag ctgctgatct acagggtgtc caaccggttc       180
agcggcgtgc ccgacagatt ttctggcagc ggctccggca ccgacttcac cctgaagatc     240
tcccgggtgg aagccgagga cgtgggcgtg tactactgtt ttcaaggcag ccacggcccc     300
tggacctttg gccagggaac aaagctggaa atcaagcgta cggtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctg     540
agcagcaccc tgacgctgag caaagcagac tacgagaaac acaaagtcta cgcctgcgaa     600
gtcacccatc agggcctgag ctcgcccgtc acaaagagct tcaacagggg agagtgttag     660

<210> SEQ ID NO 10
<211> LENGTH: 219
<212> TYPE: PRT
<213> ORGANISM: Artificial Sequence
<220> FEATURE:
<223> OTHER INFORMATION: P10-1 and P10-2 Fab light chain

<400> SEQUENCE: 10

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile 65                  70                  75                  80
Ser Arg Val Glu Ala Glu Asp Val Gly Val Tyr Tyr Cys Phe Gln Gly
                    85                  90                  95

Ser His Gly Pro Trp Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 11
<211> LENGTH: 354
<212> TYPE: DNA
<213> ORGANISM: Artificial Sequence
<220> FEATURE:
<223> OTHER INFORMATION: DNA encoding P10-1 Fab heavy chain variable
      region

<400> SEQUENCE: 11
caggtgcagc tggtgcagtc tggcgccgaa gtgaagaaac caggcgccag cgtgaaggtg      60
tcctgcaagg ccagcggcta caccttcacc aactacggcc tgagctgggt gcgccaggct     120
cctggacagg gactggaatg gatgggcgag aaccaccctg gcagcggcat catctaccac     180
aacgagaagt tccggggcag agtgaccctg accgccgacc ggagcaccag caccgcctac     240
atggaactga gcagcctgcg gagcgaggac accgccgtgt actactgtgc cagaagcagc     300
ggcaccagag gctttgccta ttggggacag ggcacccctcg tgaccgtgtc ctca          354

<210> SEQ ID NO 12
<211> LENGTH: 118
<212> TYPE: PRT
<213> ORGANISM: Artificial Sequence
<220> FEATURE:
<223> OTHER INFORMATION: P10-1 Fab heavy chain variable region

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Leu Ser Trp Val Arg Gln Ala Pro Gly Gln Gly Leu Glu Trp Met
        35                  40                  45

Gly Glu Asn His Pro Gly Ser Gly Ile Ile Tyr His Asn Glu Lys Phe
    50                  55                  60

Arg Gly Arg Val Thr Leu Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

```
Ala Arg Ser Ser Gly Thr Arg Gly Phe Ala Tyr Trp Gly Gln Gly Thr
            100                 105                 110

Leu Val Thr Val Ser Ser
        115

<210> SEQ ID NO 13
<211> LENGTH: 354
<212> TYPE: DNA
<213> ORGANISM: Artificial Sequence
<220> FEATURE:
<223> OTHER INFORMATION: DNA encoding P10-2 Fab heavy chain variable
      region

<400> SEQUENCE: 13
caggtgcagc tggtgcagtc tggcgccgaa gtgaagaaac caggcgccag cgtgaaggtg      60
tcctgcaagg ccagcggcta caccttcacc aactacggcc tgagctgggt gcgccaggct     120
cctggacagg gactggaatg gatgggcgag aaccacctg gcagcggcat catctaccac      180
aacgagaagt tccggggcag agtgaccctg accgccgacc ggagcaccag caccgcctac     240
atggaactga gcagcctgcg gagcgaggac accgccgtgt actactgtgc cagaagcagc     300
ggcaccagag gctttgacta ttggggacag ggcaccctcg tgaccgtgtc ctca           354

<210> SEQ ID NO 14
<211> LENGTH: 118
<212> TYPE: PRT
<213> ORGANISM: Artificial Sequence
<220> FEATURE:
<223> OTHER INFORMATION: P10-2 Fab heavy chain variable region

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Leu Ser Trp Val Arg Gln Ala Pro Gly Gln Gly Leu Glu Trp Met
        35                  40                  45

Gly Glu Asn His Pro Gly Ser Gly Ile Ile Tyr His Asn Glu Lys Phe
    50                  55                  60

Arg Gly Arg Val Thr Leu Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Gly Thr Arg Gly Phe Asp Tyr Trp Gly Gln Gly Thr
            100                 105                 110

Leu Val Thr Val Ser Ser
        115

<210> SEQ ID NO 15
<211> LENGTH: 339
<212> TYPE: DNA
<213> ORGANISM: Artificial Sequence
<220> FEATURE:
<223> OTHER INFORMATION: DNA encoding P10-1 and P10-2 Fab light chain
      variable region

<400> SEQUENCE: 15
gacgtcgtga tgacccagac ccctctgagc ctgagcgtga cacctggaca gcctgccagc     60
atcagctgca gatccagcca gagcatcgtg cacagcaacg gcaacaccta cctggaatgg    120
```

```
tatctgcaga agcccggcca gagcccccag ctgctgatct acagggtgtc caaccggttc      180
agcggcgtgc ccgacagatt ttctggcagc ggctccggca ccgacttcac cctgaagatc      240
tcccgggtgg aagccgagga cgtgggcgtg tactactgtt tcaaggcag ccacggcccc       300 tggacctttg gccagggaac aaagctggaa atcaagcgt                             339
```

```
<210> SEQ ID NO 16
<211> LENGTH: 113
<212> TYPE: PRT
<213> ORGANISM: Artificial Sequence
<220> FEATURE:
<223> OTHER INFORMATION: P10-1 and P10-2 Fab light chain variable region

<400> SEQUENCE: 16

Asp Val Val Met Thr Gln Thr Pro Leu Ser Leu Ser Val Thr Pro Gly
1               5                   10                  15

Gln Pro Ala Ser Ile Ser Cys Arg Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Gly Pro Trp Thr Phe Gly Gln Gly Thr Lys Leu Glu Ile Lys
            100                 105                 110

Arg

<210> SEQ ID NO 17
<211> LENGTH: 19
<212> TYPE: PRT
<213> ORGANISM: Artificial Sequence
<220> FEATURE:
<223> OTHER INFORMATION: Heavy chain signal sequence for PB009-1, P10-1
      and P10-2 Fab

<400> SEQUENCE: 17

Met Glu Trp Ser Trp Val Phe Leu Phe Phe Leu Ser Val Thr Thr Gly
1               5                   10                  15

Val His Ser

<210> SEQ ID NO 18
<211> LENGTH: 20
<212> TYPE: PRT
<213> ORGANISM: Artificial Sequence
<220> FEATURE:
<223> OTHER INFORMATION: Light chain signal sequence for PB009-1, P10-1
      and P10-2 Fab

<400> SEQUENCE: 18

Met Ser Val Pro Thr Gln Val Leu Gly Leu Leu Leu Leu Trp Leu Thr
1               5                   10                  15

Asp Ala Arg Cys
            20

<210> SEQ ID NO 19
<211> LENGTH: 20
<212> TYPE: PRT
<213> ORGANISM: Artificial Sequence
```

```
<220> FEATURE:
<223> OTHER INFORMATION: Tandem repeat sequence of an extracellular
      domain of MUC1

<400> SEQUENCE: 19

His Gly Val Thr Ser Ala Pro Asp Thr Arg Pro Ala Pro Gly Ser Thr
1               5                   10                  15

Ala Pro Pro Ala
            20
```

PHARMACEUTICAL COMPOSITION CONTAINING TAGGED SITE-ANTIHUMAN ANTIBODY FAB FRAGMENT COMPLEX

CROSS REFERENCE TO RELATED APPLICATIONS

This application is a 35 U.S.C. § 371 National Phase Entry Application of International Application No. PCT/JP2019/039793, filed Oct. 9, 2019, which claims foreign priority to Japanese Application No. 2018-191605 filed Oct. 10, 2018, which are all incorporated herein by reference in their entireties.

INCORPORATION BY REFERENCE OF MATERIAL SUBMITTED ELECTRONICALLY

A Sequence Listing, which is a part of the present disclosure, is submitted concurrently with the specification as a text file. The name of the text file containing the Sequence Listing is "56720_Seqlisting.txt." The Sequence Listing was created on Apr. 8, 2021, and is 26,759 bytes in size. The subject matter of the Sequence Listing is incorporated herein in its entirety by reference.

TECHNICAL FIELD

The present invention relates to a stable pharmaceutical composition comprising a labeling moiety-anti-human antibody Fab fragment conjugate. Particularly, the present invention relates to a stable pharmaceutical composition comprising a labeling moiety-anti-human CEACAM5 antibody Fab fragment conjugate or a labeling moiety-anti-human MUC1 antibody Fab fragment conjugate. The present invention also relates to a method for producing a pharmaceutical composition comprising a labeling moiety-anti-human antibody Fab fragment conjugate, and a method for stably preserving a labeling moiety-anti-human antibody Fab fragment conjugate.

BACKGROUND ART

Development of genetic modification technology has enabled use of antibodies such as immunoglobulin, monoclonal antibodies and humanized antibodies as medicinal products. For example, for diagnosing and treating cancers, antibodies bound to anticancer agents, metal radioisotopes, fluorescent dyes and the like are used. Targeting using an antibody is known to have high specificity to tumor cells and cause little side-effects. Under such circumstances, monoclonal antibodies labeled with metal radioisotopes, and the like have been heretofore developed (Patent literature 1).

Meanwhile, antibodies generally have a long half-life in blood and require a period as long as 4 days to 5 days for reaching a tumor-to-blood ratio that confers a signal-to-background ratio sufficient for visualizing a cancer, after administration into the body (Clin. Pharmacol. Ther.; 2010; 87: 586-592). Also, the Fc regions of antibodies cause a pharmacological effect of antibody-dependent cellular cytotoxicity (ADCC) or complement-dependent cytotoxicity (CDC) (Glycoconj. J.; 2013; 30: 227-236; and Curr. Opin. Biotechnol.; 2002; 13: 609-614). Furthermore, antibodies are metabolized in the liver and therefore highly accumulate in the liver, regardless of a target. However, it is difficult to detect lesions of hepatic metastasis of colorectal cancer using antibodies because the early metastasis of colorectal cancer is localized to the liver (Clin. Pharmacol. Ther.; 2010; 87: 586-592).

On the other hand, low-molecular recombinant antibody fragments such as Fab easily arrive at lesions because of their high tissue penetration, and production at low cost using an expression system in E. coli or yeasts can be expected. Utilization of the low-molecular recombinant antibody fragments as a diagnostic drug is expected because of their short half-lives in blood and the feature of renal excretion (Nat. Biotechnol.; 2005; 23: 1126-1136).

Under such circumstances, studies have been made on utilization of Fab fragment conjugates in which a metal radioisotope is coordinated and Fab fragments bound to a fluorescent dye for the purpose of diagnosing a cancer.

Many studies have been heretofore made on methods for stably preserving antibodies. For example, Patent Literature 2 discloses a method in which a nonionic surfactant and a saccharide are added to a formulation containing a humanized C4C1 Fab fragment, and the pH is adjusted to a specific range to achieve stabilization. Further, Patent Literature 3 discloses a method in which a buffering agent is added to a formulation comprising a human antibody to IL-1β, and the pH is adjusted to a specific range to achieve stabilization.

CITATION LIST

Patent Literature

PTL 1: Japanese Translation of PCT International Application Publication No. 2013-510093
PTL 2: International Publication No. WO 00/66160
PTL 3: Japanese Translation of PCT International Application Publication No. 2012-511540

SUMMARY OF INVENTION

Technical Problem

Monovalent Fab fragments have a molecular weight of approximately 50 kDa, which is smaller than that (approximately 150 kDa) of antibodies, undergo renal excretion, and also have a short half-life in blood. They lack a Fc region and therefore cause neither ADCC nor CDC. From these features, Fab fragments in which a metal radioisotope is coordinated or Fab fragments bound to a fluorescent dye are expected to be more effective as diagnostic drugs as compared with antibodies.

However, Fab fragments bound to a ligand or a fluorescent dye have the problem that multimers or insoluble subvisible particles are easily generated due to heat stress or light stress during preservation and the problem that insoluble subvisible particles are generated in the process of thawing and stirring before use. Addition of various compounds into a preservation solution for stabilization may cause problems of coordination efficiency and fluorescence color degradation.

An object of the present invention is to provide a pharmaceutical composition comprising a labeling moiety-anti-human antibody Fab fragment conjugate, which enables suppression of generation of multimers or insoluble subvisible particles during preservation, and the like. Another object of the present invention is to provide a pharmaceutical composition comprising a labeling moiety-anti-human antibody Fab fragment conjugate, which enables suppression of a decrease in coordination efficiency of a metal radioisotope to a ligand when the ligand is used as a labeling moiety. Still another object of the present invention is to provide a pharmaceutical composition comprising a labeling moiety-anti-human antibody Fab fragment conjugate, which enables suppression of fluorescent dye color degradation when a fluorescent dye is used as a labeling moiety.

Solution to Problem

The present inventors have conducted considerable diligent studies on the formulation of a pharmaceutical composition comprising a labeling moiety-anti-human antibody Fab fragment conjugate, and consequently found that by adding citric acid, phosphoric acid, 2-[4-(2-hydroxyethyl)-1-piperazinyl]ethanesulfonic acid or trishydroxymethyl aminomethane as a buffering agent, adding sucrose or glycerin as a stabilizer, and further adding a nonionic surfactant to prepare a pharmaceutical composition having a pH of 6.5 to 7.5, generation of multimers or insoluble subvisible particles during preservation of the labeling moiety-anti-human antibody Fab fragment conjugate can be suppressed, and a decrease in coordination efficiency of a metal radioisotope to a ligand and fluorescent dye color degradation can be suppressed. In this way, the present invention has been achieved.

Specifically, the present invention provides a pharmaceutical composition comprising a labeling moiety-anti-human antibody Fab fragment conjugate, which is excellent in preservation stability of the labeling moiety-anti-human antibody Fab fragment conjugate and enables suppression of a decrease in coordination efficiency of metal to the labeling moiety and labeling fluorescent dye color degradation. In one embodiment, the present invention may be as follows.

[1] A pharmaceutical composition comprising a labeling moiety-anti-human antibody Fab fragment conjugate, a buffering agent, a stabilizer and a nonionic surfactant and having a pH of 6.5 to 7.5,
   the buffering agent comprising citric acid, phosphoric acid, 2-[4-(2-hydroxyethyl)-1-piperazinyl]ethanesulfonic acid or trishydroxymethyl aminomethane,
   the stabilizer comprising sucrose or glycerin.

[2] The pharmaceutical composition according to [1], wherein the anti-human antibody Fab fragment is one or more selected from the group consisting of the following (a) and (b):
(a) an anti-human CEACAM5 antibody Fab fragment comprising a heavy chain fragment comprising a heavy chain variable region consisting of an amino acid sequence from amino acid positions 1 to 121 of SEQ ID NO: 2 and a light chain comprising a light chain variable region consisting of an amino acid sequence from amino acid positions 1 to 112 of SEQ ID NO: 4; and
(b) an anti-human CEACAM5 antibody Fab fragment comprising a heavy chain fragment comprising a heavy chain variable region derived from a heavy chain variable region consisting of an amino acid sequence from amino acid positions 1 to 121 of SEQ ID NO: 2 by the modification of glutamic acid at amino acid position 1 of SEQ ID NO: 2 into pyroglutamic acid, and a light chain comprising a light chain variable region consisting of an amino acid sequence from amino acid positions 1 to 112 of SEQ ID NO: 4, and the labeling moiety is a group represented by the following formula (I):

[Chemical Formula 1]

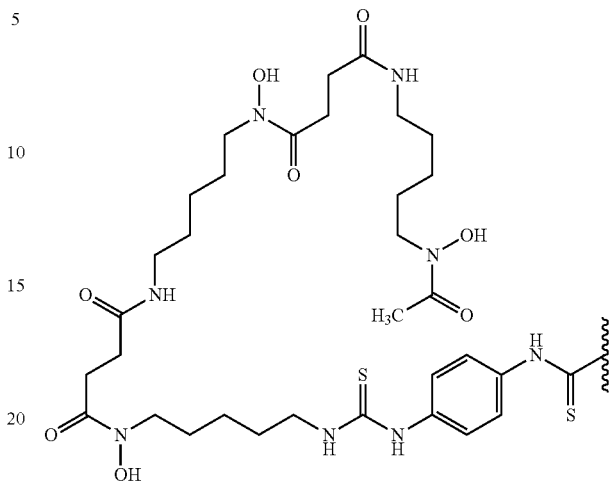

(I)

wherein the wavy line represents binding to the anti-human CEACAM5 antibody Fab fragment, where the anti-human CEACAM5 antibody Fab fragment is bound to the carbon atom of a labeling moiety terminal C(=S) group via an amino group in the anti-human CEACAM5 antibody Fab fragment.

[3] The pharmaceutical composition according to [2], wherein the anti-human antibody Fab fragment is one or more selected from the group consisting of the following (a) and (b):
(a) an anti-human CEACAM5 antibody Fab fragment comprising a heavy chain fragment consisting of the amino acid sequence represented by SEQ ID NO: 2 and a light chain consisting of the amino acid sequence represented by SEQ ID NO: 4; and
(b) an anti-human CEACAM5 antibody Fab fragment comprising a heavy chain fragment derived from a heavy chain fragment consisting of the amino acid sequence represented by SEQ ID NO: 2 by the modification of glutamic acid at amino acid position 1 of SEQ ID NO: 2 into pyroglutamic acid, and a light chain consisting of the amino acid sequence represented by SEQ ID NO: 4.

[4] The pharmaceutical composition according to [1], wherein the anti-human antibody Fab fragment is one or more selected from the group consisting of the following (a) and (b):
(a) an anti-human MUC1 antibody Fab fragment comprising a heavy chain fragment comprising a heavy chain variable region consisting of the amino acid sequence represented by SEQ ID NO: 12 or SEQ ID NO: 14 and a light chain comprising a light chain variable region consisting of the amino acid sequence represented by SEQ ID NO: 16; and
(b) an anti-human MUC1 antibody Fab fragment comprising a heavy chain fragment comprising a heavy chain variable region derived from a heavy chain variable region consisting of the amino acid sequence represented by SEQ ID NO: 12 or SEQ ID NO: 14 by the modification of glutamine at amino acid position 1 of SEQ ID NO: 12 or SEQ ID NO: 14 into pyroglutamic acid, and a light chain comprising a light chain variable region consisting of the amino acid sequence represented by SEQ ID NO: 16, and the labeling moiety is a group represented by the following formula (I):

[Chemical Formula 2]

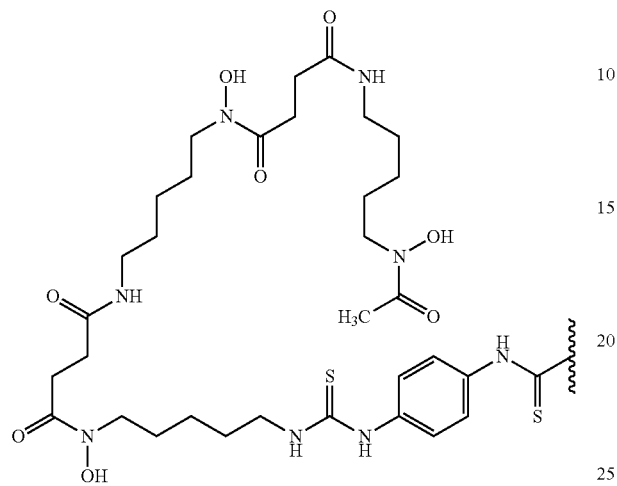

(I)

wherein the wavy line represents binding to the anti-human MUC1 antibody Fab fragment, where the anti-human MUC1 antibody Fab fragment is bound to the carbon atom of a labeling moiety terminal C(=S) group via an amino group in the anti-human MUC1 antibody Fab fragment.

[5] The pharmaceutical composition according to [4], wherein the anti-human antibody Fab fragment is one or more selected from the group consisting of the following (a) and (b):
(a) an anti-human MUC1 antibody Fab fragment comprising a heavy chain fragment consisting of the amino acid sequence represented by SEQ ID NO: 6 or SEQ ID NO: 8 and a light chain consisting of the amino acid sequence represented by SEQ ID NO: 10; and
(b) an anti-human MUC1 antibody Fab fragment comprising a heavy chain fragment derived from a heavy chain fragment consisting of the amino acid sequence represented by SEQ ID NO: 6 or SEQ ID NO: 8 by the modification of glutamine at amino acid position 1 of SEQ ID NO: 6 or SEQ ID NO: 8 into pyroglutamic acid, and a light chain consisting of the amino acid sequence represented by SEQ ID NO: 10.

[6] The pharmaceutical composition according to any one of [1] to [5], wherein the nonionic surfactant comprises Polysorbate 80.

[7] The pharmaceutical composition according to any one of [2] to [6], wherein the labeling moiety-anti-human antibody Fab fragment conjugate further comprises $^{89}$Zr.

[8] The pharmaceutical composition according to [7] for use in the diagnosis of colorectal cancer or a cancer resulting from the metastasis of colorectal cancer.

[9] The pharmaceutical composition according to [7] for use in the diagnosis of breast cancer or a cancer resulting from the metastasis of breast cancer.

[10] The pharmaceutical composition according to [1], wherein the anti-human antibody Fab fragment is one or more selected from the group consisting of the following (a) and (b):
(a) an anti-human MUC1 antibody Fab fragment comprising a heavy chain fragment comprising a heavy chain variable region consisting of the amino acid sequence represented by SEQ ID NO: 12 or SEQ ID NO: 14 and a light chain comprising a light chain variable region consisting of the amino acid sequence represented by SEQ ID NO: 16; and
(b) an anti-human MUC1 antibody Fab fragment comprising a heavy chain fragment comprising a heavy chain variable region derived from a heavy chain variable region consisting of the amino acid sequence represented by SEQ ID NO: 12 or SEQ ID NO: 14 by the modification of glutamine at amino acid position 1 of SEQ ID NO: 12 or SEQ ID NO: 14 into pyroglutamic acid, and a light chain comprising a light chain variable region consisting of the amino acid sequence represented by SEQ ID NO: 16, and the labeling moiety is a group represented by the following formula (II):

[Chemical Formula 3]

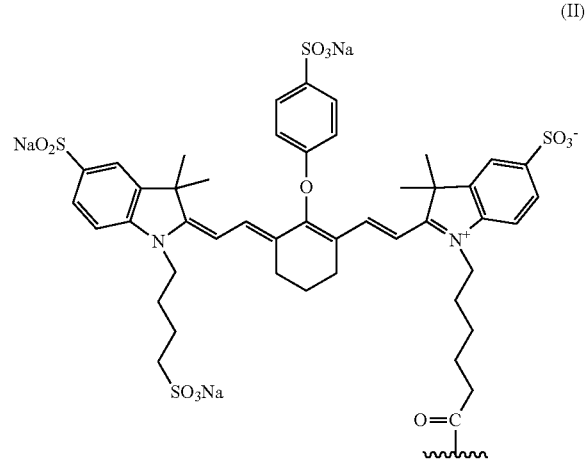

(II)

wherein the wavy line represents binding to the anti-human MUC1 antibody Fab fragment, where the anti-human MUC1 antibody Fab fragment is bound to the carbon atom of a labeling moiety terminal C(=O) group via an amino group in the anti-human MUC1 antibody Fab fragment.

[11] The pharmaceutical composition according to [10], wherein the anti-human antibody Fab fragment is one or more selected from the group consisting of the following (a) and (b):
(a) an anti-human MUC1 antibody Fab fragment comprising a heavy chain fragment consisting of the amino acid sequence represented by SEQ ID NO: 6 or SEQ ID NO: 8 and a light chain consisting of the amino acid sequence represented by SEQ ID NO: 10; and
(b) an anti-human MUC1 antibody Fab fragment comprising a heavy chain fragment derived from a heavy chain fragment consisting of the amino acid sequence represented by SEQ ID NO: 6 or SEQ ID NO: 8 by the modification of glutamine at amino acid position 1 of SEQ ID NO: 6 or SEQ ID NO: 8 into pyroglutamic acid, and a light chain consisting of the amino acid sequence represented by SEQ ID NO: 10.

[12] The pharmaceutical composition according to [10] or [11], wherein the nonionic surfactant comprises Polysorbate 80.

[13] The pharmaceutical composition according to any one of [10] to [12] for use in the diagnosis of breast cancer or a cancer resulting from the metastasis of breast cancer.
[14] The pharmaceutical composition according to [13], which is an intraoperative diagnostic drug.
[15] The pharmaceutical composition according to any one of [1] to [14], wherein the concentration of the buffering agent is 10 to 30 mmol/L.
[16] The pharmaceutical composition according to any one of [1] to [15], wherein the concentration of the stabilizer is 5 to 30 w/v %.
[17] The pharmaceutical composition according to any one of [1] to [16], wherein the concentration of the nonionic surfactant is 0.02 to 0.2 w/v %.
[18] The pharmaceutical composition according to any one of [1] to [17], which is a liquid formulation, a frozen formulation or a lyophilized formulation.
[19] A method for producing a pharmaceutical composition comprising a labeling moiety-anti-human antibody Fab fragment conjugate, comprising the steps of:
(a) producing and adding the labeling moiety-anti-human antibody Fab fragment conjugate;
(b) adding citric acid, phosphoric acid, 2-[4-(2-hydroxyethyl)-1-piperazinyl]ethanesulfonic acid or trishydroxymethyl aminomethane as a buffering agent;
(c) adding sucrose or glycerin as a stabilizer;
(d) adding a nonionic surfactant; and
(e) adjusting the pH to 6.5 to 7.5.
[20] A method for stably preserving a labeling moiety-anti-human antibody Fab fragment conjugate, comprising the steps of:
(a) adding citric acid, phosphoric acid, 2-[4-(2-hydroxyethyl)-1-piperazinyl]ethanesulfonic acid or trishydroxymethyl aminomethane as a buffering agent to a solution containing the labeling moiety-anti-human antibody Fab fragment conjugate;
(b) adding sucrose or glycerin as a stabilizer to the solution containing the labeling moiety-anti-human antibody Fab fragment conjugate;
(c) adding a nonionic surfactant to the solution containing the labeling moiety-anti-human antibody Fab fragment conjugate; and
(d) adjusting the pH of the solution containing the labeling moiety-anti-human antibody Fab fragment conjugate to 6.5 to 7.5.

Advantageous Effects of Drawings

The pharmaceutical composition of the present invention is useful in terms of stability during storage, transportation and use because it enables suppression of generation of multimers or insoluble subvisible particles during preservation of the labeling moiety-anti-human antibody Fab fragment conjugate, and enables suppression of a decrease in coordination efficiency of a metal radioisotope to a ligand and fluorescent dye color degradation. The pharmaceutical composition of the present invention is also useful in terms of safety in administration to a human because pharmaceutically acceptable buffering agents and medicinal additives are used in consideration of safety.

DESCRIPTION OF EMBODIMENTS

Hereinafter, the present invention will be described in detail. However, the present invention is not limited thereby. Scientific terms and technical terms used in relation to the present invention have meanings generally understood by those skilled in the art, unless otherwise specified herein.

1. Pharmaceutical Composition

In a certain embodiment, the present invention relates to a pharmaceutical composition comprising a labeling moiety-anti-human antibody Fab fragment conjugate, a buffering agent, a stabilizer and a nonionic surfactant and having a pH of 6.5 to 7.5, the buffering agent comprising citric acid, phosphoric acid, 2-[4-(2-hydroxyethyl)-1-piperazinyl]ethanesulfonic acid or trishydroxymethyl aminomethane, the stabilizer comprising sucrose or glycerin. The pharmaceutical composition enables suppression of generation of multimers or insoluble subvisible particles during preservation of the labeling moiety-anti-human antibody Fab fragment conjugate, and enables suppression of a decrease in coordination efficiency of a metal radioisotope to a ligand and fluorescent dye color degradation. Thus, for the pharmaceutical composition of the present invention, aggregation etc. during storage, transportation and use of the labeling moiety-anti-human antibody Fab fragment conjugate can be suppressed.

1-1. Anti-Human Antibody Fab Fragment

The basic structure of an antibody molecule is common among classes and is constituted by heavy chains having a molecular weight of 50000 to 70000 and light chains having a molecular weight of 20000 to 30000. The heavy chain usually consists of a polypeptide chain comprising approximately 440 amino acids, has a structure characteristic of each class, and is called γ, μ, α, δ, and ε chains corresponding to IgG, IgM, IgA, IgD, and IgE. IgG further has IgG1, IgG2, IgG3, and IgG4 which are called γ1, γ2, γ3, and γ4, respectively. The light chain usually consists of a polypeptide chain comprising approximately 220 amino acids and is known as two types, L and K types, which are called λ and κ chains, respectively. As for the peptide configuration of the basic structure of the antibody molecule, two homologous heavy chains and two homologous light chains are linked through disulfide bonds (S—S bonds) and non-covalent bonds to form a molecular weight of 150000 to 190000. The two light chains can pair with any of the heavy chains. An individual antibody molecule is constantly made up of two identical light chains and two identical heavy chains.

Four (or five for μ and ε chains) and two intrachain S—S bonds are present in the heavy chain and the light chain, respectively, and each constitute one loop per 100 to 110 amino acid residues. This conformation is similar among the loops and is called structural unit or domain. For both the heavy chain and the light chain, a domain positioned on the N-terminal side does not have a constant amino acid sequence even among preparations from the same classes (subclasses) of animals of the same species, and is thus called variable region. The respective domains are called heavy chain variable region ($V_H$ domain) and light chain variable region ($V_L$ domain). An amino acid sequence on the C-terminal side therefrom is almost constant on a class or subclass basis and called constant region. The respective domains are represented by $C_{H1}$, $C_{H2}$, $C_{H3}$ and CL.

The binding specificity of the antibody for an antigen depends on the amino acid sequence of a moiety constituted by the heavy chain variable region and the light chain variable region. On the other hand, biological activity such as binding to complements or various cells reflects the difference in structure among the constant regions of Igs of respective classes. It is known that the variability of the heavy chain and light chain variable regions is limited substantially by three small hypervariable regions present in both the chains. These regions are called complementarity determining regions (CDRs; CDR1, CDR2, and CDR3 in order from the N-terminal side). The remaining moieties of the variable region are called framework regions (FRs) and are relatively constant.

A region between the $C_{H1}$ domain and the $C_{H2}$ domain of the heavy chain constant region of an antibody is called hinge region. This region is rich in proline residues and contains a plurality of interchain S—S bonds that connect two heavy chains. For example, the hinge regions of human IgG1, IgG2, IgG3, and IgG4 contain 2, 4, 11, and 2 cysteine residues, respectively, which constitute S—S bonds between the heavy chains. The hinge region is a region highly sensitive to a proteolytic enzyme such as papain or pepsin. In the case of digesting an antibody with papain, the heavy chains are cleaved at a position on the N-terminal side from the inter-heavy chain S—S bonds of the hinge region and thus decomposed into two Fab fragments and one Fc fragment. The Fab fragment is constituted by a light chain and a heavy chain fragment comprising a heavy chain variable region, a $C_{H1}$ domain and a portion of the hinge region. The Fab fragment comprises variable regions and has antigen binding activity.

A certain embodiment of the anti-human antibody Fab fragment contained in the pharmaceutical composition of the present invention is an anti-human CEACAM5 antibody Fab fragment. A certain embodiment of the anti-human antibody Fab fragment contained in the pharmaceutical composition of the present invention is an anti-human MUC1 antibody Fab fragment.

1-1-1. Anti-Human CEACAM5 Antibody Fab Fragment

CEACAM5 (carcinoembryonic antigen-related cell adhesion molecule 5) is one of tumor markers, and is rarely expressed in normal tissues, but is expressed in the fetal gastrointestinal tract or colorectal cancer (BBA; 1990; 1032: 177-189; and Mol. Pathol.; 1999; 52: 174-178). CEACAM5 is known to be also expressed in breast cancer and the like (Diagn. Cytopathol.; 1993; 9: 377-382; Cancer Res.; 1990; 50: 6987-6994; Histopathology; 2000; 37: 530-535). The concentration of CEACAM5 in blood is higher in colorectal cancer patients than in healthy persons (J. Exp. Med.; 1965; 121: 439-462), and CEACAM5 is used as a tumor marker. According to the histological studies of colorectal cancer patients, CEACAM5 is highly expressed in 90% or more tissues (British J. Cancer; 2013; 108: 662-667).

The anti-human CEACAM5 antibody Fab fragment contained in the pharmaceutical composition of the present invention includes a Fab fragment having the following feature: an anti-human CEACAM5 antibody Fab fragment comprising a heavy chain fragment comprising a heavy chain variable region consisting of an amino acid sequence from amino acid positions 1 to 121 of SEQ ID NO: 2 and a light chain comprising a light chain variable region consisting of an amino acid sequence from amino acid positions 1 to 112 of SEQ ID NO: 4.

Any constant region of Igγ1, Igγ2, Igγ3 or Igγ4, etc. can be selectable as the heavy chain constant region of the anti-human CEACAM5 antibody Fab fragment contained in the pharmaceutical composition of the present invention. In one embodiment, the heavy chain constant region of the anti-human CEACAM5 antibody Fab fragment contained in the pharmaceutical composition of the present invention is a human Igγ1 constant region.

Any constant region of Igλ, or Igκ can be selectable as the light chain constant region of the anti-human CEACAM5 antibody Fab fragment contained in the pharmaceutical composition of the present invention. In one embodiment, the light chain constant region of the anti-human CEACAM5 antibody Fab fragment contained in the pharmaceutical composition of the present invention is a human Igκ constant region.

In one embodiment, the anti-human CEACAM5 antibody Fab fragment contained in the pharmaceutical composition of the present invention is the following Fab fragment: an anti-human CEACAM5 antibody Fab fragment comprising a heavy chain fragment consisting of the amino acid sequence represented by SEQ ID NO: 2 and a light chain consisting of the amino acid sequence represented by SEQ ID NO: 4.

In the case of expressing an antibody comprising a Fab fragment in cells, the antibody is known to undergo a posttranslational modification. Examples of the posttranslational modification include the cleavage of heavy chain C-terminal lysine by carboxypeptidase, the modification of heavy chain and light chain N-terminal glutamine or glutamic acid into pyroglutamic acid by pyroglutamylation, glycosylation, oxidation, deamidation, and glycation. Such a posttranslational modification is known to occur in various antibodies (J. Pharm. Sci., 2008; 97: 2426-2447).

The anti-human CEACAM5 antibody Fab fragment contained in the pharmaceutical composition of the present invention can also include a Fab fragment resulting from the posttranslational modification. Examples of the anti-human CEACAM5 antibody Fab fragment contained in the pharmaceutical composition of the present invention that can result from the posttranslational modification include an anti-human CEACAM5 antibody Fab fragment having an N-terminally pyroglutamylated heavy chain. It is known in the art that such a posttranslational modification by N-terminal pyroglutamylation has no marked influence on the activity of the antibody (Anal. Biochem., 2006; 348: 24-39).

In one embodiment, the anti-human CEACAM5 antibody Fab fragment contained in the pharmaceutical composition of the present invention is an anti-human CEACAM5 antibody Fab fragment having the following feature:
an anti-human CEACAM5 antibody Fab fragment comprising a heavy chain fragment comprising a heavy chain variable region derived from a heavy chain variable region consisting of an amino acid sequence from amino acid positions 1 to 121 of SEQ ID NO: 2 by the modification of glutamic acid at amino acid position 1 of SEQ ID NO: 2 into pyroglutamic acid, and a light chain comprising a light chain variable region consisting of an amino acid sequence from amino acid positions 1 to 112 of SEQ ID NO: 4.

In another embodiment, the anti-human CEACAM5 antibody Fab fragment contained in the pharmaceutical composition of the present invention is an anti-human CEACAM5 antibody Fab fragment having the following feature:
an anti-human CEACAM5 antibody Fab fragment comprising a heavy chain fragment derived from a heavy chain fragment consisting of the amino acid sequence represented by SEQ ID NO: 2 by the modification of glutamic acid at amino acid position 1 of SEQ ID NO: 2 into pyroglutamic acid, and a light chain consisting of the amino acid sequence represented by SEQ ID NO: 4.

The pharmaceutical composition of the present invention also includes an anti-human CEACAM5 antibody Fab fragment having the following feature:

an anti-human CEACAM5 antibody Fab fragment comprising a heavy chain fragment comprising a heavy chain variable region comprising CDR1 consisting of an amino acid sequence from amino acid positions 31 to 35 of SEQ ID NO: 2, CDR2 consisting of an amino acid sequence from amino acid positions 50 to 66 of SEQ ID NO: 2, and CDR3 consisting of an amino acid sequence from amino acid positions 99 to 110 of SEQ ID NO: 2, and a light chain comprising a light chain variable region comprising CDR1 consisting of an amino acid sequence from amino acid positions 24 to 38 of SEQ ID NO: 4, CDR2 consisting of an amino acid sequence from amino acid positions 54 to 60 of SEQ ID NO: 4, and CDR3 consisting of an amino acid sequence from amino acid positions 93 to 101 of SEQ ID NO: 4.

The anti-human CEACAM5 antibody Fab fragment contained in the pharmaceutical composition of the present invention binds to human CEACAM5. A method for measuring the binding activity of the obtained anti-human CEACAM5 antibody Fab fragment against human CEACAM5 includes methods such as analysis by surface plasmon resonance (SPR) and ELISA. In the case of using, for example, analysis by SPR, an association rate constant (ka), a dissociation rate constant (kd), and a dissociation constant ($K_D$) can be measured by using Biacore T200 (GE Healthcare Japan Corp.), immobilizing Biotin CAPture Kit (GE Healthcare Japan Corp.) and biotinylated human CEACAM5 onto a sensor chip, and adding a serially diluted Fab fragment thereto.

The anti-human CEACAM5 antibody Fab fragment contained in the pharmaceutical composition of the present invention can be readily prepared by those skilled in the art using a method known in the art on the basis of sequence information on the heavy chain fragment and the light chain of the anti-human CEACAM5 antibody Fab fragment contained in the pharmaceutical composition of the present invention disclosed herein. The anti-human CEACAM5 antibody Fab fragment contained in the pharmaceutical composition of the present invention can be produced according to, but not particularly limited to, a method described in, for example, <4-4. Method for producing anti-human antibody Fab fragment> mentioned later.

1-1-2. Anti-Human MUC1 Antibody Fab Fragment

Mucin 1 (MUC1) is a membrane-bound glycoprotein that is expressed on the lumen side of epithelial cells constituting the epithelial tissues of the mammary gland, the trachea and the gastrointestinal tract, etc. (Nat. Rev. Cancer, 2004 January; 4 (1): 45-60). MUC1 is overexpressed in cancer cells of breast cancer and colorectal cancer (Mod. Pathol.; 2005 October; 18 (10): 1295-1304, Int. J. Oncol.; 2000 January; 16 (1): 55-64). MUC1 is useful as a target molecule for detecting a cancer focus (Nat. Rev. Cancer; 2004 January; 4 (1): 45-60; and Pathol. Res. Pract.; 2010 Aug. 15; 206 (8): 585-9).

The anti-human MUC1 antibody Fab fragment contained in the pharmaceutical composition of the present invention is a Fab fragment having the following feature:

an anti-human MUC1 antibody Fab fragment comprising a heavy chain fragment comprising a heavy chain variable region consisting of the amino acid sequence represented by SEQ ID NO: 12 or SEQ ID NO: 14 and a light chain comprising a light chain variable region consisting of the amino acid sequence represented by SEQ ID NO: 16.

In one embodiment, the anti-human MUC1 antibody Fab fragment contained in the pharmaceutical composition of the present invention is an anti-human MUC1 antibody Fab fragment comprising a heavy chain fragment comprising a heavy chain variable region consisting of the amino acid sequence represented by SEQ ID NO: 14 and a light chain comprising a light chain variable region consisting of the amino acid sequence represented by SEQ ID NO: 16.

Any constant region of Igγ1, Igγ2, Igγ3 or Igγ4, etc. can be selectable as the heavy chain constant region of the anti-human MUC1 antibody Fab fragment contained in the pharmaceutical composition of the present invention. In one embodiment, the heavy chain constant region of the anti-human MUC1 antibody Fab fragment contained in the pharmaceutical composition of the present invention is a human Igγ1 constant region.

Any constant region of Igλ, or Igκ can be selectable as the light chain constant region of the anti-human MUC1 antibody Fab fragment contained in the pharmaceutical composition of the present invention. In one embodiment, the light chain constant region of the anti-human MUC1 antibody Fab fragment contained in the pharmaceutical composition of the present invention is a human Igκ constant region.

In one embodiment, the anti-human MUC1 antibody Fab fragment contained in the pharmaceutical composition of the present invention is the following Fab fragment:

an anti-human MUC1 antibody Fab fragment comprising a heavy chain fragment consisting of the amino acid sequence represented by SEQ ID NO: 6 or SEQ ID NO: 8 and a light chain consisting of the amino acid sequence represented by SEQ ID NO: 10.

In one embodiment, the anti-human MUC1 antibody Fab fragment contained in the pharmaceutical composition of the present invention is an anti-human MUC1 antibody Fab fragment comprising a heavy chain fragment consisting of the amino acid sequence represented by SEQ ID NO: 8 and a light chain consisting of the amino acid sequence represented by SEQ ID NO: 10.

In the case of expressing an antibody comprising a Fab fragment in cells, the antibody is known to undergo a posttranslational modification as described above. Thus, the anti-human MUC1 antibody Fab fragment contained in the pharmaceutical composition of the present invention can also include a Fab fragment resulting from the posttranslational modification. Examples of the anti-human MUC1 antibody Fab fragment contained in the pharmaceutical composition of the present invention resulting from the posttranslational modification include an anti-human MUC1 antibody Fab fragment having an N-terminally pyroglutamylated heavy chain. It is known in the art that such a posttranslational modification by N-terminal pyroglutamylation has no influence on the activity of the antibody as described above.

In one embodiment, the anti-human MUC1 antibody Fab fragment contained in the pharmaceutical composition of the present invention is an anti-human MUC1 antibody Fab fragment having the following feature:

an anti-human MUC1 antibody Fab fragment comprising a heavy chain fragment comprising a heavy chain variable region derived from a heavy chain variable region consisting of the amino acid sequence represented by SEQ ID NO: 12 or SEQ ID NO: 14 by the modification of glutamine at amino acid position 1 of SEQ ID NO: 12 or SEQ ID NO: 14 into pyroglutamic acid, and a light chain comprising a light chain variable region consisting of the amino acid sequence represented by SEQ ID NO: 16.

In a certain embodiment, the anti-human MUC1 antibody Fab fragment contained in the pharmaceutical composition of the present invention is an anti-human MUC1 antibody Fab fragment having the following feature:

an anti-human MUC1 antibody Fab fragment comprising a heavy chain fragment comprising a heavy chain variable region derived from a heavy chain variable region consisting of the amino acid sequence represented by SEQ ID NO: 14 by the modification of glutamine at amino acid position 1 of SEQ ID NO: 14 into pyroglutamic acid, and a light chain comprising a light chain variable region consisting of the amino acid sequence represented by SEQ ID NO: 16.

In an alternative embodiment, the anti-MUC1 antibody Fab fragment contained in the pharmaceutical composition of the present invention is an anti-human MUC1 antibody Fab fragment having the following feature:

an anti-human MUC1 antibody Fab fragment comprising a heavy chain fragment derived from a heavy chain fragment consisting of the amino acid sequence represented by SEQ ID NO: 6 or SEQ ID NO: 8 by the modification of glutamine at amino acid position 1 of SEQ ID NO: 6 or SEQ ID NO: 8 into pyroglutamic acid, and a light chain consisting of the amino acid sequence represented by SEQ ID NO: 10.

In a certain embodiment, the anti-MUC1 antibody Fab fragment contained in the pharmaceutical composition of the present invention is an anti-human MUC1 antibody Fab fragment having the following feature:

an anti-human MUC1 antibody Fab fragment comprising a heavy chain fragment derived from a heavy chain fragment consisting of the amino acid sequence represented by SEQ ID NO: 8 by the modification of glutamine at amino acid position 1 of SEQ ID NO: 8 into pyroglutamic acid, and a light chain consisting of the amino acid sequence represented by SEQ ID NO: 10.

The anti-human MUC1 antibody Fab fragment contained in the pharmaceutical composition of the present invention binds to human cancer-specific MUC1. A method for measuring the binding activity of the obtained anti-human MUC1 antibody Fab fragment against human cancer-specific MUC1 includes methods such as ELISA and FACS. In the case of using, for example, ELISA, human cancer-specific MUC1-positive cells (e.g., T-47D cells) are immobilized onto an ELISA plate, to which the Fab fragment is then added and reacted, and then, an anti-Igκ antibody or the like labeled with horseradish peroxidase or the like is reacted. Then, the binding of the secondary antibody is identified by activity measurement using a reagent for detecting the activity thereof (e.g., a chemiluminescent horseradish peroxidase substrate for the horseradish peroxidase label) or the like.

The anti-human MUC1 antibody Fab fragment contained in the pharmaceutical composition of the present invention can be readily prepared by those skilled in the art using a method known in the art on the basis of sequence information on the heavy chain fragment and the light chain of the anti-human MUC1 antibody Fab fragment contained in the pharmaceutical composition of the present invention disclosed herein. The anti-human MUC1 antibody Fab fragment contained in the pharmaceutical composition of the present invention can be produced according to, but not particularly limited to, a method described in, for example, <4-4. Method for producing anti-human antibody Fab fragment> mentioned later.

1-2. Labeling Moiety 1-2-1. Labeling Moiety Comprising Ligand

In a certain embodiment, the labeling moiety-anti-human antibody Fab fragment conjugate contained in the pharmaceutical composition of the present invention is a conjugate in which the labeling moiety is a ligand and a linker. In the present description, the "ligand" is a moiety capable of forming a chelate complex with a metal in the conjugate and means a group constituted by a chelating agent. The "constituted group" is a group having a bond by the removal of a proton from the chelating agent. The "chelating agent" is a compound that can form a coordinate bond with a metal.

In a certain embodiment, examples of the chelating agent constituting the ligand include siderophore and non-siderophore when the labeling moiety of the labeling moiety-anti-human antibody Fab fragment conjugate contained in the pharmaceutical composition of the present invention is a ligand and a linker. Examples of a certain embodiment include MAG3 (mercaptoacetyl-glycyl-glycyl-glycine, CAS No: 66516-09-4) and known reactive derivatives thereof. Examples of the siderophore include hydroxamic acid type, catechol type, and mixed ligand type. Examples of the hydroxamic acid-type siderophore include ferrichrome, deferoxamine (DFO) represented by the following formula:

[Chemical Formula 4]

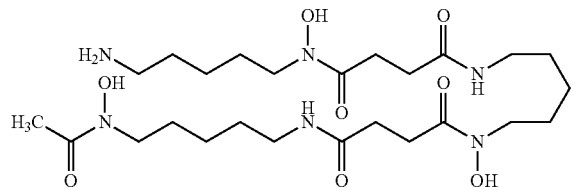

fusarinine C, ornibactin, rhodotorulic acid, and known reactive derivatives thereof. Examples of the catechol-type siderophore include enterobactin, bacillibactin, vibriobactin, and known reactive derivatives thereof. Examples of the mixed ligand-type siderophore include azotobactin, pyoverdine, yersiniabactin, and known reactive derivatives thereof. In the case of the siderophore, DFO can be reacted via its reactive functional group —$NH_2$ with the linker or the Fab fragment, and the siderophore other than DFO can also be reacted via its reactive functional group such as a carboxy group, a hydroxy group, or an amino group with the linker or the Fab fragment by a method usually used by those skilled in the art.

Examples of the non-siderophore include DTPA (diethylenetriaminepentaacetic acid, CAS No: 67-43-6), DTPA-BMA (1,7-bis(methylcarbamoylmethyl)-1,4,7-triazaheptane-1,4,7-triacetic acid, CAS No: 119895-95-3), EOB-DTPA (ethoxybenzyl-DTPA, 2-[[(2S)-2-[bis(carboxymethyl)amino]-3-(4-ethoxyphenyl)propyl]-[2-[bis(carboxymethyl)amino]ethyl]amino]acetic acid), TTHA (triethylenetetraminehexaacetic acid, CAS No: 869-52-3), DO3A (1,4,7,10-tetraazacyclododecane-1,4,7-triacetic acid, CAS No: 217973-03-0), HP-DO3A (10-(2-hydroxypropyl)-1,4,7,10-tetraazacyclododecane-1,4,7-triacetic acid, CAS No: 120041-08-9), DOTA (1,4,7,10-tetraazacyclododecane-1,4,7,10-tetraacetic acid, CAS No: 60239-18-1), and known reactive derivatives thereof.

When the labeling moiety of the labeling moiety-anti-human antibody Fab fragment conjugate contained in the pharmaceutical composition of the present invention is a ligand and a linker, the "chelating agent" constituting the ligand is preferably DFO.

The "linker is a group that creates a distance between the anti-human antibody Fab fragment and the ligand. In a certain embodiment, when the labeling moiety of the labeling moiety-anti-human antibody Fab fragment conjugate contained in the pharmaceutical composition of the present invention is a ligand and a linker, examples of the linker that creates a distance between the anti-human antibody Fab fragment and the ligand include the following formula:

[Chemical Formula 5]

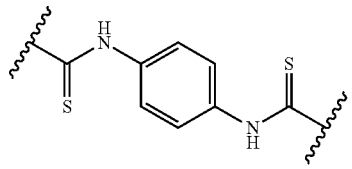

(hereinafter, designated as —C(=S)—NH-(1,4-phenylene)-NH—C(=S)—), —CH$_2$-(1,4-phenylene)-NH—C(=S)—, and —C(=O)—(C$_{1-20}$ alkylene)-C(=O)—. In this context, the "C$_{1-20}$ alkylene" is linear or branched alkylene having 1 to 20 carbon atoms. A certain embodiment of the C$_{1-20}$ alkylene is C$_{1-10}$ alkylene or C$_{1-2}$ alkylene. A certain embodiment of the C$_{1-20}$ alkylene is ethylene. Examples of a reagent that can be used for forming the linker include HO—C(=O)—(C$_{1-20}$ alkylene)-C(=O)—OH, succinic acid, and p-phenylene diisothiocyanate.

When the labeling moiety of the labeling moiety-anti-human antibody Fab fragment conjugate contained in the pharmaceutical composition of the present invention is a ligand and a linker, the "linker" is preferably —C(=S)—NH-(1,4-phenylene)-NH—C(=S)—.

When the labeling moiety is a ligand and a linker, the labeling moiety-anti-human antibody Fab fragment conjugate contained in the pharmaceutical composition of the present invention may be produced by reacting the chelating agent forming the ligand with a substance obtained through the reaction of the anti-human antibody Fab fragment with the linker. The conjugate may also be produced by reacting the anti-human antibody Fab fragment with a substance obtained through the reaction of the linker with the chelating agent forming the ligand. As a reaction example, a substance obtained through the reaction of the amino group of the chelating agent with the linker is reacted with one or more amino groups (e.g., an N-terminal amino group and an amino group of a lysine side chain) of the anti-human antibody Fab fragment. When the labeling moiety is a ligand, it may be produced by reacting the chelating agent forming the ligand with the anti-human antibody Fab fragment. As a reaction example, the chelating agent is reacted with one or more amino groups (e.g., an N-terminal amino group and an amino group of a lysine side chain) of the anti-human antibody Fab fragment. Reaction of synthesizing thiourea by adding isothiocyanate to amine, reaction of synthesizing amide by adding carboxylic acid to amine, or the like can be used in the production of the labeling moiety-anti-human antibody Fab fragment conjugate contained in the pharmaceutical composition of the present invention. The reaction can be performed by the application of a method known to those skilled in the art. A compound of the ligand bound to the linker in advance may be used as a starting material. Examples of the compound of the ligand bound to the linker include p-SCN-Bn-DFO (DFO substituted by a p-isothiocyanophenylaminothiocarbonyl group, CAS No: 1222468-90-7) represented by the following formula:

[Chemical Formula 6]

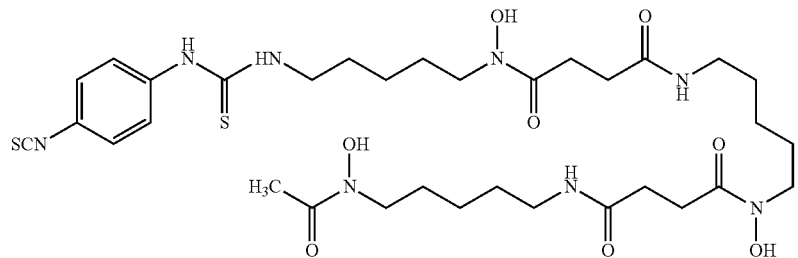

DTPA substituted by a p-isothiocyanobenzyl group (p-SCN-Bn-DTPA, CAS No: 102650-30-6), DOTA substituted by a p-isothiocyanobenzyl group (p-SCN-Bn-DOTA, CAS No: 127985-74-4), and p-SCN-Bn-CHX-A"-DTPA ([(R)-2-amino-3-(4-isothiocyanatophenyl)propyl]-trans-(S,S)-cyclohexane-1,2-diamine-pentaacetic acid, CAS No: 157380-45-5).

In a certain embodiment, the labeling moiety-anti-human antibody Fab fragment conjugate contained in the pharmaceutical composition of the present invention is a conjugate in which the labeling moiety is a ligand and a linker represented by the following formula (I):

[Chemical Formula 7]

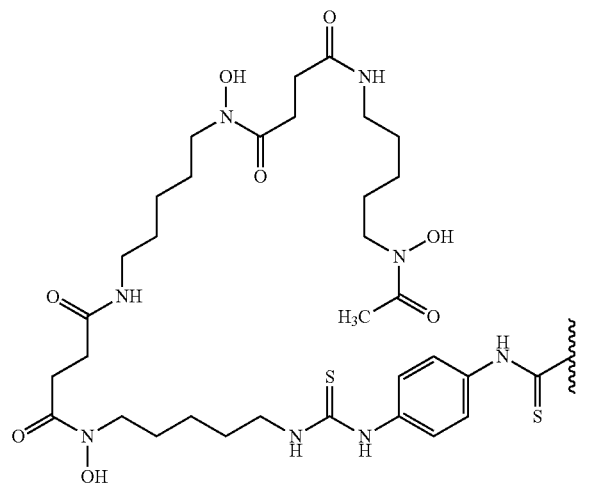

(I)

wherein the wavy line represents binding to the anti-human antibody Fab fragment, where the anti-human antibody Fab fragment is bound to the carbon atom of a labeling moiety terminal C(=S) group via an amino group in the anti-human antibody Fab fragment.

As described above, when the labeling moiety of the labeling moiety-anti-human antibody Fab fragment conjugate contained in the pharmaceutical composition of the present invention is a ligand and a linker, the chelating agent constituting the ligand can form a chelating complex with a metal radioisotope. In the present description, the metal radioisotope is, for example, one that is used for a PET tracer etc., and examples thereof include $^{89}$Zr, $^{51}$Mn, $^{52}$Fe, $^{60}$Cu, $^{67}$Ga, $^{68}$Ga, $^{72}$As, $^{99m}$Tc, and $^{111}$In. $^{89}$Zr is preferable. That is, the labeling moiety-anti-human antibody Fab fragment conjugate contained in the pharmaceutical composition of the present invention may be free of a metal radioisotope, or may contain $^{89}$Zr as a metal radioisotope.

As for a form in which the pharmaceutical composition of the present invention is provided, it may be provided in a form free of a metal radioisotope, and labeled with the metal radioisotope immediately before use, or may be provided as a metal radioisotope-containing pharmaceutical composition used for diagnosis. For example, in the case of using a metal radioisotope with a short half-life (e.g. $^{89}$Zr (half-life: 3.3 days)), it is preferable that the composition be provided in a form free of the metal radioisotope, and labeled with the metal radioisotope immediately before use.

1-2-2. Labeling Moiety Comprising Fluorescent Dye

In a certain embodiment, when the labeling moiety of the labeling moiety-anti-human antibody Fab fragment conjugate contained in the pharmaceutical composition of the present invention is a fluorescent dye, a dye having absorption maximum and emission maximum at a near-infrared wavelength (650 to 1000 nm) usually used in photoimaging can be used as the fluorescent dye. Examples of a certain embodiment of the fluorescent dye include cyanine and indocyanine compounds. Examples of a certain embodiment include IRDye800CW (LI-COR, Inc.), Cy (Molecular Probes, Inc.), Alexa Fluor, BODIPY, and DyLight (Thermo Fisher Scientific Inc.), CF790 (Biotium, Inc.), DY (Dyomics GmbH), HiLyte Fluor 680 and HiLyte Fluor 750 (AnaSpec Inc.), and PULSAR650 and QUASAR670 (LGC Biosearch Technologies).

When the labeling moiety of the labeling moiety-anti-human antibody Fab fragment conjugate contained in the pharmaceutical composition of the present invention is a fluorescent dye, the fluorescent dye is preferably IRDye800CW (LI-COR Biosciences) represented by the following formula:

[Chemical Formula 8]

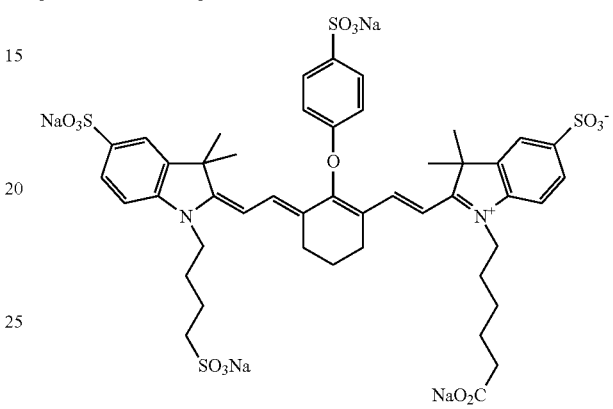

The fluorescent dye can be reacted via its carboxy group, hydroxy group, amino group, or the like or via an active group introduced by a method usually used by those skilled in the art with the anti-human antibody Fab fragment or the linker bound to the anti-human antibody Fab fragment. A certain embodiment of the fluorescent dye having an introduced active group is a fluorescent dye esterified with a N-hydroxysuccinimide (NHS) group. For example, NHS esters of IRDye800CW are commercially available, and they can be utilized.

In a certain embodiment, the labeling moiety-anti-human antibody Fab fragment conjugate contained in the pharmaceutical composition of the present invention is a conjugate in which the labeling moiety is a fluorescent dye represented by the following formula (II):

[Chemical Formula 9]

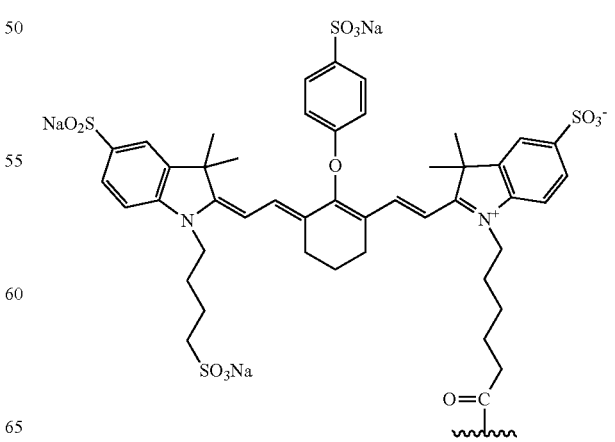

(II)

wherein the wavy line represents binding to the anti-human antibody Fab fragment, where the anti-human antibody Fab fragment is bound to the carbon atom of a labeling moiety terminal C(=O) group via an amino group in the anti-human antibody Fab fragment.

In the labeling moiety-anti-human antibody Fab fragment conjugate contained in the pharmaceutical composition, the binding of the anti-human antibody Fab fragment to the labeling moiety can be appropriately performed by those skilled in the art using a known approach. For example, the labeling moiety can be bound to one or more amino groups (e.g., an N-terminal amino group and an amino group of an amino acid side chain), one or more thiol groups (e.g., a thiol group of an amino acid side chain), or one or more carboxyl groups (e.g., carboxyl groups of the C terminus and an amino acid side chain) of the anti-human antibody Fab fragment. A certain embodiment of the labeling moiety-anti-human antibody Fab fragment conjugate contained in the pharmaceutical composition of the present invention is a conjugate in which the labeling moiety is bound to one or more amino groups of the anti-human antibody Fab fragment.

1-3. Labeling Moiety-Anti-Human Antibody Fab Fragment Conjugate

The pharmaceutical composition of the present invention comprises a labeling moiety-anti-human antibody Fab fragment conjugate. A certain embodiment of the labeling moiety-anti-human antibody Fab fragment conjugate contained in the pharmaceutical composition of the present invention is a labeling moiety-anti-human CEACAM5 antibody Fab fragment conjugate in which the anti-human antibody Fab fragment is one or more selected from the group consisting of the following (a) and (b):

(a) an anti-human CEACAM5 antibody Fab fragment comprising a heavy chain fragment comprising a heavy chain variable region consisting of an amino acid sequence from amino acid positions 1 to 121 of SEQ ID NO: 2 and a light chain comprising a light chain variable region consisting of an amino acid sequence from amino acid positions 1 to 112 of SEQ ID NO: 4; and (b) an anti-human CEACAM5 antibody Fab fragment comprising a heavy chain fragment comprising a heavy chain variable region derived from a heavy chain variable region consisting of an amino acid sequence from amino acid positions 1 to 121 of SEQ ID NO: 2 by the modification of glutamic acid at amino acid position 1 of SEQ ID NO: 2 into pyroglutamic acid, and a light chain comprising a light chain variable region consisting of an amino acid sequence from amino acid positions 1 to 112 of SEQ ID NO: 4, and the labeling moiety is a group represented by the following formula (I):

[Chemical Formula 10]

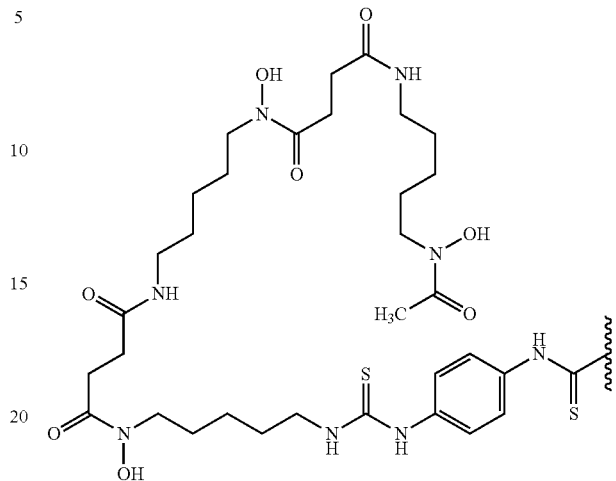

(I)

wherein the wavy line represents binding to the anti-human CEACAM5 antibody Fab fragment, where the anti-human CEACAM5 antibody Fab fragment is bound to the carbon atom of a labeling moiety terminal C(=S) group via an amino group in the anti-human CEACAM5 antibody Fab fragment.

A certain embodiment of the anti-human CEACAM5 antibody Fab fragment contained in the labeling moiety-anti-human antibody Fab fragment conjugate is one or more selected from the group consisting of the following (a) and (b):

(a) an anti-human CEACAM5 antibody Fab fragment comprising a heavy chain fragment consisting of the amino acid sequence represented by SEQ ID NO: 2 and a light chain consisting of the amino acid sequence represented by SEQ ID NO: 4; and (b) an anti-human CEACAM5 antibody Fab fragment comprising a heavy chain fragment derived from a heavy chain fragment consisting of the amino acid sequence represented by SEQ ID NO: 2 by the modification of glutamic acid at amino acid position 1 of SEQ ID NO: 2 into pyroglutamic acid, and a light chain consisting of the amino acid sequence represented by SEQ ID NO: 4.

A certain embodiment of the labeling moiety-anti-human antibody Fab fragment conjugate contained in the pharmaceutical composition of the present invention is a labeling moiety-anti-human MUC1 antibody Fab fragment conjugate in which the anti-human antibody Fab fragment is one or more selected from the group consisting of the following (a) and (b):

(a) an anti-human MUC1 antibody Fab fragment comprising a heavy chain fragment comprising a heavy chain variable region consisting of the amino acid sequence represented by SEQ ID NO: 12 or SEQ ID NO: 14 and a light chain comprising a light chain variable region consisting of the amino acid sequence represented by SEQ ID NO: 16; and (b) an anti-human MUC1 antibody Fab fragment comprising a heavy chain fragment comprising a heavy chain variable region derived from a heavy chain variable region consisting of the amino acid sequence represented by SEQ ID NO: 12 or SEQ ID NO: 14 by the modification of glutamine at amino acid position 1 of SEQ ID NO: 12 or SEQ ID NO: 14 into pyroglutamic acid, and a light chain comprising a light chain variable region consisting of the amino acid sequence represented by SEQ ID NO: 16, and the labeling moiety is a group represented by the following formula (I):

[Chemical Formula 11]

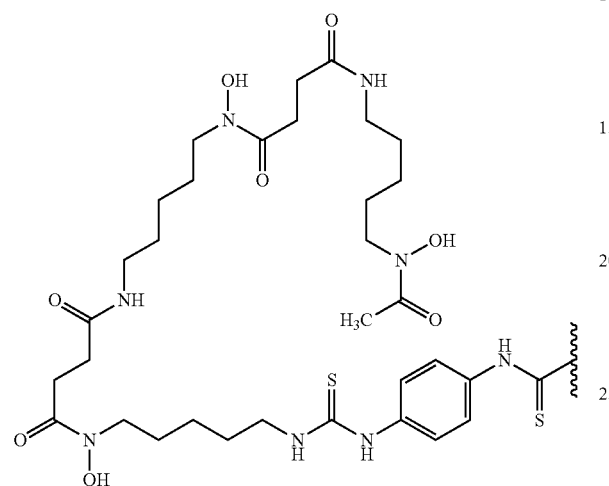

(I)

wherein the wavy line represents binding to the anti-human MUC1 antibody Fab fragment, where the anti-human MUC1 antibody Fab fragment is bound to the carbon atom of a labeling moiety terminal C(=S) group via an amino group in the anti-human MUC1 antibody Fab fragment.

A certain embodiment of the anti-human MUC1 antibody Fab fragment contained in the labeling moiety-anti-human antibody Fab fragment conjugate is one or more selected from the group consisting of the following (a) and (b):

(a) an anti-human MUC1 antibody Fab fragment comprising a heavy chain fragment consisting of the amino acid sequence represented by SEQ ID NO: 6 or SEQ ID NO: 8 and a light chain consisting of the amino acid sequence represented by SEQ ID NO: 10; and (b) an anti-human MUC1 antibody Fab fragment comprising a heavy chain fragment derived from a heavy chain fragment consisting of the amino acid sequence represented by SEQ ID NO: 6 or SEQ ID NO: 8 by the modification of glutamine at amino acid position 1 of SEQ ID NO: 6 or SEQ ID NO: 8 into pyroglutamic acid, and a light chain consisting of the amino acid sequence represented by SEQ ID NO: 10.

A certain embodiment of the labeling moiety-anti-human antibody Fab fragment conjugate contained in the pharmaceutical composition of the present invention is a labeling moiety-anti-human MUC1 antibody Fab fragment conjugate in which the anti-human antibody Fab fragment is one or more selected from the group consisting of the following (a) and (b):

(a) an anti-human MUC1 antibody Fab fragment comprising a heavy chain fragment comprising a heavy chain variable region consisting of the amino acid sequence represented by SEQ ID NO: 12 or SEQ ID NO: 14 and a light chain comprising a light chain variable region consisting of the amino acid sequence represented by SEQ ID NO: 16; and (b) an anti-human MUC1 antibody Fab fragment comprising a heavy chain fragment comprising a heavy chain variable region derived from a heavy chain variable region consisting of the amino acid sequence represented by SEQ ID NO: 12 or SEQ ID NO: 14 by the modification of glutamine at amino acid position 1 of SEQ ID NO: 12 or SEQ ID NO: 14 into pyroglutamic acid, and a light chain comprising a light chain variable region consisting of the amino acid sequence represented by SEQ ID NO: 16, and the labeling moiety is a group represented by the following formula (II):

[Chemical Formula 12]

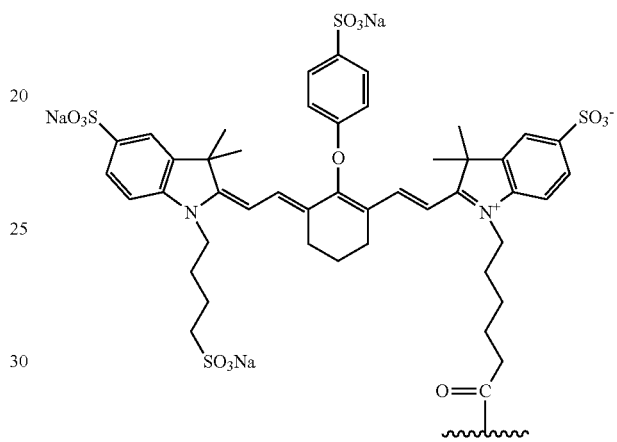

(II)

wherein the wavy line represents binding to the anti-human MUC1 antibody Fab fragment, where the anti-human MUC1 antibody Fab fragment is bound to the carbon atom of a labeling moiety terminal C(=O) group via an amino group in the anti-human MUC1 antibody Fab fragment.

A certain embodiment of the anti-human MUC1 antibody Fab fragment contained in the labeling moiety-anti-human antibody Fab fragment conjugate is one or more selected from the group consisting of the following (a) and (b):

(a) an anti-human MUC1 antibody Fab fragment comprising a heavy chain fragment consisting of the amino acid sequence represented by SEQ ID NO: 6 or SEQ ID NO: 8 and a light chain consisting of the amino acid sequence represented by SEQ ID NO: 10; and (b) an anti-human MUC1 antibody Fab fragment comprising a heavy chain fragment derived from a heavy chain fragment consisting of the amino acid sequence represented by SEQ ID NO: 6 or SEQ ID NO: 8 by the modification of glutamine at amino acid position 1 of SEQ ID NO: 6 or SEQ ID NO: 8 into pyroglutamic acid, and a light chain consisting of the amino acid sequence represented by SEQ ID NO: 10.

The labeling moiety-anti-human CEACAM5 antibody Fab fragment conjugate contained in the pharmaceutical composition of the present invention is a conjugate in which one or more labeling moieties are bound to the anti-human CEACAM5 antibody Fab fragment. A certain embodiment of the labeling moiety-anti-human CEACAM5 antibody Fab fragment conjugate contained in the pharmaceutical composition of the present invention is the anti-human CEACAM5 antibody Fab fragment bound to 1 to 25 labeling moieties. A certain embodiment is the anti-human CEACAM5 antibody Fab fragment bound to 1 to 23 labeling moieties. A certain embodiment is the anti-human CEACAM5 antibody Fab fragment bound to 1 to 16 labeling moieties. A certain embodiment is the anti-human CEACAM5 antibody Fab fragment bound to 1 to 11 labeling moieties. A certain embodiment is the anti-human CEACAM5 antibody Fab fragment bound to 1 to 10 labeling moieties. A certain embodiment is the anti-human CEACAM5 antibody Fab fragment bound to 1 to 9 labeling moieties. A certain embodiment is the anti-human CEACAM5 antibody Fab fragment bound to 4 to 23 labeling moieties. A certain embodiment is the anti-human CEACAM5 antibody Fab fragment bound to 4 to 16 labeling moieties. A certain embodiment is the anti-human CEACAM5 antibody Fab fragment bound to 4 to 10 labeling moieties. A certain embodiment is the anti-human CEACAM5 antibody Fab fragment bound to 4 to 9 labeling moieties. A certain embodiment is the anti-human CEACAM5 antibody Fab fragment bound to 3 to 23 labeling moieties. A certain embodiment is the anti-human CEACAM5 antibody Fab fragment bound to 3 to 16 labeling moieties. A certain embodiment is the anti-human CEACAM5 antibody Fab fragment bound to 3 to 10 labeling moieties. A certain embodiment is the anti-human CEACAM5 antibody Fab fragment bound to 3 to 9 labeling moieties. A certain embodiment is the anti-human CEACAM5 antibody Fab fragment bound to at least one labeling moieties further comprising a metal.

The conjugate contained in the pharmaceutical composition of the present invention is a conjugate comprising one or more labeling moieties and an anti-human MUC1 antibody Fab fragment. A certain embodiment is the anti-human MUC1 antibody Fab fragment bound to 1 to 27 labeling moieties. A certain embodiment is the anti-human MUC1 antibody Fab fragment bound to 1 to 23 labeling moieties. A certain embodiment is the anti-human MUC1 antibody Fab fragment bound to 1 to 15 labeling moieties. A certain embodiment is the anti-human MUC1 antibody Fab fragment bound to 1 to 11 labeling moieties. A certain embodiment is the anti-human MUC1 antibody Fab fragment bound to 1 to 9 labeling moieties. A certain embodiment is the anti-human MUC1 antibody Fab fragment bound to 1 to 7 labeling moieties. A certain embodiment is the anti-human MUC1 antibody Fab fragment bound to 1 to 5 labeling moieties. A certain embodiment is the anti-human MUC1 antibody Fab fragment bound to 1 to 4 labeling moieties. A certain embodiment is the anti-human MUC1 antibody Fab fragment bound to at least one labeling moiety further comprising a metal.

The labeling moiety-anti-human antibody Fab fragment conjugate contained in the pharmaceutical composition of the present invention encompasses free forms and salts thereof unless otherwise specified. In this context, the "salt thereof" is a salt that can be formed by the compound or the conjugate that may form an acid-addition salt or a salt with a base depending on the type of a substituent in the conjugate. Specific examples thereof include: acid-addition salts with inorganic acids such as hydrochloric acid, hydrobromic acid, hydroiodic acid, sulfuric acid, nitric acid, and phosphoric acid, or organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid, and glutamic acid; salts with inorganic bases such as sodium, potassium, magnesium, calcium, and aluminum, or organic bases such as methylamine, ethylamine, ethanolamine, lysine, and ornithine; salts with various amino acids and amino acid derivatives, such as acetylleucine; and ammonium salts. For example, DFO exists as deferoxamine methanesulfonate or exists as other salts.

The concentration of the labeling moiety-anti-human antibody Fab fragment conjugate in the pharmaceutical composition of the present invention is not particularly limited as long as it is a concentration allowing diagnostically or therapeutically effective action to be exhibited, and the concentration is preferably 1 to 100 mg/mL, more preferably 5 to 20 mg/mL.

1-4. Buffering Agent

As a buffering agent in the pharmaceutical composition of the present invention, citric acid, phosphoric acid, 2-[4-(2-hydroxyethyl)-1-piperazinyl]ethanesulfonic acid or trishydroxymethyl aminomethane can be used from the viewpoint of maintaining a pH in a range as described below to suppress impacts on coordination efficiency of a metal radioisotope to a ligand. The concentration of the buffering agent in the pharmaceutical composition of the present invention differs depending on the type of the buffering agent and a target pH, and is preferably 10 to 30 mmol/L.

A certain embodiment of the buffering agent in the pharmaceutical composition of the present invention is citric acid, and the concentration thereof is 10 to 30 mmol/L, preferably 15 to 25 mmol/L. A certain embodiment of the buffering agent in the pharmaceutical composition of the present invention is phosphoric acid, and the concentration thereof is 10 to 30 mmol/L, preferably 15 to 25 mmol/L.

1-5. Stabilizer

As a stabilizer in the pharmaceutical composition of the present invention, sucrose or glycerin can be used from the viewpoint of suppressing generation of multimers, acidic charge variants or insoluble subvisible particles due to heat stress, light stress, shaking stress, or the like during preservation, and also suppressing a decrease in coordination efficiency of a metal radioisotope to a ligand and fluorescent dye color degradation. The concentration of the stabilizer in the pharmaceutical composition of the present invention differs depending on the type of a stabilizer used, and is preferably 5 to 30 w/v %.

A certain embodiment of the stabilizer in the pharmaceutical composition of the present invention is sucrose, and the concentration thereof is 5 to 30 w/v %, preferably 15 to 25 w/v %. A certain embodiment of the buffering agent in the pharmaceutical composition of the present invention is glycerin, and the concentration thereof is 5 to 30 w/v %, preferably 15 to 25 w/v %.

1-6. Nonionic Surfactant

In the pharmaceutical composition of the present invention, a nonionic surfactant can be used. As the nonionic surfactant in the pharmaceutical composition of the present invention, Polysorbate 80, Polysorbate 20, Polysorbate 60 or Poloxamer 188 can be used from the viewpoint of suppressing generation of insoluble subvisible particles, and also suppressing a decrease in coordination efficiency of a metal radioisotope to a ligand and fluorescent dye color degradation. The Polysorbate 80, which is also called polyoxyethylene (20) sorbitan oleic acid ester, is a polyoxyethylene ether of anhydrous sorbitol having some of hydroxyl groups esterified with oleic acid, and has a structure in which about 20 moles of ethylene oxide groups are ether-bonded to 1 mole of sorbitan monooleate. The concentration of the nonionic surfactant in the pharmaceutical composition of the present invention differs depending on the type thereof, and is preferably 0.02 to 0.2 w/v %.

A certain embodiment of the nonionic surfactant in the pharmaceutical composition of the present invention is Polysorbate 80, and the concentration thereof is 0.02 to 0.2 w/v %, preferably 0.04 to 0.1 w/v %.

1-7. pH

In the pharmaceutical composition of the present invention, the pH is 6.5 to 7.5, more preferably 6.5 to 7.0, from the viewpoint of suppressing generation of multimers, acidic charge variants or insoluble subvisible particles due to heat stress, light stress, shaking stress, or the like during preservation, and also suppressing a decrease in coordination efficiency of a metal radioisotope to a ligand and fluorescent dye color degradation.

A preferred form of the pharmaceutical composition of the present invention comprises the anti-human CEACAM5 antibody Fab fragment conjugate or anti-human MUC1 antibody Fab fragment mentioned above at a concentration of 5 to 20 mg/mL as a labeling moiety-anti-human antibody Fab fragment conjugate, citric acid at 15 to 25 mmol/L as a buffering agent, sucrose at 15 to 25 w/v % as a stabilizer, and Polysorbate 80 at 0.04 to 0.1 w/v % as a nonionic surfactant, and has a pH of 6.5 to 7.0.

1-8. Pharmaceutical Composition for Use in Diagnosis

In a certain embodiment, the present invention relates to a pharmaceutical composition for use in diagnosis comprising a labeling moiety-anti-human antibody Fab fragment conjugate. When the labeling moiety-anti-human antibody Fab fragment conjugate contained in the pharmaceutical composition of the present invention comprises a ligand as a labeling moiety, coordination of a metal radioisotope (e.g. $^{89}$Zr) makes the conjugate detectable. When the labeling moiety-anti-human antibody Fab fragment conjugate contained in the pharmaceutical composition of the present invention comprises a fluorescent dye as a labeling moiety, the conjugate is a detectable conjugate. These detectable conjugates can be utilized as an early diagnostic drug, a staging drug or an intraoperative diagnostic drug (particularly a diagnostic drug for cancer). The intraoperative diagnostic drug means a diagnostic drug capable of identifying a lesion site and examining the property thereof during an operation such as a surgical operation or an endoscopic operation. When the pharmaceutical composition for use in diagnosis according to the present invention is used as an intraoperative diagnostic drug, the pharmaceutical composition for use in diagnosis is administered to the patient, for example, 2 to 32 hours before the operation, a certain embodiment of the pharmaceutical composition is administered to the patient 6 to 24 hours before the operation, and another form of the pharmaceutical composition is administered to the patient 2 hours before the operation.

The early diagnostic drug means a diagnostic drug aimed at making a diagnosis when a condition is not found or during an early disease state. For example, for cancers, the early diagnostic drug means a diagnostic drug which is used when a condition is not found or during stage 0 or stage 1.

The staging drug means a diagnostic drug capable of examining the degree of progression of a condition. For example, for cancers, it means a diagnostic drug capable of examining the stage thereof.

When the pharmaceutical composition of the present invention comprises the labeling moiety-anti-human CEACAM5 antibody Fab fragment conjugate, it can be used for diagnosing cancers expressing human CEACAM5. When the pharmaceutical composition of the present invention comprises the labeling moiety-anti-human CEACAM5 antibody Fab fragment conjugate, a certain embodiment thereof is preferably used for the pharmaceutical composition for diagnosing colorectal cancer, breast cancer, lung cancer, thyroid gland cancer or a cancer resulting from the metastasis thereof, and in particular, use for diagnosing colorectal cancer or a cancer resulting from the metastasis of colorectal cancer is preferable. The cancer resulting from the metastasis of colorectal cancer is not particularly limited, and examples thereof include metastatic liver cancer.

When the pharmaceutical composition of the present invention comprises the labeling moiety-anti-human MUC1 antibody Fab fragment conjugate, it can be used for diagnosing cancers expressing human MUC1. When the pharmaceutical composition of the present invention comprises the labeling moiety-anti-human MUC1 antibody Fab fragment conjugate, a certain embodiment thereof is preferably used for diagnosing breast cancer, lung cancer, colorectal cancer, bladder cancer, skin cancer, thyroid gland cancer, stomach cancer, pancreatic cancer, kidney cancer, ovary cancer or uterine cervical cancer, and in particular, use for diagnosing breast cancer or bladder cancer is preferable.

1-9. Dosage Form and Additives of Pharmaceutical Composition

The dosage form of the pharmaceutical composition of the present invention is not particularly limited, and a certain embodiment thereof is a liquid formulation, a frozen formulation or a lyophilized formulation. The pharmaceutical composition of the present invention can be used as, for example, a parenteral agent such as an injection or an agent for drip infusion, and administration is preferably performed by intravenous injection, local intramuscular injection to a target, subcutaneous injection, or the like. The dose of the detectable labeling moiety-anti-human antibody Fab fragment conjugate in the pharmaceutical composition of the present invention differs depending on the age or body weight of a patient, the dosage form of a formulation used, or the binding titer of the Fab fragment, etc. For example, approximately 0.001 mg/kg to 100 mg/kg based on the mass of the Fab fragment can be used per unit body weight of a patient.

To the pharmaceutical composition of the present invention, medicinal additives such as a suspension agent, a solubilizer, a tonicity agent, a preservative, an adsorption inhibitor, an excipient, a soothing agent, a sulfur-containing reducing agent and an antioxidant or the like can be appropriately added if desired.

Examples of the suspension agent include methylcellulose, hydroxyethylcellulose, gum arabic, powdered tragacanth, carboxymethylcellulose sodium, and polyoxyethylene sorbitan monolaurate or the like.

Examples of the solubilizer include polyoxyethylene hydrogenated castor oil, nicotinic amide, polyoxyethylene sorbitan monolaurate, macrogol, and castor oil fatty acid ethyl ester or the like.

Examples of the tonicity agent include sodium chloride, potassium chloride, calcium chloride or the like.

Examples of the preservative include methyl paraoxybenzoate, ethyl paraoxybenzoate, sorbic acid, phenol, cresol, chlorocresol, and benzyl alcohol or the like.

Examples of the adsorption inhibitor include human serum albumin, lecithin, dextran, ethylene oxide-propylene oxide copolymers, hydroxypropylcellulose, methylcellulose, polyoxyethylene hydrogenated castor oil, and polyethylene glycol or the like.

Examples of the excipient include xylitol or the like.

Examples of the soothing agent include inositol, and lidocaine or the like.

Examples of the sulfur-containing reducing agent include those having a sulfhydryl group, such as N-acetylcysteine, N-acetylhomocysteine, thioctic acid, thiodiglycol, thioethanolamine, thioglycerol, thiosorbitol, thioglycolic acid and salts thereof, sodium thiosulfate, glutathione, and thioalkanoic acid having 1 to 7 carbon atoms.

Examples of the antioxidant include erythorbic acid, dibutylhydroxytoluene, butylhydroxyanisole, α-tocopherol, tocopherol acetate, L-ascorbic acid and salts thereof, L-ascorbyl palmitate, L-ascorbyl stearate, sodium hydrogen sulfite, sodium sulfite, triamyl gallate, propyl gallate, and chelating agents such as disodium ethylenediaminetetraacetate (EDTA), sodium pyrophosphate and sodium metaphosphate.

2. Use of Pharmaceutical Composition for Use in Diagnosis and Diagnosis Method The present invention relates to use of the labeling moiety-anti-human antibody Fab fragment conjugate for producing a pharmaceutical composition for use in early diagnosis of a cancer, a pharmaceutical composition for use in staging or a pharmaceutical composition for use in intraoperative diagnosis. In a certain embodiment, the present invention provides a pharmaceutical composition comprising the labeling moiety-anti-human antibody Fab fragment conjugate, for use in early diagnosis, staging or intraoperative diagnosis of a cancer.

The present invention also relates to a method for diagnosing a cancer, comprising preoperatively or intraoperatively administering the pharmaceutical composition comprising the labeling moiety-anti-human antibody Fab fragment conjugate to a subject. In this context, the "subject" is a human or any of other mammals in need of receiving the diagnosis. A certain embodiment is a human in need of receiving the diagnosis. The effective amount of the pharmaceutical composition of the present invention comprising the labeling moiety-anti-human antibody Fab fragment conjugate in the diagnosis method differs depending on the age or body weight of a patient, the dosage form of a formulation used, or the binding titer of the Fab fragment, etc. For example, approximately 0.001 mg/kg to 100 mg/kg based on the mass of the Fab fragment may be used per unit body weight of a patient. In the diagnosis method, administration of the pharmaceutical composition of the present invention comprising the labeling moiety-anti-human antibody Fab fragment conjugate is preferably performed by local intramuscular injection to a target tissue, subcutaneous injection, or the like. In the case of preoperatively administering the pharmaceutical composition of the present invention in the diagnosis method, the conjugate is administered to the patient, for example, 2 to 48 hours before the operation, a certain embodiment of the conjugate is administered to the patient 6 to 24 hours before the operation, and another form of the conjugate is administered to the patient 2 hours before the operation.

In another embodiment, the present invention also relates to use of the labeling moiety-anti-human antibody Fab fragment conjugate for producing the pharmaceutical composition of the present invention.

3. Method for Producing Pharmaceutical Composition Comprising Labeling Moiety-Anti-Human Antibody Fab Fragment Conjugate and Method for Stably Preserving Labeling Moiety-Anti-Human Antibody Fab Fragment Conjugate In a certain embodiment, the present invention relates to a method for producing a pharmaceutical composition comprising a labeling moiety-anti-human antibody Fab fragment conjugate. Specifically, in a certain embodiment, the present invention provides a method for producing a pharmaceutical composition comprising a labeling moiety-anti-human antibody Fab fragment conjugate, comprising the steps of (a) producing and adding the labeling moiety-anti-human antibody Fab fragment conjugate; (b) adding citric acid, phosphoric acid, 2-[4-(2-hydroxyethyl)-1-piperazinyl]ethanesulfonic acid or trishydroxymethyl aminomethane as a buffering agent; (c) adding sucrose or glycerin as a stabilizer; (d) adding Polysorbate 80 as a nonionic surfactant; and (e) adjusting the pH to 6.5 to 7.5. The order of the addition is not particularly limited.

In a certain embodiment, the present invention relates to a method for stably preserving the labeling moiety-anti-human antibody Fab fragment conjugate. In the present description, the term "stably preserving" refers to suppression of generation of multimers or insoluble subvisible particles during preservation of the labeling moiety-anti-human antibody Fab fragment conjugate. In a certain embodiment, the term "stably preserving" as used herein represents a concept including suppression of a decrease in coordination efficiency of a metal radioisotope to a ligand and fluorescent dye color degradation. Specifically, in a certain embodiment, the present invention provides a method for stably preserving a labeling moiety-anti-human antibody Fab fragment conjugate, comprising the steps of: (a) adding citric acid, phosphoric acid, 2-[4-(2-hydroxyethyl)-1-piperazinyl]ethanesulfonic acid or trishydroxymethyl aminomethane as a buffering agent to a solution containing the labeling moiety-anti-human antibody Fab fragment conjugate; (b) adding sucrose or glycerin as a stabilizer to the solution containing the labeling moiety-anti-human antibody Fab fragment conjugate; (c) adding Polysorbate 80 as a nonionic surfactant to the solution containing the labeling moiety-anti-human antibody Fab fragment conjugate; and (d) adjusting the pH of the solution containing the labeling moiety-anti-human antibody Fab fragment conjugate to 6.5 to 7.5. The order of the addition is not particularly limited.

For the production method and the method for stably preserving, the structures of the anti-human antibody Fab fragment and the labeling moiety, the structure of the labeling moiety-anti-human antibody Fab fragment conjugate, and the like are as described in the section "1. Pharmaceutical composition". The ranges of the concentrations, the ranges of the pHs, and the like of the buffering agent, the stabilizer and the nonionic surfactant are also as described in the section "1. Pharmaceutical composition". The steps may be carried out in any order.

When the labeling moiety-anti-human antibody Fab fragment conjugate comprises a ligand as the labeling moiety in the production method and the method, a certain embodiment may comprise the step of coordinating a metal radioisotope. The type of the metal radioisotope, and the like are as described in the section "1. Pharmaceutical composition".

Further, in the production method and the method, a certain embodiment may comprise the step of performing freezing or the step of performing lyophilization. As the freezing method or the lyophylization method, a known method can be used.

4. Method for Producing Labeling Moiety-Anti-Human Antibody Fab Fragment Conjugate 4-1. Polynucleotide Encoding Anti-Human Antibody Fab Fragment When the conjugate contained in the pharmaceutical composition of the present invention comprises the anti-human CEACAM5 antibody Fab fragment, a certain embodiment of a polynucleotide encoding the anti-human antibody Fab fragment comprises a polynucleotide comprising a nucleotide sequence encoding a heavy chain fragment of the anti-human CEACAM5 antibody Fab fragment, and a polynucleotide comprising a nucleotide sequence encoding the light chain of the anti-human CEACAM5 antibody Fab fragment.

In a certain embodiment, the polynucleotide encoding the anti-human CEACAM5 antibody Fab fragment is a polynucleotide comprising a nucleotide sequence encoding a heavy chain fragment comprising a heavy chain variable region consisting of the amino acid sequence represented by amino acid positions 1 to 121 of SEQ ID NO: 2, or a polynucleotide comprising a nucleotide sequence encoding a light chain comprising a light chain variable region consisting of the amino acid sequence represented by amino acid positions 1 to 112 of SEQ ID NO: 4.

Examples of the polynucleotide comprising a nucleotide sequence encoding a heavy chain fragment comprising a heavy chain variable region consisting of the amino acid sequence represented by amino acid positions 1 to 121 of SEQ ID NO: 2 include a polynucleotide comprising a nucleotide sequence from nucleotide positions 1 to 363 of SEQ ID NO: 1. Examples of the polynucleotide comprising a nucleotide sequence encoding a light chain comprising a light chain variable region consisting of an amino acid sequence from amino acid positions 1 to 112 of SEQ ID NO: 4 include a polynucleotide comprising a nucleotide sequence from nucleotide positions 1 to 336 of SEQ ID NO: 3.

In a preferred embodiment, the polynucleotide encoding the anti-human CEACAM5 antibody Fab fragment is a polynucleotide comprising a nucleotide sequence encoding a heavy chain fragment consisting of the amino acid sequence represented by SEQ ID NO: 2, or a polynucleotide comprising a nucleotide sequence encoding a light chain consisting of the amino acid sequence represented by SEQ ID NO: 4.

Examples of the polynucleotide comprising a nucleotide sequence encoding a heavy chain fragment consisting of the amino acid sequence represented by SEQ ID NO: 2 include a polynucleotide comprising the nucleotide sequence represented by SEQ ID NO: 1. Examples of the polynucleotide comprising a nucleotide sequence encoding a light chain consisting of the amino acid sequence represented by SEQ ID NO: 4 include a polynucleotide comprising the nucleotide sequence represented by SEQ ID NO: 3.

When the conjugate contained in the pharmaceutical composition of the present invention comprises the anti-human MUC1 antibody Fab fragment, a certain embodiment of a polynucleotide encoding the anti-human antibody Fab fragment comprises a polynucleotide comprising a nucleotide sequence encoding a heavy chain fragment of the anti-human MUC1 antibody Fab fragment, and a polynucleotide comprising a nucleotide sequence encoding the light chain of the anti-human MUC1 antibody Fab fragment.

A certain embodiment of the polynucleotide encoding the anti-human MUC1 antibody Fab fragment is a polynucleotide comprising a nucleotide sequence encoding a heavy chain fragment comprising a heavy chain variable region consisting of the amino acid sequence represented by SEQ ID NO: 12, or a polynucleotide comprising a nucleotide sequence encoding a heavy chain fragment comprising a heavy chain variable region consisting of the amino acid sequence represented by SEQ ID NO: 14.

Examples of the polynucleotide comprising a nucleotide sequence encoding a heavy chain fragment comprising a heavy chain variable region consisting of the amino acid sequence represented by SEQ ID NO: 12 include a polynucleotide comprising the nucleotide sequence represented by SEQ ID NO: 11. Examples of the polynucleotide comprising a nucleotide sequence encoding a heavy chain fragment comprising a heavy chain variable region consisting of the amino acid sequence represented by SEQ ID NO: 14 include a polynucleotide comprising the nucleotide sequence represented by SEQ ID NO: 13.

In a preferred embodiment, the polynucleotide encoding the anti-human MUC1 antibody Fab fragment is a polynucleotide comprising a nucleotide sequence encoding a heavy chain fragment consisting of the amino acid sequence represented by SEQ ID NO: 6, or a polynucleotide comprising a nucleotide sequence encoding a heavy chain fragment consisting of the amino acid sequence represented by SEQ ID NO: 8.

Examples of the polynucleotide comprising a nucleotide sequence encoding a heavy chain fragment consisting of the amino acid sequence represented by SEQ ID NO: 6 include a polynucleotide comprising the nucleotide sequence represented by SEQ ID NO: 5. Examples of the polynucleotide comprising a nucleotide sequence encoding a heavy chain fragment consisting of the amino acid sequence represented by SEQ ID NO: 8 include a polynucleotide comprising the nucleotide sequence represented by SEQ ID NO: 7.

In a certain embodiment, the polynucleotide encoding the anti-human MUC1 antibody Fab fragment is a polynucleotide comprising a nucleotide sequence encoding a light chain comprising a light chain variable region consisting of the amino acid sequence represented by SEQ ID NO: 16.

Examples of the polynucleotide comprising a nucleotide sequence encoding a light chain comprising a light chain variable region consisting of the amino acid sequence represented by SEQ ID NO: 16 include a polynucleotide comprising the nucleotide sequence represented by SEQ ID NO: 15.

In a preferred embodiment, the polynucleotide encoding the anti-human MUC1 antibody Fab fragment is a polynucleotide comprising a nucleotide sequence encoding a light chain consisting of the amino acid sequence represented by SEQ ID NO: 10.

Examples of the polynucleotide comprising a nucleotide sequence encoding a light chain consisting of the amino acid sequence represented by SEQ ID NO: 10 include a polynucleotide comprising the nucleotide sequence represented by SEQ ID NO: 9.

The polynucleotide encoding the anti-human CEACAM5 antibody Fab fragment contained in the pharmaceutical composition of the present invention can be synthesized through the use of a gene synthesis method known in the art on the basis of nucleotide sequences designed from the amino acid sequences of the heavy chain fragment and the light chain of the anti-human CEACAM5 antibody Fab fragment or the anti-human MUC1 antibody Fab fragment. Various methods known to those skilled in the art, such as methods for synthesizing an antibody gene described in International Publication No. WO 90/07861 can be used as such gene synthesis methods.

4-2. Expression Vector of Polynucleotide Encoding Anti-Human Antibody Fab Fragment The expression vector of the polynucleotide encoding the anti-human CEACAM5 antibody Fab fragment in the conjugate contained in the pharmaceutical composition of the present invention includes an expression vector comprising a polynucleotide comprising a nucleotide sequence encoding the heavy chain fragment of the anti-human CEACAM5 antibody Fab fragment, an expression vector comprising a polynucleotide comprising a nucleotide sequence encoding the light chain of the anti-human CEACAM5 antibody Fab fragment, and an expression vector comprising a polynucleotide comprising a nucleotide sequence encoding the heavy chain fragment of the anti-human CEACAM5 antibody Fab fragment and a polynucleotide comprising a nucleotide sequence encoding the light chain of the anti-human CEACAM5 antibody Fab fragment.

The preferred expression vector includes an expression vector comprising a polynucleotide comprising a nucleotide sequence encoding a heavy chain fragment comprising a heavy chain variable region consisting of the amino acid sequence represented by amino acid positions 1 to 121 of SEQ ID NO: 2, an expression vector comprising a polynucleotide comprising a nucleotide sequence encoding a light chain comprising a light chain variable region consisting of the amino acid sequence represented by amino acid positions 1 to 112 of SEQ ID NO: 4, and an expression vector comprising a polynucleotide comprising a nucleotide sequence encoding a heavy chain fragment comprising a heavy chain variable region consisting of the amino acid sequence represented by amino acid positions 1 to 121 of SEQ ID NO: 2 and a polynucleotide comprising a nucleotide sequence encoding a light chain comprising a light chain variable region consisting of the amino acid sequence represented by amino acid positions 1 to 112 of SEQ ID NO: 4.

The more preferred expression vector encoding the anti-human CEACAM5 antibody Fab fragment contained in the pharmaceutical composition of the present invention includes an expression vector comprising a polynucleotide comprising a nucleotide sequence encoding a heavy chain fragment consisting of the amino acid sequence represented by SEQ ID NO: 2, an expression vector comprising a polynucleotide comprising a nucleotide sequence encoding a light chain consisting of the amino acid sequence represented by SEQ ID NO: 4, and an expression vector comprising a polynucleotide comprising a nucleotide sequence encoding a heavy chain fragment consisting of the amino acid sequence represented by SEQ ID NO: 2 and a polynucleotide comprising a nucleotide sequence encoding a light chain consisting of the amino acid sequence represented by SEQ ID NO: 4.

The expression vector of the polynucleotide encoding the anti-human MUC1 antibody Fab fragment in the conjugate contained in the pharmaceutical composition of the present invention includes an expression vector comprising a polynucleotide comprising a nucleotide sequence encoding the heavy chain fragment of the anti-human MUC1 antibody Fab fragment, an expression vector comprising a polynucleotide comprising a nucleotide sequence encoding the light chain of the anti-human MUC1 antibody Fab fragment, and an expression vector comprising a polynucleotide comprising a nucleotide sequence encoding the heavy chain fragment of the anti-human MUC1 antibody Fab fragment and a polynucleotide comprising a nucleotide sequence encoding the light chain of the anti-human MUC1 antibody Fab fragment.

The preferred expression vector includes an expression vector comprising a polynucleotide comprising a nucleotide sequence encoding a heavy chain variable region consisting of the amino acid sequence represented by SEQ ID NO: 12 or SEQ ID NO: 14, an expression vector comprising a polynucleotide comprising a nucleotide sequence encoding a light chain variable region consisting of the amino acid sequence represented by SEQ ID NO: 16, and an expression vector comprising a polynucleotide comprising a nucleotide sequence encoding a heavy chain variable region consisting of the amino acid sequence represented by SEQ ID NO: 12 or SEQ ID NO: 14 and a polynucleotide comprising a nucleotide sequence encoding a light chain variable region consisting of the amino acid sequence represented by SEQ ID NO: 16.

The more preferred expression vector includes an expression vector comprising a polynucleotide comprising a nucleotide sequence encoding a heavy chain fragment consisting of the amino acid sequence represented by SEQ ID NO: 6 or SEQ ID NO: 8, an expression vector comprising a polynucleotide comprising a nucleotide sequence encoding a light chain consisting of the amino acid sequence represented by SEQ ID NO: 10, and an expression vector comprising a polynucleotide comprising a nucleotide sequence encoding a heavy chain fragment consisting of the amino acid sequence represented by SEQ ID NO: 6 or SEQ ID NO: 8 and a polynucleotide comprising a nucleotide sequence encoding a light chain consisting of the amino acid sequence represented by SEQ ID NO: 10.

These expression vectors are not particularly limited as long as a polypeptide encoded by the polynucleotide can be produced in various host cells of prokaryotic cells and/or eukaryotic cells. Examples of such expression vectors include plasmid vectors and virus vectors (e.g., adenovirus and retrovirus) or the like. Preferably, pEE6.4 or pEE12.4 (Lonza Group AG) can be used.

These expression vectors may comprise a promoter operably linked to a gene encoding the heavy chain fragment and/or the light chain in the polynucleotide encoding the anti-human antibody Fab fragment contained in the pharmaceutical composition of the present invention. Examples of the promoter for expressing the Fab fragment contained in the pharmaceutical composition of the present invention in a host cell include Trp promoter, lac promoter, recA promoter, λPL promoter, lpp promoter, and tac promoter or the like, when the host cell is a bacterium of the genus *Escherichia*. Examples of the promoter for expression in yeasts include PH05 promoter, PGK promoter, GAP promoter, and ADH promoter or the like. Examples of the promoter for expression in bacteria of the genus *Bacillus* include SL01 promoter, SP02 promoter, and penP promoter or the like. Examples thereof include promoters derived from viruses such as CMV, RSV, and SV40, retrovirus promoter, actin promoter, EF (elongation factor) 1a promoter, and heat shock promoter or the like, when the host is a eukaryotic cell such as a mammalian cell.

In the case of using a bacterium, particularly, *E. coli*, as a host cell, these expression vector may further comprise a start codon, a stop codon, a terminator region and a replicable unit. On the other hand, in the case of using a yeast, an animal cell or an insect cell as a host, the expression vector encoding the anti-human antibody Fab fragment contained in the pharmaceutical composition of the present invention may comprise a start codon and a stop codon. In this case, an enhancer sequence, 5' and 3' untranslated regions of a gene encoding the heavy chain fragment and/or the light chain contained in the pharmaceutical composition of the present invention, a secretion signal sequence, a splicing junction, a polyadenylation site, or a replicable unit, etc. may be contained therein. Also, a selective marker usually used (e.g., tetracycline resistance gene, ampicillin resistance gene, kanamycin resistance gene, neomycin resistance gene, and dihydrofolate reductase gene) may be contained therein according to a purpose.

4-3. Host Cell Transformed with Expression Vector

The host cell transformed with the expression vector of the polynucleotide encoding the anti-human CEACAM5 antibody Fab fragment includes a host cell transformed with the expression vector selected from the group consisting of the following (a) to (d):

(a) a host cell transformed with an expression vector comprising a polynucleotide comprising a nucleotide sequence encoding the heavy chain fragment of the anti-human CEACAM5 antibody Fab fragment contained in the pharmaceutical composition of the present invention;

(b) a host cell transformed with an expression vector comprising a polynucleotide comprising a nucleotide sequence encoding the light chain of the anti-human CEACAM5 antibody Fab fragment contained in the pharmaceutical composition of the present invention;

(c) a host cell transformed with an expression vector comprising a polynucleotide comprising a nucleotide sequence encoding the heavy chain fragment of the anti-human CEACAM5 antibody Fab fragment contained in the pharmaceutical composition of the present invention and a polynucleotide comprising a nucleotide sequence encoding the light chain of the anti-human CEACAM5 antibody Fab fragment contained in the pharmaceutical composition of the present invention; and (d) a host cell transformed with an expression vector comprising a polynucleotide comprising a nucleotide sequence encoding the heavy chain fragment of the anti-human CEACAM5 antibody Fab fragment contained in the pharmaceutical composition of the present invention and an expression vector comprising a polynucleotide comprising a nucleotide sequence encoding the light chain of the anti-human CEACAM5 antibody Fab fragment contained in the pharmaceutical composition of the present invention.

In one embodiment, the host cell transformed with the expression vector of the polynucleotide encoding the anti-human CEACAM5 antibody Fab fragment is a host cell selected from the group consisting of the following (a) to (d):

(a) a host cell transformed with an expression vector comprising a polynucleotide comprising a nucleotide sequence encoding a heavy chain fragment comprising a heavy chain variable region consisting of the amino acid sequence represented by amino acid positions 1 to 121 of SEQ ID NO: 2;

(b) a host cell transformed with an expression vector comprising a polynucleotide comprising a nucleotide sequence encoding a light chain comprising a light chain variable region consisting of the amino acid sequence represented by amino acid positions 1 to 112 of SEQ ID NO: 4;

(c) a host cell transformed with an expression vector comprising a polynucleotide comprising a nucleotide sequence encoding a heavy chain fragment comprising a heavy chain variable region consisting of the amino acid sequence represented by amino acid positions 1 to 121 of SEQ ID NO: 2 and a polynucleotide comprising a nucleotide sequence encoding a light chain comprising a light chain variable region consisting of the amino acid sequence represented by amino acid positions 1 to 112 of SEQ ID NO: 4; and (d) a host cell transformed with an expression vector comprising a polynucleotide comprising a nucleotide sequence encoding a heavy chain fragment comprising a heavy chain variable region consisting of the amino acid sequence represented by amino acid positions 1 to 121 of SEQ ID NO: 2 and an expression vector comprising a polynucleotide comprising a nucleotide sequence encoding a light chain comprising a light chain variable region consisting of the amino acid sequence represented by amino acid positions 1 to 112 of SEQ ID NO: 4.

In one embodiment, the host cell transformed with the expression vector of the polynucleotide encoding the anti-human CEACAM5 antibody Fab fragment is a host cell selected from the group consisting of the following (a) to (d):

(a) a host cell transformed with an expression vector comprising a polynucleotide comprising a nucleotide sequence encoding a heavy chain fragment consisting of the amino acid sequence represented by SEQ ID NO: 2;

(b) a host cell transformed with an expression vector comprising a polynucleotide comprising a nucleotide sequence encoding a light chain consisting of the amino acid sequence represented by SEQ ID NO: 4;

(c) a host cell transformed with an expression vector comprising a polynucleotide comprising a nucleotide sequence encoding a heavy chain fragment consisting of the amino acid sequence represented by SEQ ID NO: 2 and a polynucleotide comprising a nucleotide sequence encoding a light chain consisting of the amino acid sequence represented by SEQ ID NO: 4; and (d) a host cell transformed with an expression vector comprising a polynucleotide comprising a nucleotide sequence encoding a heavy chain fragment consisting of the amino acid sequence represented by SEQ ID NO: 2 and expression vector comprising a polynucleotide comprising a nucleotide sequence encoding a light chain consisting of the amino acid sequence represented by SEQ ID NO: 4.

The host cell transformed with the expression vector of the polynucleotide encoding the anti-human MUC1 antibody Fab fragment includes a host cell transformed with the expression vector selected from the group consisting of the following (a) to (d):

(a) a host cell transformed with an expression vector comprising a polynucleotide comprising a nucleotide sequence encoding the heavy chain fragment of the anti-human MUC1 antibody Fab fragment contained in the pharmaceutical composition of the present invention;
(b) a host cell transformed with an expression vector comprising a polynucleotide comprising a nucleotide sequence encoding the light chain of the anti-human MUC1 antibody Fab fragment contained in the pharmaceutical composition of the present invention;
(c) a host cell transformed with an expression vector comprising a polynucleotide comprising a nucleotide sequence encoding the heavy chain fragment of the anti-human MUC1 antibody Fab fragment contained in the pharmaceutical composition of the present invention and a polynucleotide comprising a nucleotide sequence encoding the light chain of the anti-human MUC1 antibody Fab fragment contained in the pharmaceutical composition of the present invention; and
(d) a host cell transformed with an expression vector comprising a polynucleotide comprising a nucleotide sequence encoding the heavy chain fragment of the anti-human MUC1 antibody Fab fragment contained in the pharmaceutical composition of the present invention and an expression vector comprising a polynucleotide comprising a nucleotide sequence encoding the light chain of the anti-human MUC1 antibody Fab fragment contained in the pharmaceutical composition of the present invention.

In one embodiment, the host cell transformed with the expression vector of the polynucleotide encoding the anti-human MUC1 antibody Fab fragment is a host cell selected from the group consisting of the following (a) to (d):
(a) a host cell transformed with an expression vector comprising a polynucleotide comprising a nucleotide sequence encoding a heavy chain fragment comprising a heavy chain variable region consisting of the amino acid sequence represented by SEQ ID NO: 12 or SEQ ID NO: 14;
(b) a host cell transformed with an expression vector comprising a polynucleotide comprising a nucleotide sequence encoding a light chain comprising a light chain variable region consisting of the amino acid sequence represented by SEQ ID NO: 16;
(c) a host cell transformed with an expression vector comprising a polynucleotide comprising a nucleotide sequence encoding a heavy chain fragment comprising a heavy chain variable region consisting of the amino acid sequence represented by SEQ ID NO: 12 or SEQ ID NO: 14 and a polynucleotide comprising a nucleotide sequence encoding a light chain comprising a light chain variable region consisting of the amino acid sequence represented by SEQ ID NO: 16; and
(d) a host cell transformed with an expression vector comprising a polynucleotide comprising a nucleotide sequence encoding a heavy chain fragment comprising a heavy chain variable region consisting of the amino acid sequence represented by SEQ ID NO: 12 or SEQ ID NO: 14 and an expression vector comprising a polynucleotide comprising a nucleotide sequence encoding a light chain comprising a light chain variable region consisting of the amino acid sequence represented by SEQ ID NO: 16.

In one embodiment, the host cell transformed with the expression vector of the polynucleotide encoding the anti-human MUC1 antibody Fab fragment is a host cell selected from the group consisting of the following (a) to (d):
(a) a host cell transformed with an expression vector comprising a polynucleotide comprising a nucleotide sequence encoding a heavy chain fragment consisting of the amino acid sequence represented by SEQ ID NO: 6 or SEQ ID NO: 8;
(b) a host cell transformed with an expression vector comprising a polynucleotide comprising a nucleotide sequence encoding a light chain consisting of the amino acid sequence represented by SEQ ID NO: 10;
(c) a host cell transformed with an expression vector comprising a polynucleotide comprising a nucleotide sequence encoding a heavy chain fragment consisting of the amino acid sequence represented by SEQ ID NO: 6 or SEQ ID NO: 8 and a polynucleotide comprising a nucleotide sequence encoding a light chain consisting of the amino acid sequence represented by SEQ ID NO: 10; and
(d) a host cell transformed with an expression vector comprising a polynucleotide comprising a nucleotide sequence encoding a heavy chain fragment consisting of the amino acid sequence represented by SEQ ID NO: 6 or SEQ ID NO: 8 and expression vector comprising a polynucleotide comprising a nucleotide sequence encoding a light chain consisting of the amino acid sequence represented by SEQ ID NO: 10.

The host cell to be transformed is not particularly limited as long as it is compatible with the expression vector used and can be transformed with the expression vector to express the Fab fragment. Examples thereof include various cells such as natural cells and artificially established cells usually used in the technical field of the present invention (e.g., bacteria (bacteria of the genus *Escherichia* and bacteria of the genus *Bacillus*), yeasts (the genus *Saccharomyces*, the genus *Pichia*, etc.), animal cells and insect cells (e.g., Sf9), etc.), and mammalian cell lines (e.g., cultured cells such as CHOK1SV cells, CHO-DG44 cells, and 293 cells, etc.). The transformation itself can be performed by a known method, for example, a calcium phosphate method or an electroporation method.

4-4. Method for Producing Anti-Human Antibody Fab Fragment

The method for producing the anti-human antibody Fab fragment, preferably the method for producing the anti-human CEACAM5 antibody Fab fragment or the anti-human MUC1 antibody Fab fragment, comprises the step of culturing the transformed host cell to express the anti-human antibody Fab fragment.

In the method for producing an anti-human antibody Fab fragment, the transformed host cell can be cultured in a nutrient medium. The nutrient medium preferably contains a nutrient source such as a carbon source, an inorganic nitrogen source or an organic nitrogen source necessary for the growth of the transformed host cell. Examples of the carbon source include glucose, dextran, soluble starch, and sucrose or the like. Examples of the inorganic nitrogen source or the organic nitrogen source include ammonium salts, nitrates, amino acids, corn steep liquor, peptone, casein, meat extracts, soymeal, and potato extracts or the like. Also, other nutrients (e.g., inorganic salts (e.g., calcium chloride, sodium dihydrogen phosphate, and magnesium chloride), vitamins, and antibiotics (e.g., tetracycline, neomycin, ampicillin, and kanamycin, etc.), etc.) may be contained therein, if desired.

The culture itself of the transformed host cell is performed by a known method. Culture conditions, for example, temperature, medium pH and culture time, are appropriately selected. When the host is, for example, an animal cell, MEM medium (Science; 1952; 122: 501), DMEM medium (Virology; 1959; 8: 396-97), RPMI1640 medium (J. Am. Med. Assoc.; 1967; 199: 519-24), 199 medium (Proc. Soc. Exp. Biol. Med.; 1950; 73:1-8), or the like containing approximately 5 to 20% fetal bovine serum can be used as a medium. The medium pH is preferably approximately 6 to 8. The culture is usually performed at approximately 30 to 40° C. for approximately 15 to 336 hours, and aeration or stirring can also be performed, if necessary. When the host is an insect cell, examples thereof include Grace's medium (PNAS; 1985; 82: 8404-8) or the like containing fetal bovine serum. Its pH is preferably approximately 5 to 8. The culture is usually performed at approximately 20 to 40° C. for 15 to 100 hours, and aeration or stirring can also be performed, if necessary. When the host is a bacterium, an actinomycete, a yeast, or a filamentous fungus, for example, a liquid medium containing the nutrient source described above is appropriate. A medium of pH 5 to 8 is preferred. When the host is *E. coli*, preferred examples of the medium include LB medium and M9 medium (Miller et al., Exp. Mol. Genet, Cold Spring Harbor Laboratory; 1972: 431) or the like. In such a case, the culture can usually be performed at 14 to 43° C. for approximately 3 to 24 hours with aeration or stirring, if necessary. When the host is a bacterium of the genus *Bacillus*, it can usually be performed at 30 to 40° C. for approximately 16 to 96 hours with aeration or stirring, if necessary. When the host is a yeast, examples of the medium include Burkholder minimum medium (PNAS; 1980; 77: 4505-8). Its pH is desirably 5 to 8. The culture is usually performed at approximately 20 to 35° C. for approximately 14 to 144 hours, and aeration or stirring can also be performed, if necessary.

The method for producing an anti-human antibody Fab fragment can comprise the step of recovering, preferably isolating or purifying, the expressed anti-human antibody Fab fragment, in addition to the step of culturing the transformed host cell to express the anti-human antibody Fab fragment. Examples of the isolation or purification method include: methods exploiting solubility, such as salting out and a solvent precipitation method or the like; methods exploiting difference in molecular weight, such as dialysis, ultrafiltration, gel filtration, and sodium dodecyl sulfate-polyacrylamide gel electrophoresis or the like; methods exploiting charge, such as ion-exchange chromatography and hydroxylapatite chromatography or the like; methods exploiting specific affinity, such as affinity chromatography or the like; methods exploiting difference in hydrophobicity, such as reverse-phase high-performance liquid chromatography or the like; and methods exploiting difference in isoelectric point, such as isoelectric focusing or the like; or the like.

4-5. Method for Producing Labeling Moiety-Anti-Human Antibody Fab Fragment Conjugate The method for producing the labeling moiety-anti-human antibody Fab fragment conjugate contained in the pharmaceutical composition of the present invention comprises the step of covalently binding the anti-human antibody Fab fragment to a labeling moiety. The method for producing a conjugate may also comprise the steps of: culturing the transformed host cell to express the anti-human antibody Fab fragment; and covalently binding the Fab fragment to a labeling moiety. The method for producing a conjugate may also comprise the steps of: culturing the transformed host cell to express the anti-human antibody Fab fragment; recovering the expressed Fab fragment; and covalently binding the Fab fragment to a labeling moiety. The linker, ligand, or fluorescent dye, etc. used can employ those described in the section "1. Pharmaceutical composition".

A certain embodiment of the method for producing a conjugate is a method comprising the steps of: culturing the transformed host cell to express the anti-human antibody Fab fragment; and binding the Fab fragment via a linker to a ligand. A certain embodiment of the method for producing a conjugate is a method comprising the steps of: culturing the transformed host cell to express the anti-human antibody Fab fragment; recovering the expressed Fab fragment; and binding the Fab fragment via a linker to a ligand.

A certain embodiment of the method for producing a conjugate is a method comprising the steps of: culturing the transformed host cell to express the anti-human antibody Fab fragment; and i) binding the Fab fragment via a linker to a ligand or ii) covalently binding the Fab fragment directly to a ligand. A certain embodiment of the method for producing a conjugate is a method comprising the steps of: culturing the transformed host cell to express the anti-human antibody Fab fragment, recovering the expressed Fab fragment; and i) binding the Fab fragment via a linker to a ligand or ii) covalently binding the Fab fragment directly to a ligand.

A certain embodiment of the method for producing a conjugate is a method comprising the steps of: culturing the transformed host cell to express the anti-human antibody Fab fragment; and i) binding the Fab fragment via a linker to a fluorescent dye or ii) covalently binding the Fab fragment directly to a fluorescent dye. A certain embodiment of the method for producing a conjugate is a method comprising the steps of: culturing the transformed host cell to express the anti-human antibody Fab fragment, recovering the expressed Fab fragment; and i) binding the Fab fragment via a linker to a fluorescent dye or ii) covalently binding the Fab fragment directly to a fluorescent dye.

The present invention is generally described above. Particular Examples will be provided here for reference in order to obtain further understanding. However, these are given for illustrative purposes and do not limit the present invention.

EXAMPLES

Experiment 1-1: Preparation of Anti-Human CEACAM5 Antibody Fab Fragment

An antibody having variable regions expected not to attenuate affinity even by the binding of a labeling moiety was designed using a molecular model of a humanized antibody constructed in accordance with the literature (Proteins: Structure, Function, and Bioinformatics; 2014; 82: 1624-1635) after humanization of mouse-derived anti-human CEACAM5 antibody T84.66 with reference to the method described in the literature (Protein Eng. Des. Sel.; 2004; 17: 481-489).

A gene encoding a signal sequence (MEWSWVFLF-FLSVTTGVHS (SEQ ID NO: 17)) was connected to the 5' side of the heavy chain fragment gene (SEQ ID NO: 1) of the antibody, and this heavy chain fragment gene was inserted to GS vector pEE6.4 (Lonza Group AG). Also, a gene encoding a signal sequence (MSVPTQVLGLLLL-WLTDARC (SEQ ID NO: 18)) was connected to the 5' side of the light chain gene (SEQ ID NO: 3) of the antibody, and the light chain gene was inserted to GS vector pEE12.4 (Lonza Group AG). The aforementioned pEE vectors respectively having inserts of the heavy chain fragment and light chain genes of the antibody were cleaved with restriction enzymes NotI and PvuI and ligated using ligation kit TAKARA Ligation Kit Ver 2.1 (Takara Bio Inc.) to construct a GS vector having both the inserts of the heavy chain fragment and light chain genes.

The antibody was expressed by two types of methods, transient expression and constitutive expression, using the aforementioned GS vector having both the inserts of the heavy chain fragment and light chain genes. For the transient expression, Expi293F cells (Thermo Fisher Scientific Inc.) cultured into approximately 3000000 cells/mL in Expi293 Expression Medium (Thermo Fisher Scientific Inc.) were transfected with the aforementioned GS vector having both the inserts of the heavy chain fragment and light chain genes using ExpiFectamine 293 Transfection Kit (Thermo Fisher Scientific Inc.) and cultured for 5 to 7 days. The culture supernatant was purified using KappaSelect (GE Healthcare Japan Corp.) to obtain a Fab fragment. For the constitutive expression, CHOK1SV cells (Lonza Group AG) were transfected with a linear vector obtained with PvuI from the aforementioned GS vector having both the inserts of the heavy chain fragment and light chain genes, by electroporation using Gene Pulser (Bio-Rad Laboratories, Inc.). On the day following the transfection, methionine sulfoximine was added thereto, followed by culture for 5 to 7 days. The cells were inoculated to a semisolid medium containing methylcellulose. After colony formation, cells having a large expression level of the Fab fragment were obtained using ClonePix FL (Molecular Devices, LLC). The culture supernatant of the cells was purified using Capto L (GE Healthcare Japan Corp.), Q Sepharose Fast Flow (GE Healthcare Japan Corp.), and BioPro S75 (YMC Co., Ltd.) to obtain a Fab fragment.

The nucleotide sequence encoding the heavy chain fragment of the prepared anti-human CEACAM5 antibody Fab fragment (designated as PB009-1) is shown in SEQ ID NO: 1, and the amino acid sequence encoded thereby is shown in SEQ ID NO: 2. The nucleotide sequence encoding the light chain of PB009-1 is shown in SEQ ID NO: 3, and the amino acid sequence encoded thereby is shown in SEQ ID NO: 4. The heavy chain variable region of PB009-1 consists of an amino acid sequence from amino acid positions 1 to 121 of SEQ ID NO: 2, and heavy chain CDR1, CDR2, and CDR3 consist of amino acid sequences from amino acid positions 31 to 35, 50 to 66, and 99 to 110, respectively, of SEQ ID NO: 2. The light chain variable region of PB009-1 consists of an amino acid sequence from amino acid positions 1 to 112 of SEQ ID NO: 4, and light chain CDR1, CDR2, and CDR3 consist of amino acid sequences from amino acid positions 24 to 38, 54 to 60, and 93 to 101, respectively, of SEQ ID NO: 4.

The variable regions and the CDR sequences were determined according to the Kabat numbering (Kabat et al., 1991, Sequences of Proteins of Immunological Interest, 5th Ed., United States Public Health Service, National Institute of Health, Bethesda).

Experiment 1-2: Labeling of Chelating Agent of Anti-Human CEACAM5 Antibody Fab Fragment p-SCN-Bn-DFO (DFO substituted by a p-isothiocyanophenylaminothiocarbonyl group) (Macrocyclics, Inc.) was used in the binding of chelating agent DFO to anti-human CEACAM5 antibody Fab fragment PB009-1. A 1/5 amount of a 0.1 M sodium carbonate solution (pH 9.0) was added to a Fab fragment solution adjusted to 1 mg/mL with phosphate-buffered saline (pH 7.4). p-SCN-Bn-DFO was added thereto at a final concentration of 1 mg/mL and reacted at 37° C. for 1.5 hours. After the reaction, a DFO-anti-human CEACAM5 antibody Fab fragment conjugate bound to DFO via a linker (—C(=S)—NH-(1,4-phenylene)-NH—C(=S)—) (designated as PB009-2) was purified using Amicon Ultra 3K-0.5 mL centrifugal filter (Merck Millipore).

The number of ligands constituted by DFO bound to PB009-2 was confirmed by mass spectrometry. PB009-2 was desalted using MassPREP Micro Desalting Column (Waters Corp.), and measurement was carried out using SYNAPT G2 mass spectrometer (Waters Corp.). As a result, a molecule in which at least 3 to 10 ligands constituted by DFO were bound to one PB009-1 was confirmed.

Experiment 1-3: Examination of Effect of pH on Stabilization of DFO-Anti-Human CEACAM5 Antibody Fab Fragment Conjugate (Effect on Multimer Generation and Acidic-Side Charge Analog Generation)

For liquid formulation comprising PB009-2, an effect of pH on stabilization of PB009-2 was evaluated. In this test, samples A-1 to A-6 shown in Table 1 were prepared by adding a buffering agent and a nonionic surfactant to the liquid formulation comprising PB009-2 in such a manner that the final concentration of PB009-2 was 10 mg/mL. The pH was adjusted by adding an appropriate amount of hydrochloric acid or sodium hydroxide. Each sample was aseptically filtered through a filter having a pore size of 0.22 μm, and filled in an amount of 1.2 mL into a glass vial (with a volume of 3 mL). The glass vial was stoppered with a rubber stopper, and covered and capped with an aluminum cap.

TABLE 1

| Sample No. | Buffering agent | pH | Nonionic surfactant |
| --- | --- | --- | --- |
| A-1 | 20 mmol/L | 5.0 | 0.1 w/v % |
| A-2 | Citric acid | 6.0 | Polysorbate 80 |
| A-3 | | 7.0 | |
| A-4 | 20 mmol/L Tris | 7.0 | |
| A-5 | (trishydroxymethyl- | 7.5 | |
| A-6 | aminomethane) | 8.0 | |

For evaluating the stability of the liquid formulation, a heat stability test was conducted on each sample in a normally placed state. In the heat stability test, the stability of PB009-2 after storage at 25° C. for 1 week was evaluated on the basis of the amount of multimers measured by the size exclusion chromatography method (SE-HPLC method) and the amount of acidic charge variants measured by the imaging capillary isoelectric focusing method (icIEF method). Analysis conditions are as follows.

[Size Exclusion Chromatography Method (SE-HPLC Method)]

In SE-HPLC measurement, G3000SWXL (TOSOH CORPORATION) was connected to a HPLC system, and a mobile phase having a composition of phosphoric acid at 20 mmol/L and sodium chloride at 400 mmol/L (pH 7.0) was fed at a flow rate of 0.5 mL/min. The injection amount of the sample was 50 μg in terms of PB009-2 (e.g. 10 μL in the case of 5 mg/mL). The column temperature was set to 30° C., the sample temperature was set to 5° C., and detection was performed at UV 280 nm.

[Imaging Capillary Isoelectric Focusing Method (icIEF Method)]

In icIEF measurement, cIEF cartridge (Protein Simple, Inc.) was connected to iCE3 system, and the measurement was performed. 188 µL of a sample matrix consisting of urea, methylcellulose, Pharmalyte 3-10, pI marker 5.12 and pI marker 9.77 was mixed with 12 µL of a sample diluted to a PB009-2 concentration of 5 mg/mL with ultrapure water to give a measurement sample. Prefocusing was performed at 1500 V for 1 minute, and Focusing was performed at 3000 V for 6 minutes.

After the SE-HPLC measurement, the area of detected multimers were measured by an automatic analysis method to determine the amount of multimers (%). The amount of multimers (%) was defined in terms of a percentage (%) by measuring the total area of multimer peaks detected by the SE-HPLC method using the automatic analysis method, and being divided by the sum of all peak areas including a main peak area. Here, the main peak refers to a peak of an active main body (PB009-2 which is not multimerized).

The area of acidic charge variants detected by the icIEF method was measured by the automatic analysis method to determine the amount of acidic charge variants (%). The amount of acidic charge variants (%) is defined in terms of a percentage (%) by measuring the total area of acidic-side charge analog peaks detected by the icIEF method using the automatic analysis method, and being divided by the sum of all peak areas including a main peak area. Here, the main peak refers to a peak of an active main body (PB009-2 which is not variants).

Table 2 shows the evaluation results obtained by the SE-HPLC method and the icIEF method in this experiment. The results show that the amount of multimers in SE-HPLC (%) after storage at 25° C. for 1 week tended to increase with decrease in pH, and became minimum at a pH of about 7.0. The amount of acidic charge variants (%) after storage at 25° C. for 1 week tended to decrease with decrease in pH. Comprehensive judgement on the above results revealed that the optimum pH of the liquid formulation comprising PB009-2 was about 7.0, from the viewpoint of stability.

TABLE 2

| Sample No. | Buffering agent | pH | Amount of multimers in SE-HPLC (%) | | Amount of acidic-side charge analogs in icIEF (%) | |
| --- | --- | --- | --- | --- | --- | --- |
| | | | At start of test | After storage at 25° C. for 1 week | At start of test | After storage at 25° C. for 1 week |
| A-1 | 20 mmol/L | 5.0 | 2.6 | 12.3 | 46.2 | 37.6 |
| A-2 | Citric acid | 6.0 | 2.5 | 6.9 | 42.0 | 41.6 |
| A-3 | | 7.0 | 2.6 | 5.2 | 45.2 | 45.6 |
| A-4 | 20 mmol/L | 7.0 | 2.3 | 4.8 | 42.8 | 44.5 |
| A-5 | Tris | 7.5 | 2.3 | 5.1 | 45.4 | 42.6 |
| A-6 | | 8.0 | 2.4 | 5.9 | 45.0 | 45.6 |

Experiment 1-4: Examination of Effects of Stabilizer and Nonionic Surfactant on Stabilization of DFO-Anti-Human CEACAM5 Antibody Fab Fragment Conjugate (Effects on Multimer Generation and Acidic-Side Charge Analog Generation)

For liquid formulation comprising PB009-2, effects of various stabilizers or nonionic surfactants on stabilization of PB009-2 were evaluated. In this test, samples B-1 to B-10 shown in Table 3 were prepared by adding a buffering agent and an additive to the liquid formulation comprising PB009-2 in such a manner that the final concentration of PB009-2 was 10 mg/mL. The pH was adjusted by adding an appropriate amount of hydrochloric acid or sodium hydroxide. Each sample was aseptically filtered through a filter having a pore size of 0.22 µm, and filled in an amount of 1.2 mL into a glass vial (with a volume of 3 mL). The glass vial was stoppered with a rubber stopper, and covered and capped with an aluminum cap.

TABLE 3

| Sample No. | Buffering agent | pH | Additive |
| --- | --- | --- | --- |
| B-1 | 20 mmol/L Tris | 7.0 | 0.1 w/v % Polysorbate 80 |
| B-2 | | | 140 mM Arginine, 0.1 w/v % Polysorbate 80 |
| B-3 | | | 140 mM Histidine, 0.1 w/v % Polysorbate 80 |
| B-4 | | | 140 mM Aspartic acid, 0.1 w/v % Polysorbate 80 |
| B-5 | | | 280 mM Glycine, 0.1 w/v % Polysorbate 80 |
| B-6 | | | 280 mmol/L Sucrose, 0.1 w/v % Polysorbate 80 |
| B-7 | | | 280 mmol/L Sorbitol, 0.1 w/v % Polysorbate 80 |
| B-8 | | | 140 mmol/L Sodium acetate, 0.1 w/v % Polysorbate 80 |
| B-9 | | | 140 mmol/L Sodium chloride, 0.1 w/v % Polysorbate 80 |

TABLE 3-continued

| Sample No. | Buffering agent | pH | Additive |
| --- | --- | --- | --- |
| B-10 | | | 20 w/v % Glycerin, 0.1 w/v % Polysorbate 80 |

For evaluating the stability of the liquid formulation, a heat stability test was conducted on each sample in a normally placed state. In the heat stability test, the stability of PB009-2 after storage at 25° C. for 1 week was evaluated on the basis of the amount of multimers measured by the SE-HPLC method and the amount of acidic charge variants measured by the icIEF method. The experimental procedure of the SE-HPLC method is as follows.

[Size Exclusion Chromatography Method (SE-HPLC Method)]

In SE-HPLC measurement, AdvanceBio SEC 300A column (Agilent Technologies) was connected to a HPLC system, and a mobile phase having a composition of phosphoric acid at 20 mmol/L and sodium chloride at 400 mmol/L (pH 7.0) was fed at a flow rate of 0.5 mL/min. The injection amount of the sample was 50 μg in terms of PB009-2 (e.g. 10 μL in the case of 5 mg/mL). The column temperature was set to 30° C., the sample temperature was set to 5° C., and detection was performed at UV 280 nm.

After the SE-HPLC measurement, the area of detected multimers were measured by an automatic analysis method to determine the amount of multimers (%). The amount of multimers (%) was defined in terms of a percentage (%) by measuring the total area of multimer peaks detected by the SE-HPLC method using the automatic analysis method, and being divided by the sum of all peak areas including a main peak area. Here, the main peak refers to a peak of an active main body (PB009-2 which is not multimerized).

The analysis conditions of the icIEF method are the same as those in Experiment 1-3.

Table 4 shows the evaluation results obtained by the SE-HPLC method and the icIEF method in this experiment. First, an increase in the amount of multimers in SE-HPLC (%) after storage at 25° C. for 1 week tended to be suppressed in samples containing histidine, sucrose and glycerin, respectively. The amount of acidic charge variants (%) after storage at 25° C. for 1 week increased in samples containing histidine and aspartic acid, respectively. Comprehensive judgement on the above results revealed that sucrose or glycerin was desirable as a stabilizer for the liquid formulation comprising PB009-2, from the viewpoint of stability.

TABLE 4

| Sample No. | Amount of multimers in SE-HPLC (%) | | Amount of acidic-side charge analogs in icIEF (%) | |
|---|---|---|---|---|
| | At start of test | After storage at 25° C. for 1 week | At start of test | After storage at 25° C. for 1 week |
| B-1 | 1.4 | 4.0 | 44.0 | 45.7 |
| B-2 | 1.4 | 3.6 | 42.7 | 46.2 |
| B-3 | 1.4 | 3.1 | 41.4 | 53.3 |
| B-4 | 1.3 | 3.7 | 48.5 | 54.9 |
| B-5 | 1.5 | 4.0 | 40.2 | 44.8 |
| B-6 | 1.4 | 3.1 | 42.1 | 46.1 |
| B-7 | 1.4 | 3.4 | 44.8 | 46.1 |
| B-8 | 1.4 | 3.4 | 39.4 | 46.0 |
| B-9 | 1.6 | 4.0 | 42.7 | 44.4 |
| B-10 | 1.2 | 2.6 | 40.4 | 43.0 |

Experiment 1-5: Examination of Effect of Surfactant on Stabilization of DFO-Anti Human CEACAM5 Antibody Fab Fragment Conjugate (Effect on Insoluble Subvisible Particle Generation)

As liquid formulation formulated to comprise PB009-2 at 10 mg/mL and citric acid at 20 mmol/L and have a pH of 7.0, samples comprising Polysorbate 80 as a surfactant at 0 to 0.6 w/v % were prepared (samples No. C-1 to C-7: see Table 5). The pH was adjusted by adding an appropriate amount of hydrochloric acid or sodium hydroxide. Each sample was aseptically filtered through a filter having a pore size of 0.22 μm, and filled in an amount of 1.2 mL into a glass vial (with a volume of 3 mL). The glass vial was stoppered with a rubber stopper, and covered and capped with an aluminum cap.

TABLE 5

| Sample No. | Buffering agent | pH | Nonionic surfactant |
|---|---|---|---|
| C-1 | 20 mmol//L Citric acid | 7.0 | 0 w/v % Polysorbate 80 |
| C-2 | | | 0.02 w/v % Polysorbate 80 |
| C-3 | | | 0.05 w/v % Polysorbate 80 |
| C-4 | | | 0.1 w/v % Polysorbate 80 |
| C-5 | | | 0.2 w/v % Polysorbate 80 |
| C-6 | | | 0.4 w/v % Polysorbate 80 |
| C-7 | | | 0.6 w/v % Polysorbate 80 |

For each sample, the number of insoluble subvisible particles after shaking and after freezing and thawing was measured using a light obscuration particle count method. The shaking test was conducted by shaking the sample at 150 rpm for 24 hours. The freezing and thawing test was conducted by carrying out a total of three processes each comprising freezing the sample at −80° C. for 4 hours or more, and then thawing the sample at 5° C. for 4 hours or more. The analysis conditions of the light obscuration particle count method are as follows.

[Light Obscuration Particle Count Method]

0.2 mL of the sample was injected into a HIAC system (Pacific Scientific Company) to perform measurement of the number of insoluble subvisible particles having a particle size of 1.2 μm or more in 1 mL of the sample.

Table 6 shows the evaluation results obtained by the light obscuration particle count method in this experiment. It was shown that the number of insoluble subvisible particles increased due to shaking and freezing and thawing, but addition of Polysorbate 80 at a concentration of 0.02 w/v % or more suppressed the increase. It was confirmed that addition of Polysorbate 80 at 0.05 w/v % to the liquid formulation comprising PB009-2 was desirable from the viewpoint of suppressing generation of the insoluble subvisible particles.

TABLE 6

| | Number of insoluble fine particles (≥1.2 μm/mL) | | |
|---|---|---|---|
| Sample No. | At start of test | After shaking | After freezing and thawing |
| C-1 | 1950 | N/A (unmeasurable) | 61335 |
| C-2 | 440 | 2910 | 3713 |
| C-3 | 283 | 2433 | 8115 |
| C-4 | 1743 | 470 | 11648 |
| C-5 | 683 | 4293 | 15065 |
| C-6 | 65 | 228 | 5938 |
| C-7 | 275 | 793 | 5275 |

Experiment 1-6: Selection of Optimum pH for Stabilizing DFO-Anti-Human CEACAM5 Antibody Fab Fragment Conjugate For formulations with the inclusion of PB009-2 at 10 mg/mL and with the inclusion of citric acid at 20 mmol/L or HEPES (2-[4-(2-hydroxyethyl)-1-piperazine]ethanesulfonic acid) at 20 mmol/L as a buffering agent, sucrose at 10 w/v % as a stabilizer and Polysorbate 80 at 0.05 w/v % as a nonionic surfactant (samples Nos. D-1 to D-8), samples were prepared at a pH of 6.1 to 7.9. The pH was adjusted by adding an appropriate amount of hydrochloric acid or sodium hydroxide. Each sample was aseptically filtered through a filter having a pore size of 0.22 μm, and filled in an amount of 1.2 mL into a glass vial (with a volume of 3 mL). The glass vial was stoppered with a rubber stopper, and covered and capped with an aluminum cap. Thereafter, for each sample, the stability of PB009-2 after storage at 25° C. for 1 week in a normally placed state was evaluated on the basis of the amount of multimers measured by the SE-HPLC method. The SE-HPLC method was carried out in the same manner as in Experiment 1-4.

Table 7 shows the evaluation results obtained by the SE-HPLC method in this experiment. The amount of multimers in SE-HPLC (%) after storage at 25° C. for 1 week tended to increase in high-pH samples and low-pH samples, and became the smallest at a pH of about 6.7. Therefore, it was found that the optimum pH was a pH of 6.7, and citric acid at 20 mmol/L was particularly preferable as a buffering agent for properly maintaining the optimum pH.

TABLE 7

| Sample No. | Buffering agent | pH | Amount of multimers in SE-HPLC (%) | |
|---|---|---|---|---|
| | | | At start of test | After storage at 25° C. for 1 week |
| D-1 | 20 mmol/L | 6.1 | 1.7 | 3.0 |
| D-2 | Citric acid | 6.4 | 1.6 | 2.9 |
| D-3 | | 6.7 | 1.5 | 2.9 |
| D-4 | | 7.0 | 1.6 | 3.2 |
| D-5 | 20 mmol/L | 7.0 | 1.6 | 3.1 |
| D-6 | HEPES | 7.3 | 1.6 | 3.3 |
| D-7 | | 7.6 | 1.7 | 4.0 |
| D-8 | | 7.9 | 1.9 | 4.6 |

Experiment 1-7: Examination of Optimization of Stabilizer Concentration for Stabilizing DFO-Anti-Human CEACAM5 Antibody Fab Fragment Conjugate From liquid formulation formulated to comprise PB009-2 at 10 mg/mL, citric acid at 20 mmol/L and Polysorbate 80 at 0.05 w/v % and have a pH of 6.7 (sample Nos. E-1 to E-5), samples comprising sucrose or glycerin at 0 to 20 w/v % were prepared. After being prepared in accordance with the formulations and compositions, the samples were each aseptically filtered through a filter having a pore size of 0.22 μm, and filled in an amount of 1.2 mL into a glass vial (with a volume of 3 mL). The glass vial was stoppered with a rubber stopper, and covered and capped with an aluminum cap. If necessary, hydrochloric acid and/or sodium hydroxide were added as a pH adjuster during preparation of the buffering agent so that a predetermined pH was obtained. Thereafter, for each sample, the stability of PB009-2 after storage at 25° C. for 1 week in a normally placed state was evaluated on the basis of the amount of multimers measured by the SE-HPLC method. The SE-HPLC method was carried out in the same manner as in Experiment 1-4.

Table 8 shows the evaluation results obtained by the SE-HPLC method in this experiment. The results revealed that after storage at 25° C. for 1 week, an increase in the amount of multimers in SE-HPLC (%) was suppressed with an increase in the concentration of sucrose or glycerin added. There was no difference in effect on the stability between sucrose and glycerin. The above results showed that sucrose at 10 w/v % was particularly preferable as a pharmaceutical additive for the liquid formulation comprising PB009-2 from the viewpoint of an osmotic pressure ratio.

TABLE 8

| | | Amount of multimers in SE-HPLC (%) | |
|---|---|---|---|
| Sample No. | Stabilizer | At start of test | After storage at 25° C. for 1 week |
| E-1 | None | 1.0 | 3.7 |
| E-2 | 10 w/v % Sucrose | 1.0 | 2.9 |
| E-3 | 20 w/v % Sucrose | 0.9 | 2.6 |
| E-4 | 10 w/v % Glycerin | 1.0 | 3.0 |
| E-5 | 20 w/v % Glycerin | 1.0 | 2.6 |

Experiment 1-8: Examination of Labeling with $^{89}$Zr in Stabilized Liquid Formulation Comprising DFO-Anti-Human CEACAM5 Antibody Fab Fragment Conjugate For the liquid formulation comprising PB009-2 at 10 mg/mL and having formulations described in Table 9 below, labeling efficiency with $^{89}$Zr after storage at −80° C. was evaluated.

$^{89}$Zr was produced as $^{89}$Zr-Oxalate dissolved in a 1 M aqueous oxalic acid solution at Advanced Science Research Center Okayama University, Department of Radiation Research, Shikada Laboratory. 40 μL of $^{89}$Zr-Oxalate was neutralized with 20 μL of a 2 M aqueous sodium carbonate solution, and diluted with 190 μL of ultrapure water. Subsequently, 150 μL of a PB009-2 (10 mg/mL) liquid formulation comprising Polysorbate 80 at 0.05 w/v %, sucrose at 10 w/v % or glycerin at 30 w/v % and citric acid at 20 mmol/L was added, and the mixture was reacted at room temperature for 30 minutes. The obtained reaction mixture was purified using Amicon Ultra 0.5 mL centrifugal filter (Merck Millipore) to obtain a $^{89}$Zr-labeled PB009-2 of interest. This $^{89}$Zr-DFO-anti-human CEACAM5 antibody Fab fragment conjugate is designated as PB009-3. The PB009-3 solution before and after the purification was measured by TLC (thin-layer chromatography) and the SE-HPLC method to determine the reaction rate of $^{89}$Zr. The analysis conditions are as follows.

The TLC was performed by applying a small amount of the sample to a TLC aluminum sheet (Merck KGaA, 1-05560-0001) and using a 0.1 M EDTA solution (pH: 7.0) as a developing solution. The reaction rate of $^{89}$Zr was calculated from:

(radiation amount *a* around origin)/(total radiation amount *b*)×100

[Size Exclusion Chromatography Method (SE-HPLC Method)]

In SE-HPLC measurement, G3000SWXL (TOSOH CORPORATION) was connected to a HPLC system, and a mobile phase having a composition of phosphoric acid at 20 mmol/L, sodium chloride at 150 mmol/L and 5% acetonitrile (pH 7.0) was fed at a flow rate of 0.5 mL/min. The column temperature was set to 30° C., and detection was performed at UV 280 nm and by RI.

The test results showed that both the examined formulations gave a high reaction rate value of about 90% (before purification) (Table 9), and comparison between the peak of PB009-3 observed in the UV detector and the RI detector and the peak of PB009-2 observed in the UV detector showed that the retention times of these peaks were equivalent to each other. Therefore, it was confirmed that the DFO-anti-human CEACAM5 antibody Fab fragment conjugate was labeled with $^{89}$Zr. It was shown that both the formulation with sucrose or the formulation with glycerin had little possibility of inhibiting the $^{89}$Zr labeling reaction.

TABLE 9

Reaction rate determined from TLC results

| Formulation | TLC measurement-reaction rate (%) | |
|---|---|---|
| | Before purification | After purification |
| 20 mmol/L Citric acid, pH 6.7, 10 w/v % Sucrose, 0.05 w/v % Polysorbate 80 | 87.3 | 98.9 |
| 20 mmol/L Citric acid, pH 6.7, 30 w/v % Glycerin, 0.05 w/v % Polysorbate 80 | 89.1 | 96.7 |

Experiment 1-9: Examination of Stability During Storage of Formulation Comprising DFO-Anti-Human CEACAM5 Antibody Fab Fragment Conjugate A sample F-1 shown in Table 10 was prepared by adding citric acid, sucrose and Polysorbate 80 to a liquid formulation comprising PB009-2 in such a manner that the final concentration of PB009-2 was 10 mg/mL. The pH was adjusted by adding an appropriate amount of hydrochloric acid or sodium hydroxide. The sample was aseptically filtered through a filter having a pore size of 0.22 μm, and filled in an amount of 1.2 mL into a glass vial (with a volume of 3 mL). The glass vial was stoppered with a rubber stopper, and covered and capped with an aluminum cap.

TABLE 10

| Sample No. | Buffering agent | pH | Stabilizer | Nonionic surfactant |
|---|---|---|---|---|
| F-1 | 20 mmol/L Citric acid | 6.7 | 10 w/v % Sucrose | 0.05 w/v % Polysorbate 80 |

For evaluating the stability of the liquid formulation, a storage stability test of each sample in a normally placed state was conducted. In the storage stability test, the stability of PB009-2 after storage at −20° C. or 5° C. for 1 to 6 months was evaluated on the basis of the amount of multimers measured by the SE-HPLC method. The SE-HPLC method was carried out in the same manner as in Experiment 1-4.

Table 11 shows the evaluation results obtained by the SE-HPLC method in this experiment. The results revealed that there was no problem in storage stability for at least 6 months in storage at −20° C. It was confirmed that in storage at 5° C., storage stability up to 1 month was equivalent to storage stability at −20° C. for the same period.

TABLE 11

| Sample No. | Storage temperature | Amount of multimers in SE-HPLC (%) | | | |
|---|---|---|---|---|---|
| | | At start of test | After storage for 1 month | After storage for 3 months | After storage for 6 months |
| F-1 | −20° C. | 1.4 | 2.1 | 2.3 | 3.0 |
| F-1 | 5° C. | 1.4 | 2.2 | 3.1 | 5.1 |

Experiment 2-1: Preparation of Anti-Human MUC1 Antibody Fab Fragment

Two anti-human MUC1 antibody Fab fragments designated as P10-1 Fab and P10-2 Fab were prepared. The amino acid sequences of the heavy chain variable regions and the light chain variable regions of P10-1 Fab and P10-2 Fab were specifically designed as sequences expected to improve affinity and not to attenuate affinity even by the binding of a labeling moiety, by using a molecular model of a humanized antibody constructed in accordance with the literature (Proteins, 2014 August; 82 (8): 1624-35) after humanization of a 1B2 antibody, which is a mouse-derived anti-human cancer-specific MUC1 antibody, with reference to the method described in the literature (Front Biosci., 2008 Jan. 1; 13: 1619-33).

GS vector pEE6.4 (Lonza Group AG) having an insert of a heavy chain fragment gene formed by connecting a gene encoding a signal sequence (MEWSWVFLF-FLSVTTGVHS (SEQ ID NO: 17)) to the 5' side of the heavy chain fragment gene of P10-1 Fab and P10-2 Fab (SEQ ID NO: 5 and SEQ ID NO: 7, respectively) was prepared. Also, GS vector pEE12.4 (Lonza Group AG) having an insert of a light chain gene formed by connecting a gene encoding a signal sequence (MSVPTQVLGLLLLWLTDARC (SEQ ID NO: 18)) to the 5' side of the common light chain gene (SEQ ID NO: 9) of P10-1 Fab and P10-2 Fab was prepared.

The expression of each Fab fragment was performed by the method of transient expression. Expi293F cells (Thermo Fisher Scientific Inc.) cultured into approximately 2500000 cells/mL in Expi293 Expression Medium (Thermo Fisher Scientific Inc.) were transfected with the GS vectors of the heavy chain fragment and the light chain mentioned above using ExpiFectamine 293 Transfection Kit (Thermo Fisher Scientific Inc.), and cultured for 8 days. After expression, the culture supernatant was purified using KappaSelect (GE Healthcare Japan Corp.) to obtain each Fab fragment.

The nucleotide sequence of the heavy chain fragment of P10-1 Fab is shown in SEQ ID NO: 5, and the amino acid sequence encoded thereby is shown in SEQ ID NO: 6. The nucleotide sequence of the heavy chain variable region of P10-1 Fab is shown in SEQ ID NO: 11. The amino acid sequence encoded thereby is shown in SEQ ID NO: 12.

The nucleotide sequence of the heavy chain fragment of P10-2 Fab is shown in SEQ ID NO: 7. The amino acid sequence encoded thereby is shown in SEQ ID NO: 8. The nucleotide sequence of the heavy chain variable region of P10-2 Fab is shown in SEQ ID NO: 13. The amino acid sequence encoded thereby is shown in SEQ ID NO: 14.

The light chain is common in P10-1 Fab and P10-2 Fab. The nucleotide sequence thereof is shown in SEQ ID NO: 9. The amino acid sequence encoded thereby is shown in SEQ ID NO: 10. The nucleotide sequence of the light chain variable region of P10-1 Fab and P10-2 Fab is shown in SEQ ID NO: 15. The amino acid sequence encoded thereby is shown in SEQ ID NO: 16.

As a result of analyzing the amino acid modification of purified P10-2 Fab, it was suggested that heavy chain N-terminal glutamine was modified into pyroglutamic acid in a great majority of purified antibodies.

Experiment 2-2: Labeling of Anti-Human MUC1 Antibody Fab Fragment with Chelating Agent p-SCN-Bn-DFO (DFO substituted by a p-isothiocyanophenylaminothiocarbonyl group) (Macrocyclics, Inc.) was used in the binding of chelating agent DFO to anti-human MUC1 antibody Fab fragment P10-2. To a Fab fragment solution adjusted to 12.5 mg/mL with phosphate-buffered saline (pH 7.4), a 100 mmol/L aqueous sodium carbonate solution was added at 10 mmol/L to adjust the pH to 9.0. p-SCN-Bn-DFO was added thereto at a final concentration of 1 mmol/L and reacted at 37° C. for 2 hours. Since p-SCN-Bn-DFO has an isothiocyanate group, it rapidly reacts with Lys of the Fab fragment. This was recovered through Amicon Ultra 10K-0.5 mL centrifugal filter to purify a DFO-anti-human MUC1 antibody Fab fragment conjugate bound to DFO via a linker (—C(=S)—NH-(1,4-phenylene)-NH—C(=S)—) (designated as PB010-3).

Experiment 2-3: Examination of Effect of pH on Stabilization of DFO-Anti-Human MUC1 Antibody Fab Fragment Conjugate (Effect on Multimer Generation and Insoluble Subvisible Particle Generation)

For liquid formulation comprising PB010-3, an effect of pH on stabilization of PB010-3 was evaluated. In this test, samples G-1 to G-6 shown in Table 12 were prepared by adding a buffering agent, a stabilizer and a nonionic surfactant to the liquid formulation comprising PB010-3 in such a manner that the final concentration of PB010-3 was 10 mg/mL. The pH was adjusted by adding an appropriate amount of hydrochloric acid or sodium hydroxide. Each sample was aseptically filtered through a filter having a pore size of 0.22 µm, and filled in an amount of 1.2 mL into a glass vial (with a volume of 3 mL). The glass vial was stoppered with a rubber stopper, and covered and capped with an aluminum cap.

TABLE 12

| Sample No. | Buffering agent | pH | Stabilizer | Nonionic surfactant |
|---|---|---|---|---|
| G-1 | 20 mmol/L | 6.1 | 10 w/v % | 0.05 w/v % |
| G-2 | Citric acid | 6.4 | Sucrose | Polysorbate 80 |
| G-3 | | 6.7 | | |
| G-4 | | 7.0 | | |
| G-5 | 20 mmol/L | 7.0 | | |
| G-6 | Phosphoric acid | 7.3 | | |

For evaluating the stability of the liquid formulation, a heat stability test of each sample in a normally placed state was conducted. In the heat stability test, the stability of PB010-3 after storage at 40° C. for 1 week was evaluated on the basis of the amount of multimers measured by the size exclusion chromatography method (SE-HPLC method) and the number of insoluble subvisible particles measured by the light obscuration particle count method. The analysis conditions are as follows.

[SE-HPLC Method]

In SE-HPLC measurement, BioSep SEC s3000 (Phenomenex Inc.) was connected to a HPLC system, PBS (pH 7.4) was used as a mobile phase, and fed at a flow rate of 0.5 mL/min. The injection amount of the sample was 20 µg in terms of PB010-3 (e.g. 10 µL in the case of 2 mg/mL). The column temperature was set to 30° C., the sample temperature was set to 10° C., and detection was performed at UV 280 nm.

[Light Obscuration Particle Count Method]

0.2 mL of the sample was injected into a HIAC system (Pacific Scientific Company) to perform measurement of the number of insoluble subvisible particles of 1.2 µm or more.

The area of multimers detected by the SE-HPLC method was measured by an automatic analysis method to determine the amount of multimers (%). The amount of multimers is defined in terms of a percentage (%) by measuring the area of multimer peaks detected by the SE-HPLC method using the automatic analysis method, and being divided by the sum of all peak areas including a main peak area. Here, the main peak refers to a peak of an active main body (PB010-3 which is not multimerized).

Table 13 shows the evaluation results obtained by the SE-HPLC method and the light obscuration particle count method in this experiment. The results showed that the amount of multimers in SE-HPLC (%) after storage at 40° C. for 1 week tended to increase with an increase in pH. The number of insoluble subvisible particles of 1.2 µm or more after storage at 40° C. for 1 week tended to increase with a decrease in pH. Comprehensive judgement on the above results revealed that the optimum pH of the liquid formulation comprising PB010-3 was about 6.5 to 7.0, from the viewpoint of stability.

TABLE 13

| Sample No. | Buffering agent | pH | Amount of multimers in SE-HPLC (%) | | Number of insoluble fine particles (≥1.2 µm/mL) | |
|---|---|---|---|---|---|---|
| | | | At start of test | After storage at 40° C. for 1 week | At start of test | After storage at 40° C. for 1 week |
| G-1 | 20 mmol/L | 6.1 | 0.5 | 3.4 | 718 | 74568 |
| G-2 | Citric acid | 6.4 | 0.5 | 4.1 | 4970 | 5660 |
| G-3 | | 6.7 | 0.5 | 5.0 | 1605 | 4625 |
| G-4 | | 7.0 | 0.5 | 6.1 | 1498 | 3185 |
| G-5 | 20 mmol/L | 7.0 | 0.5 | 6.3 | 1708 | 2143 |
| G-6 | Phosphoric acid | 7.3 | 0.5 | 9.1 | 920 | 2288 |

Experiment 2-4: Examination of Effects of Stabilizer and Nonionic Surfactant on Stabilization of DFO-Anti-Human MUC1 Antibody Fab Fragment Conjugate (Effects on Multimer Generation and Insoluble Subvisible Particle Generation)

For liquid formulation comprising PB010-3, effects of various stabilizers on the stability of PB010-3 were evaluated. In this examination, samples H-1 to H-4 shown in Table 14 were prepared by adding a buffering agent, a stabilizer and a nonionic surfactant to the liquid formulation comprising PB010-3 in such a manner that the final concentration of PB010-3 was 10 mg/mL. The pH was adjusted by adding an appropriate amount of hydrochloric acid or sodium hydroxide. Each sample was aseptically filtered through a filter having a pore size of 0.22 μm, and filled in an amount of 1.2 mL into a glass vial (with a volume of 3 mL). The glass vial was stoppered with a rubber stopper, and covered and capped with an aluminum cap.

TABLE 14

| Sample No. | Buffering agent | pH | Nonionic surfactant | Stabilizer |
| --- | --- | --- | --- | --- |
| H-1 | 20 mmol/L Citric acid | 6.7 | None | None |
| H-2 | | | 0.05 w/v % Polysorbate 80 | None |
| H-3 | | | 0.05 w/v % Polysorbate 80 | 10 w/v % Sucrose |
| H-4 | | | 0.05 w/v % Polysorbate 80 | 30 w/v % Glycerin |

For evaluating the stability of the liquid formulation, a storage test and a shaking test were conducted on each sample. The storage test was conducted by statically storing each sample under the conditions of 5° C. and −20° C. The shaking test was conducted by shaking the sample at 150 rpm for 24 hours. The stability of PB010-3 before and after each test was evaluated on the basis of the amount of multimers measured by the size exclusion chromatography method (SE-HPLC method) and the number of insoluble subvisible particles measured by the light obscuration particle count method. The analysis conditions are the same as in Experiment 2-3.

Tables 15 and 16 show the evaluation results obtained by the SE-HPLC method and the light obscuration particle count method in this experiment. The results showed that for a formulation without the addition of Polysorbate 80 and a formulation with the addition of sucrose or glycerin in addition to Polysorbate 80, a suppressive effect on increase in the amount of multimers was exhibited even after storage at 5° C. or −20° C. for 3 months. On the other hand, for the formulation without the addition of Polysorbate 80, the number of insoluble subvisible particles markedly increased after the shaking test. The above results showed that a formulation with the addition of sucrose or glycerin in addition to Polysorbate 80 was desirable, and further, from the viewpoint of an osmotic pressure ratio, sucrose at 10 w/v % was particularly preferable as a pharmaceutical additive for the liquid formulation comprising PB010-3.

TABLE 15

| | Amount of multimers in SE-HPLC (%) | | | | |
| --- | --- | --- | --- | --- | --- |
| Sample No. | At start of test | After storage at 5° C. for 1 month | After storage at 5° C. for 3 months | After storage at −20° C. for 1 month | After storage at −20° C. for 3 months |
| H-1 | 0.5 | 0.6 | 1.0 | 0.6 | 0.7 |
| H-2 | 0.5 | 0.7 | 1.4 | 0.9 | 1.3 |
| H-3 | 0.5 | 0.6 | 1.2 | 0.6 | 0.9 |
| H-4 | 0.5 | 0.6 | 1.1 | 0.6 | 0.8 |

TABLE 16

| Sample No. | Number of insoluble fine particles (≥1.2 μm/mL) | |
| --- | --- | --- |
| | At start of test | After shaking |
| H-1 | 1988 | 99380 |
| H-2 | 1145 | 1998 |
| H-3 | 1605 | 2335 |
| H-4 | 330 | 1045 |

Experiment 2-5: Examination of Effect of Surfactant on Stabilization of DFO-Anti-Human MUC1 Antibody Fab Fragment Conjugate (Effect on Insoluble Subvisible Particle Generation)

For liquid formulation comprising PB010-3, an effect of the surfactant on the stability of PB010-3 was evaluated. In this test, samples I-1 to I-4 shown in Table 17 were prepared by adding a buffering agent, a stabilizer and a nonionic surfactant to the liquid formulation comprising PB010-3 in such a manner that the final concentration of PB010-3 was 10 mg/mL, and adjusting the pH. The pH was adjusted by adding an appropriate amount of hydrochloric acid or sodium hydroxide. Each sample was aseptically filtered through a filter having a pore size of 0.22 μm, and filled in an amount of 1.2 mL into a glass vial (with a volume of 3 mL). The glass vial was stoppered with a rubber stopper, and covered and capped with an aluminum cap.

TABLE 17

| Sample No. | Buffering agent | pH | Stabilizer | Nonionic surfactant |
| --- | --- | --- | --- | --- |
| I-1 | 20 mmol/L Citric acid | 6.7 | 10 w/v % Sucrose | 0 w/v % Polysorbate 80 |
| I-2 | | | | 0.02 w/v % Polysorbate 80 |
| I-3 | | | | 0.05 w/v % Polysorbate 80 |
| I-4 | | | | 0.1 w/v % Polysorbate 80 |

For evaluating the stability of the liquid formulation, a shaking test and a freezing and thawing test were conducted on each sample. The shaking test was conducted by shaking the sample at 150 rpm for 24 hours. The freezing and thawing test was conducted by carrying out a total of three processes each comprising freezing the sample at −80° C. for 4 hours or more, and then thawing the sample at 5° C. for 4 hours or more. The stability of PB010-3 before and after each test was evaluated on the basis of the number of insoluble subvisible particles measured by the light obscuration particle count method. The analysis conditions are the same as in Experiment 2-3.

Table 18 shows the evaluation results obtained by the light obscuration particle count method in this experiment. The results revealed that Polysorbate 80 at a concentration of 0.02 w/v % or more had a suppressive effect on increase in the number of insoluble subvisible particles during shaking and freezing and thawing.

TABLE 18

| Sample No. | Number of insoluble fine particles (≥1.2 μm/mL) | | |
|---|---|---|---|
| | At start of test | After shaking | After freezing and thawing |
| I-1 | 12923 | 77135 | 18425 |
| I-2 | 1340 | 2615 | 1633 |
| I-3 | 1933 | 2168 | 985 |
| I-4 | 703 | 1383 | 3310 |

Experiment 2-6: Examination of Labeling with $^{89}$Zr in Stabilized Liquid Formulation Comprising DFO-Anti-Human MUC1 Antibody Fab Fragment Conjugate For the liquid formulation comprising PB010-3 at 10 mg/mL and having formulations described in Table 9 below, labeling efficiency with $^{89}$Zr after storage at −80° C. was evaluated.

$^{89}$Zr was produced as $^{89}$Zr-Oxalate dissolved in a 1 M aqueous oxalic acid solution at Advanced Science Research Center Okayama University, Department of Radiation Research, Shikada Laboratory. 40 μL of $^{89}$Zr-Oxalate was neutralized with 20 μL of a 2 M aqueous sodium carbonate solution, and diluted with 190 μL of ultrapure water. Subsequently, 150 μL of a PB010-3 (10 mg/mL) liquid formulation comprising Polysorbate 80 at 0.05 w/v %, sucrose at 10 w/v % or glycerin at 30 w/v % and citric acid at 20 mmol/L was added, and the mixture was reacted at room temperature for 60 minutes. The obtained reaction mixture was purified using Amicon Ultra 0.5 mL centrifugal filter (Merck Millipore) to obtain a $^{89}$Zr-labeled PB010-3 of interest. This $^{89}$Zr-labeled P10-2 Fab DFO (PB010-3) is designated as PB010-4. The PB010-4 solution before and after the purification was measured by TLC (thin-layer chromatography) and the SE-HPLC method to determine the reaction rate of $^{89}$Zr. The analysis conditions for the TLC and SE-HPLC method are the same as in Experiment 1-8.

The test results showed that both the examined formulations gave a high reaction rate value of about 90% (before purification) (Table 19), and comparison between the peak of PB010-4 observed in the UV detector and the RI detector and the peak of PB010-3 observed in the UV detector showed that the retention times of these peaks were equivalent to each other. Therefore, it was confirmed that PB010-3 was labeled with $^{89}$Zr. It was shown that both the examined formulations had little possibility of hampering the $^{89}$Zr labeling reaction.

TABLE 19

| | Reaction rate determined from TLC results | |
|---|---|---|
| | TLC measurement-reaction rate (%) | |
| Formulation | Before purification | After purification |
| 20 mmol/L Citric acid, pH 6.7, 10 w/v % Sucrose, 0.05 w/v % Polysorbate 80 | 91.2 | 96.5 |

TABLE 19-continued

| | Reaction rate determined from TLC results | |
|---|---|---|
| | TLC measurement-reaction rate (%) | |
| Formulation | Before purification | After purification |
| 20 mmol/L Citric acid, pH 6.7, 30 w/v % Glycerin, 0.05 w/v % Polysorbate 80 | 90.8 | 99.0 |

Experiment 2-7: Examination of Stability During Storage of Formulation Comprising DFO-Anti-Human MUC1 Antibody Fab Fragment Conjugate For liquid formulation comprising PB010-3, the stability during refrigeration and freezing storage was evaluated. In this test, a sample J-1 was prepared on the basis of Table 20 by adding a buffering agent, a stabilizer and a nonionic surfactant to the liquid formulation comprising PB010-3 in such a manner that the final concentration of PB010-3 was 10 mg/mL. The pH was adjusted by adding an appropriate amount of hydrochloric acid or sodium hydroxide. Each sample was aseptically filtered through a filter having a pore size of 0.22 μm, and filled in an amount of 1.2 mL into a glass vial (with a volume of 3 mL). The glass vial was stoppered with a rubber stopper, and covered and capped with an aluminum cap.

TABLE 20

| Sample No. | Buffering agent | pH | Stabilizer | Nonionic surfactant |
|---|---|---|---|---|
| J-1 | 20 mmol/L Citric acid | 6.7 | 10 w/v % Sucrose | 0.05 w/v % Polysorbate 80 |

For evaluating the stability of the liquid formulation, each samples was statically stored under the conditions of 5° C. and −20° C. The stability of PB010-3 after storage was evaluated on the basis of the amount of multimers measured by the SE-HPLC method, the amount of free Fab bodies (%) measured by the reversed-phase chromatography method (RP-HPLC method) and the number of insoluble subvisible particles measured by the light obscuration particle count method. The analysis conditions are as follows.

[SE-HPLC Method]

The method was carried out under the same conditions as in Experiment 2-3.

[RP-HPLC Method]

In RP-HPLC measurement, Intrada WP-RP (Imtakt Corporation) was connected to a HPLC system, and measurement was performed. 0.1% TFA and 0.1% TFA/acetonitrile were connected to a mobile phase A line and a mobile phase B line, respectively, and fed at a flow rate of 1.0 mL/min while maintaining a ratio as shown in the table below. The injection amount of the sample was 20 μg in terms of PB010-3 (e.g. 20 μL in the case of 1 mg/mL). The RP-HPLC gradient program of Table 21 was applied. The column temperature was set to 60° C., the sample temperature was set to 10° C., and detection was performed at UV 214 nm.

TABLE 21

| Time (min) | A % | B % |
|---|---|---|
| 0.0 | 76 | 24 |
| 39.0 | 63 | 37 |
| 39.1 | 0 | 100 |
| 41.5 | 0 | 100 |
| 41.6 | 76 | 24 |
| 45.0 | 76 | 24 |

The area of multimers detected by the RP-HPLC method was measured by an automatic analysis method to determine the amount of free Fab bodies (%). The amount of free Fab bodies is defined in terms of a percentage (%) by measuring the area of free Fab fragment peaks detected by the RP-HPLC method using the automatic analysis method, and being divided by the sum of all peak areas including a main peak area. In this context, the main peak refers to a peak of an active main body

[Light Obscuration Particle Count Method]

The method was carried out under the same conditions as in Experiment 2-3.

Table 22 shows the evaluation results obtained by the SE-HPLC method, the RP-HPLC method and the light obscuration particle count method in this experiment. The results revealed that there was no problem in storage stability for 3 months or less.

TABLE 22

| Sample No. | Evaluation item | At start of test | After storage at 5° C. for 1 month | After storage at 5° C. for 3 months | After storage at −20° C. for 1 month | After storage at −20° C. for 3 months |
|---|---|---|---|---|---|---|
| J-1 | Amount of multimers in SE-HPLC (%) | 0.5 | 0.6 | 1.2 | 0.6 | 0.9 |
| | Amount of free Fab bodies in RP-HPLC (%) | 6.6 | 6.4 | 6.8 | 6.4 | 6.6 |
| | Number of insoluble fine particles (≥1.2 μm/mL) | 1605 | 1775 | 3883 | 6383 | 3353 |

Experiment 3-1: Fluorescent Labeling of Anti-Human MUC1 Antibody Fab Fragment

A fluorescent dye was introduced to P10-2 Fab prepared in Experiment 2-1. Specifically, each Fab fragment solution adjusted to approximately 1 mg/mL with phosphate-buffered saline (pH 7.4) was adjusted to pH 8.5 by the addition of a 1/10 amount of a 1 M dipotassium hydrogen phosphate solution (pH 9). IRDye800CW NHS Ester (LI-COR, Inc.) was added thereto at a final concentration of 310.8 μg/mL, and the resultant was stirred at room temperature under shading for 2 hours. IRDye800CW NHS Ester has a N-hydroxysuccinimide group and therefore reacts immediately with Lys of the Fab fragment. This was recovered through Amicon Ultra 3K-0.5 mL centrifugal filter (Merck Millipore) to purify an IRDye800CW-anti-human MUC1 antibody Fab fragment conjugate (designated as PB010-2).

Experiment 3-2: Effect of pH on Stabilization of IRDye800CW-Anti-Human MUC1 Antibody Fab Fragment Conjugate For liquid formulation comprising PB010-2, an effect of pH on stabilization of PB010-2 was evaluated. In this test, the concentration of PB010-2 was 10 mg/mL, and samples K-1 to K-5 were prepared on the basis of Table 23. The pH was adjusted by adding an appropriate amount of hydrochloric acid or sodium hydroxide. Each sample was aseptically filtered through a filter having a pore size of 0.22 μm, and filled in an amount of 1.2 mL into a glass vial (with a volume of 3 mL). The glass vial was stoppered with a rubber stopper, and covered and capped with an aluminum cap.

TABLE 23

| Sample No. | Buffering agent | pH |
|---|---|---|
| K-1 | 20 mmol/L Citric acid | 6.0 |
| K-2 | | 7.0 |
| K-3 | 20 mmol/L Phosphoric acid | 6.0 |
| K-4 | | 7.0 |
| K-5 | | 8.0 |

For evaluating the stability of the liquid formulation, a heat stability test of each sample in a normally placed state was conducted. In the heat stability test, the stability of PB010-2 after storage at 40° C. for 1 week was evaluated on the basis of the amount of multimers measured by the size exclusion chromatography method (SE-HPLC method) and the number of insoluble subvisible particles measured by the microflow imaging method. The analysis conditions are as follows.

[Size Exclusion Chromatography Method (SE-HPLC Method)]

In SE-HPLC measurement, G2000SWXL (TOSOH CORPORATION) was connected to a HPLC system, and a mobile phase having a composition of phosphoric acid at 20 mmol/L and sodium chloride at 1000 mmol/L (pH 7.0) was fed at a flow rate of 0.5 mL/min. The injection amount of the sample was 50 μg in terms of PB010-2 (e.g. 10 μL in the case of 5 mg/mL). The column temperature was set to 30° C., the sample temperature was set to 5° C., and detection was performed at UV 280 nm.

The area of multimers detected by the SE-HPLC method was measured by an automatic analysis method to determine the amount of multimers (%). The amount of multimers is defined in terms of a percentage (%) by measuring the area of multimer peaks detected by the SE-HPLC method using the automatic analysis method, and being divided by the sum of all peak areas including a main peak area. In this context, the main peak refers to a peak of an active main body.

[Microflow Imaging Method]

650 μL of the sample was injected into a microflow imaging system (Protein Simple, Inc.) to perform measurement of the number of insoluble subvisible particles having a particle size of 1.2 μm or more in 1 mL of the sample.

Table 24 shows the evaluation results obtained by the SE-HPLC method and the microflow imaging method in this experiment. The results showed that the amount of multimers in SE-HPLC after storage at 40° C. for 1 week tended to increase with an increase in pH. The number of insoluble subvisible particles of 1.2 μm or more after storage at 40° C. for 1 week tended to increase with a decrease in pH. Comprehensive judgement on the above results revealed that the optimum pH was about 6.5 to 7.5.

after each test was evaluated on the basis of the amount of multimers measured by the size exclusion chromatography method (SE-HPLC method), the dye antibody ratio measured by the reversed-phase chromatography method (RP-HPLC method) and the number of insoluble subvisible particles measured by the microflow imaging method. The analysis conditions are as follows.

TABLE 24

| Sample No. | Buffering agent | pH | Amount of multimers in SE-HPLC (%) | | Number of insoluble fine particles (≥1.2 μm/mL) | |
|---|---|---|---|---|---|---|
| | | | At start of test | After storage at 40° C. for 1 week | At start of test | After storage at 40° C. for 1 week |
| K-1 | 20 mmol/L | 6.0 | 1.4 | 2.3 | 10766 | 163020 |
| K-2 | Citric acid | 7.0 | 1.3 | 3.5 | 3599 | 38886 |
| K-3 | 20 mmol/L | 6.0 | 1.3 | 1.6 | 13605 | 130887 |
| K-4 | Phosphoric acid | 7.0 | 1.3 | 4.0 | 4223 | 58559 |
| K-5 | | 8.0 | 1.5 | 9.9 | 4318 | 25668 |

Experiment 3-3: Effect of Stabilizer or Nonionic Surfactant on Stabilization of IRDye800CW-Anti-Human MUC1 Antibody Fab Fragment Conjugate For liquid formulation comprising PB010-2, effects of various stabilizers on the stability of PB010-2 were evaluated. In this test, samples L-1 to L-6 were prepared on the basis of Table 25 by adding a buffering agent and an additive to the liquid formulation comprising PB010-2 in such a manner that the final concentration of PB010-2 was 10 mg/mL. The pH was adjusted by adding an appropriate amount of hydrochloric acid or sodium hydroxide. Each sample was aseptically filtered through a filter having a pore size of 0.22 μm, and filled in an amount of 1.2 mL into a glass vial (with a volume of 3 mL). The glass vial was stoppered with a rubber stopper, and covered and capped with an aluminum cap.

TABLE 25

| Sample No. | Buffering agent | pH | Additive |
|---|---|---|---|
| L-1 | 20 mmol/L | 7.0 | None |
| L-2 | Phosphoric acid | | 140 mmol/L Arginine |
| L-3 | | | 280 mmol/L Sucrose |
| L-4 | | | 140 mmol/L Sodium chloride |
| L-5 | | | 0.1 w/v % Polysorbate 80 |
| L-6 | | | 280 mmol/L Glycerin |

For evaluating the stability of the liquid formulation, a shaking test, a freezing and thawing test, a heat stability test and a light exposure test on each sample were conducted. The shaking test was conducted by shaking the sample at 150 rpm for 24 hours. The freezing and thawing test was conducted by carrying out a total of three processes each comprising freezing the sample at −80° C. for 4 hours or more, and then thawing the sample at 5° C. for 4 hours or more. The heat stability test was conducted by storing the sample at 40° C. for 2 weeks. The light exposure test was conducted by storing the sample in a horizontally placed state, and applying light of 1000 lx for 96 hours using a white fluorescent lamp. The stability of PB010-2 before and

[Size Exclusion Chromatography Method (SE-HPLC Method)]

In SE-HPLC measurement, AdvanceBio SEC 300A (Agilent Technologies) was connected to a HPLC system, and a mobile phase having a composition of phosphoric acid at 20 mmol/L and sodium chloride at 1000 mmol/L (pH 7.0) was fed at a flow rate of 0.5 mL/min. The injection amount of the sample was 50 μg in terms of PB010-2 (e.g. 10 μL in the case of 5 mg/mL). The column temperature was set to 30° C., the sample temperature was set to 5° C., and detection was performed at UV 280 nm.

The area of multimers detected by the SE-HPLC method was measured by an automatic analysis method to determine the amount of multimers (%). The amount of multimers is defined in terms of a percentage (%) by measuring the area of multimer peaks detected by the SE-HPLC method using the automatic analysis method, and being divided by the sum of all peak areas including a main peak area. In this context, the main peak refers to a peak of an active main body.

[Reversed-Phase Chromatography Method (RP-HPLC Method)]

In RP-HPLC measurement, Intrada WP-RP (Imtakt Corporation) was connected to a HPLC system, and measurement was performed. 0.1% trifluoroacetic acid/water and 0.1% trifluoroacetic acid/acetonitrile were connected to a mobile phase A line and a mobile phase B line, respectively, and fed at a flow rate of 1.0 mL/min. The injection amount of the sample was 10 μg in terms of PB010-2 (e.g. 10 μL in the case of 1 mg/mL). The RP-HPLC gradient program of Table 26 was applied. The analysis time was 45 minutes, and detection was performed at an UV wavelength of 280 or 780 nm. The column temperature was set to 75° C., and the sample temperature was set to 5° C.

TABLE 26

| Time (min) | Mobile phase B % |
|---|---|
| 0.0 | 20 |
| 39.0 | 60 |
| 39.1 | 100 |
| 41.5 | 100 |
| 41.6 | 20 |
| 45.0 | 20 |

The total area of peaks at an UV wavelength of 780 nm and the total area of peaks at an UV wavelength of 280 nm, which peaks had been detected by the RP-HPLC method, the absorbance coefficient of PB010-1 (1.42 mL/mg·cm$^{-1}$), the molecular weight of PB010-1 (47527.43) and the molar absorbance coefficient in the PBS of IRDye800CW (240000 mL/mmol·cm$^{-1}$) were applied to the following calculation formula to determine the dye antibody ratio.

$$\text{Dye Antibody Ratio} = \frac{A780\ \text{nm} \times 1.42 \times 47527.43}{(A280\ \text{nm} - (A780\ \text{nm} \times 0.03)) \times 240000}$$ [Expression 1]

[Microflow Imaging Method]

650 μL of the sample was injected into a microflow imaging system (Protein Simple, Inc.) to perform measurement of the number of insoluble subvisible particles having a particle size of 1.0 μm or more in 1 mL of the sample.

Tables 27 to 29 show the evaluation results obtained by the SE-HPLC method, the RP-HPLC method and the microflow imaging method in this experiment. In a formulation with the addition of arginine and a formulation with the addition of sucrose, an increase in the amount of multimers after storage at 40° C. for 2 weeks tended to be suppressed. In a formulation with the addition of arginine, the dye antibody ratio decreased after storage at 40° C. for 2 weeks. Further, in a formulation with the addition of sodium chloride and a formulation without the addition of an additive, the number of insoluble subvisible particles after freezing and thawing tended to increase as compared with other formulations. Comprehensive judgement on the above results revealed that sucrose was desirable as a stabilizer and a tonicity agent for the liquid formulation comprising PB010-2.

TABLE 27

| | | Amount of multimers in SE-HPLC (%) | | | | |
|---|---|---|---|---|---|---|
| Sample No. | Additive | At start of test | After shaking | After freezing and thawing | After storage at 40° C. for 2 weeks | After light exposure |
| L-1 | None | 1.9 | 2.2 | 2.5 | 9.3 | 3.8 |
| L-2 | 140 mmo/L Arginine | 1.9 | 2.4 | 2.0 | 6.2 | 3.5 |
| L-3 | 280 mmol/L Sucrose | 1.8 | 2.1 | 1.9 | 7.9 | 3.2 |
| L-4 | 140 mmol/L Sodium chloride | 1.9 | 2.3 | 2.1 | 9.6 | 3.7 |
| L-5 | 0.1 w/v % Polysorbate 80 | 2.1 | 2.4 | 2.4 | 9.4 | 3.8 |
| L-6 | 280 mmol/L Glycerin | 1.9 | 2.2 | 1.9 | 9.0 | 3.6 |

TABLE 28

| | | Dye Antibody Ratio | | | | |
|---|---|---|---|---|---|---|
| Sample No. | Additive | At start of test | After shaking | After freezing and thawing | After storage at 40° C. for 2 weeks | After light exposure |
| L-1 | None | 2.4 | 2.4 | 2.4 | 1.9 | 2.3 |
| L-2 | 140 mmol/L Arginine | 2.4 | 2.2 | 2.4 | 0.3 | 1.8 |
| L-3 | 280 mmol/L Sucrose | 2.4 | 2.4 | 2.4 | 1.8 | 2.2 |
| L-4 | 140 mmol/L Sodium chloride | 2.5 | 2.4 | 2.4 | 1.8 | 2.3 |
| L-5 | 0.1 w/v % Polysorbate 80 | 2.4 | 2.4 | 2.5 | 1.9 | 2.3 |
| L-6 | 280 mmol/L Glycerin | 2.4 | 2.4 | 2.4 | 1.9 | 2.2 |

TABLE 29

| | | Number of insoluble fine particles (≥1.0 μm/mL) | | | | |
|---|---|---|---|---|---|---|
| Sample No. | Additive | At start of test | After shaking | After freezing and thawing | After storage at 40° C. for 2 weeks | After light exposure |
| L-1 | None | 1895 | 16242 | 30603 | 12393 | 3625 |
| L-2 | 140 mmol/L Arginine | 1763 | 2587 | 13173 | 8473 | 3592 |
| L-3 | 280 mmol/L Sucrose | 2868 | 7700 | 8052 | 8396 | 5246 |
| L-4 | 140 mmol/L Sodium chloride | 2188 | 4518 | 74934 | 2785 | 2498 |
| L-5 | 0.1 w/v % Polysorbate 80 | 1486 | 4679 | 11087 | 5281 | 3813 |

TABLE 29-continued

| Sample No. | Additive | Number of insoluble fine particles (≥1.0 μm/mL) | | | | |
|---|---|---|---|---|---|---|
| | | At start of test | After shaking | After freezing and thawing | After storage at 40° C. for 2 weeks | After light exposure |
| L-6 | 280 mmol/L Glycerin | 2354 | 12898 | 13639 | 7941 | 3630 |

Experiment 3-4: Selection of Optimum pH for Stabilizing IRDye800CW-Anti-Human MUC1 Antibody Fab Fragment Conjugate For formulations in which citric acid at 20 mmol/L or phosphoric acid at 20 mmol/L is used as a buffering agent in a liquid formulation comprising PB010-2 (sample Nos. M-1 to M-10), samples were prepared at a pH of 6.6 to 7.4. In the sample, the final concentration of PB010-2 was 10 mg/mL, and if necessary, hydrochloric acid and/or sodium hydroxide were added as a pH adjuster during preparation of the buffering agent so that a predetermined pH was obtained. Each sample was aseptically filtered through a filter having a pore size of 0.22 μm, and filled in an amount of 1.2 mL into a glass vial (with a volume of 3 mL). The glass vial was stoppered with a rubber stopper, and covered and capped with an aluminum cap. The stability of each sample after the shaking test, the freezing and thawing test, the heat stability test and the light exposure test was evaluated on the basis of the amount of multimers measured by the SE-HPLC method and the dye antibody ratio measured by RP-HPLC. The SE-HPLC method and the RP-HPLC method were carried out in the same manner as in Experiment 3-3.

Tables 30 and 31 show the results.

In terms of the amount of multimers and the dye antibody ratio, the stability was enhanced as the pH decreased (at a high pH, the stability declined due to heat and light stress). On the other hand, it was found that a pH of 6.8 was particularly preferable because the risk of subvisible particle generation due to a decrease in solubility increased as the pH became closer to 6.0.

TABLE 30

| Sample No. | Buffering agent | pH | Amount of multimers in SE-HPLC (%) | | | | |
|---|---|---|---|---|---|---|---|
| | | | At start of test | After shaking | After freezing and thawing | After storage at 40° C. for 1 week | After light exposure |
| M-1 | 20 mmol/L | 6.6 | 1.8 | 2.0 | 1.2 | 2.9 | 2.2 |
| M-2 | Citric acid | 6.8 | 1.7 | 2.0 | 1.2 | 3.1 | 2.4 |
| M-3 | | 7.0 | 1.9 | 1.9 | 1.2 | 3.6 | 2.4 |
| M-4 | | 7.2 | 1.7 | 1.9 | 1.2 | 4.0 | 2.6 |
| M-5 | | 7.4 | 1.7 | 1.9 | 1.2 | 4.5 | 2.7 |
| M-6 | 20 mmol/L | 6.6 | 1.8 | 2.1 | 1.3 | 3.4 | 2.6 |
| M-7 | Phosphoric acid | 6.8 | 1.8 | 2.0 | 1.3 | 3.8 | 2.7 |
| M-8 | | 7.0 | 1.8 | 2.0 | 1.5 | 4.1 | 2.7 |
| M-9 | | 7.2 | 1.7 | 1.9 | 1.5 | 4.5 | 2.8 |
| M-10 | | 7.4 | 1.8 | 2.0 | 1.4 | 5.4 | 3.1 |

TABLE 31

| Sample No. | Buffering agent | pH | Dye Antibody Ratio | | | | |
|---|---|---|---|---|---|---|---|
| | | | At start of test | After shaking | After freezing and thawing | After storage at 40° C. for 1 week | After light exposure |
| M-1 | 20 mmol/L | 6.6 | 1.48 | 1.48 | 1.48 | 1.32 | 1.36 |
| M-2 | Citric acid | 6.8 | 1.49 | 1.48 | 1.49 | 1.30 | 1.36 |
| M-3 | | 7.0 | 1.49 | 1.48 | 1.49 | 1.26 | 1.35 |
| M-4 | | 7.2 | 1.49 | 1.47 | 1.48 | 1.23 | 1.34 |
| M-5 | | 7.4 | 1.49 | 1.47 | 1.48 | 1.19 | 1.33 |
| M-6 | 20 mmol/L | 6.6 | 1.50 | 1.50 | 1.49 | 1.34 | 1.39 |
| M-7 | Phosphoric acid | 6.8 | 1.50 | 1.49 | 1.50 | 1.31 | 1.38 |
| M-8 | | 7.0 | 1.51 | 1.50 | 1.49 | 1.27 | 1.37 |
| M-9 | | 7.2 | 1.51 | 1.49 | 1.49 | 1.24 | 1.35 |

Experiment 3-5: Effects of Buffering Agent and Surfactant on Stabilization of IRDYE800CW-Anti-Human MUC1 Antibody Fab Fragment Conjugate For formulations with the inclusion of PB010-2 and with the addition of citric acid at 20 mmol/L (pH 6.8) or phosphoric acid at 20 mmol/L (pH 6.8) and sucrose at 280 mmol/L, samples with the addition of Polysorbate 80 at 0.05 w/v % as a surfactant and samples without the addition of Polysorbate 80 (sample Nos. N-1 to N-4) were prepared. The final concentration of PB010-2 was 10 mg/mL. After being prepared in accordance with the formulations and compositions, the samples were each aseptically filtered through a filter having a pore size of 0.22 μm, and filled in an amount of 1.2 mL into a glass vial (with a volume of 3 mL). The glass vial was stoppered with a rubber stopper, and covered and capped with an aluminum cap. If necessary, hydrochloric acid and/or sodium hydroxide were added as a pH adjuster during preparation of the buffering agent so that a predetermined pH was obtained.

The sample was stored at −20° C. or 5° C. for 1 month, and the heat stability test was conducted by storing the sample in a normally placed state at 40° C. for 2 weeks or at 25° C. for 1 month. The light exposure test was conducted by storing the sample in a horizontally placed state, and applying light of 1000 lx for 96 hours using a white fluorescent lamp. The stability of PB010-2 before and after each test was evaluated on the basis of the amount of multimers measured by the SE-HPLC method, the number of insoluble subvisible particles measured by the microflow imaging method, the fluorescence intensity measured by the SE-HPLC method and the antigen binding activity measured by the enzyme-linked immunosorbent assay (ELISA) method. The SE-HPLC method and the microflow imaging method were carried out in accordance with the methods in Experiment 3-3. The fluorescence intensity was evaluated by applying the fluorescence intensity at the detected main peak to the following formula.

$$\text{Fluorescence intensity} = \frac{\text{Main peak fluorescence}(Ex773/Em792) \text{ intensity}}{(A280 \text{ nm} - (A780 \text{ nm} \times 0.03))} \quad [\text{Expression 2}]$$

[ELISA Method]

A phosphate buffer solution containing hMUC-1 (PEPTIDE INSTITUTE, INC.) antigen at 0.8 nM was added to an assay plate, and treated at 2 to 8° C. for 18 hours, and the antigen was then immobilized using tris-buffered saline (TBS) containing 20% Blocking One (nacalai tesque) and Tween-20 at 0.05 w/v %. The PB010-2 solution was step-wise diluted with TBS containing 5% Blocking One and Tween-20 at 0.05 w/v % over a concentration range of 0 to 100000 ng/mL, and added onto the plate having the immobilized antigen. The plate was incubated at 25° C. for 60 minutes, and goat anti-human Kappa-HRP (Southern Biotech, Inc.) diluted to 4000 times was then added to the plate. The plate was incubated at 25° C. for 60 minutes, and then washed three times. 100 μL of TMB+Substrate-Chromogen (Dako) was added to the plate, incubation was then performed at 25° C. for 20 minutes, and sulfuric acid at 1 mol/L was added to stop the reaction. Thereafter, using Spectra Max 190 (Molecular Devices, LLC), an UV absorption at 450 nm was examined to evaluate the binding activity. The binding activity was calculated as a binding activity relative to the activity of PB010-2, which is defined as 100%.

Tables 32 to 35 show the results.

It was found that use of Polysorbate 80 at 0.05 w/v % as a nonionic surfactant was particularly preferable because in formulations with the addition of Polysorbate 80, an increase in the amount of insoluble subvisible particles after the heat stability test and the light exposure test was suppressed. It was found that use of citric acid as a buffering agent was particularly preferable because in formulations with the addition of citric acid, the increasing tendency in the amount of multimers after storage at 40° C. was smaller as compared with formulations with the addition of phosphoric acid. In any of the formulations and storage conditions, there was no decrease in antigen binding activity or the fluorescence intensity.

TABLE 32

| Sample No. | Buffering agent | pH | Stabilizer | Nonionic surfactant | At start of test | Amount of multimers in SE-HPLC (%) | | |
| --- | --- | --- | --- | --- | --- | --- | --- | --- |
| | | | | | | After storage at 40° C. for 2 weeks | After storage at 25° C. for 1 month | After light exposure |
| N-1 | 20 mmol/L Citric acid | 6.8 | 280 mmol/L Sucrose | 0 w/v % Polysorbate 80 | 2.1 | 5.6 | 3.6 | 34 |
| N-2 | | | | 0.05 w/v % Polysorbate 80 | 2.1 | 5.7 | 3.8 | 3.5 |
| N-3 | 20 mmol/L Phosphoric acid | | | 0 w/v % Polysorbate 80 | 2.1 | 6.6 | 4.1 | 3.8 |
| N-4 | | | | 0.05 w/v % Polysorbate 80 | 2.2 | 6.7 | 4.3 | 3.9 |

TABLE 33

| Sample No. | Buffering agent | pH | Stabilizer | Nonionic surfactant | At start of test | Number of insoluble fine particles (≥1.0 μm/mL) | | |
| --- | --- | --- | --- | --- | --- | --- | --- | --- |
| | | | | | | After storage at 40° C. for 2 weeks | After storage at 25° C. for 1 month | After light exposure |
| N-1 | 20 mmol/L Citric acid | 6.8 | 280 mmol/L Sucrose | 0 w/v % Polysorbate 80 | 1318 | 30588 | 38922 | 54915 |

TABLE 33-continued

| Sample No. | Buffering agent | pH | Stabilizer | Nonionic surfactant | At start of test | After storage at 40° C. for 2 weeks | After storage at 25° C. for 1 month | After light exposure |
|---|---|---|---|---|---|---|---|---|
| | | | | | | Number of insoluble fine particles (≥1.0 μm/mL) | | |
| N-2 | | | | 0.05 w/v % Polysorbate 80 | 3737 | 11258 | 7085 | 4850 |
| N-3 | 20 mmol/L Phosphoric acid | | | 0 w/v % Polysorbate 80 | 7532 | 31998 | 37638 | 32926 |
| N-4 | | | | 0.05 w/v % Polysorbate 80 | 5228 | 7911 | 14801 | 7486 |

TABLE 34

| Sample No. | Buffering agent | pH | Stabilizer | Nonionic surfactant | At start of test | After storage at 40° C. for 2 weeks | After storage at 25° C. for 1 month | After light exposure |
|---|---|---|---|---|---|---|---|---|
| | | | | | | Fluorescence intensity | | |
| N-1 | 20 mmol/L Citric acid | 6.8 | 280 mmol/L Sucrose | 0 w/v % Polysorbate 80 | 0.0526 | 0.0540 | 0.0558 | 0.0521 |
| N-2 | | | | 0.05 w/v % Polysorbate 80 | 0.0539 | 0.0530 | 0.0546 | 0.0551 |
| N-3 | 20 mmol/L Phosphoric acid | | | 0 w/v % Polysorbate 80 | 0.0536 | 0.0540 | 0.0551 | 0.0537 |
| N-4 | | | | 0.05 w/v % Polysorbate 80 | 0.0528 | 0.0532 | 0.0546 | 0.0548 |

TABLE 35

| Sample No. | Buffering agent | pH | Stabilizer | Nonionic surfactant | At start of test | After light exposure | After storage at −20° C. for 1 month | After storage at 5° C. for 1 month | After storage at 25° C. for 1 month |
|---|---|---|---|---|---|---|---|---|---|
| | | | | | | Antibody binding activity (%) | | | |
| N-1 | 20 mmol/L Citric acid | 6.8 | 280 mmol/L Sucrose | 0 w/v % Polysorbate 80 | 117.29 | 99.94 | 93.37 | 100.00 | 113.16 |
| N-2 | | | | 0.05 w/v % Polysorbate 80 | 99.00 | 91.59 | 93.61 | 104.03 | 104.86 |
| N-3 | 20 mmol/L Phosphoric acid | | | 0 w/v % Polysorbate 80 | 99.24 | 96.52 | 109.16 | 99.43 | 122.22 |
| N-4 | | | | 0.05 w/v % Polysorbate 80 | 99.59 | 85.06 | 108.81 | 92.74 | 105.92 |

Experiment 3-6. Examination of Stability During Storage of Formulation Comprising IRDye800CW-Anti-Human MUC1 Antibody Fab Fragment Conjugate A sample with a formulation shown in Table 36 was prepared by adding PB010-2 at a concentration of 10 mg/mL, sucrose at a concentration of 280 mmol/L and Polysorbate 80 at a concentration of 0.05 w/v % to a formulated solution adjusted to a pH of 6.8 using citric acid at 20 mmol/L, and the sample was aseptically filtered through a filter having a pore size of 0.22 μm, and filled in an amount of 1.2 mL into a glass vial (with a volume of 3 mL), and lyophilized. The glass vial was stoppered with a rubber stopper, and covered and capped with an aluminum cap. Thereafter, the stability of PB010-2 after the heat stability test or the light exposure test was evaluated.

TABLE 36

| Sample No. | Buffering agent | pH | Stabilizer | Nonionic surfactant |
|---|---|---|---|---|
| O-1 (lyophilized product) | 20 mmol/L Citric acid | 6.8 | 280 mmol/L Sucrose | 0.05 w/v % Polysorbate 80 |

The heat stability test was conducted by storing the sample in a normally placed state at 40° C. for 2 weeks. The light exposure test was conducted by storing the sample in a horizontally placed state, and applying light of 1000 lx for 96 hours using a white fluorescent lamp. The stability of PB010-2 before and after each test was evaluated on the basis of the amount of multimers and the fluorescence intensity measured by the SE-HPLC method and the dye antibody ratio measured by the RP-HPLC method. The SE-HPLC method and the RP-HPLC method were carried out in accordance with Experiment 3-3. The evaluation of the fluorescence intensity was performed in the same manner as in Experiment 3-5.

Tables 37 to 39 show the results. The above-described formulations were shown to ensure that PB010-2 is kept stable either after storage at 40° C. for 2 weeks or after light exposure.

TABLE 37

| Sample No. | Buffering agent | pH | Stabilizer | Nonionic surfactant | Amount of multimers in SE-HPLC (%) | | |
|---|---|---|---|---|---|---|---|
| | | | | | At start of test | After storage at 40° C. for 2 weeks | After light exposure |
| O-1 | 20 mmol/L Citric acid | 6.8 | 280 mmol/L Sucrose | 0.05 w/v % Polysorbate 80 | 2.0 | 2.1 | 2.2 |

TABLE 38

| Sample No. | Buffering agent | pH | Stabilizer | Nonionic surfactant | Dye Antibody Ratio | | |
|---|---|---|---|---|---|---|---|
| | | | | | At start of test | After storage at 40° C. for 2 weeks | After light exposure |
| O-1 | 20 mmol/L Citric acid | 6.8 | 280 mmol/L Sucrose | 0.05 w/v % Polysorbate 80 | 1.46 | 1.46 | 1.45 |

TABLE 39

| Sample No. | Buffering agent | pH | Stabilizer | Nonionic surfactant | Fluorescence intensity | | |
|---|---|---|---|---|---|---|---|
| | | | | | At start of test | After storage at 40° C. for 2 weeks | After light exposure |
| O-1 | 20 mmol/L Citric acid | 6.8 | 280 mmol/L Sucrose | 0.05 w/v % Polysorbate 80 | 0.0548 | 0.0573 | 0.0558 |

SEQUENCE LISTING FREE TEXT

SEQ ID NO: 1: Nucleotide sequence of DNA encoding a PB009-1 Fab heavy chain fragment
SEQ ID NO: 2: Amino acid sequence of PB009-1 Fab heavy chain fragment
SEQ ID NO: 3: Nucleotide sequence of DNA encoding a PB009-1 Fab light chain
SEQ ID NO: 4: Amino acid sequence of PB009-1 Fab light chain
SEQ ID NO: 5: Nucleotide sequence of DNA encoding a P10-1 Fab heavy chain fragment
SEQ ID NO: 6: Amino acid sequence of the P10-1 Fab heavy chain fragment
SEQ ID NO: 7: Nucleotide sequence of DNA encoding a P10-2 Fab heavy chain fragment
SEQ ID NO: 8: Amino acid sequence of the P10-2 Fab heavy chain fragment
SEQ ID NO: 9: Nucleotide sequence of DNA encoding P10-1 Fab and P10-2 Fab light chain
SEQ ID NO: 10: Amino acid sequence of P10-1 Fab and P10-2 Fab light chain
SEQ ID NO: 11: Nucleotide sequence of DNA encoding P10-1 Fab heavy chain variable region
SEQ ID NO: 12: Amino acid sequence of P10-1 Fab heavy chain variable region SEQ ID NO: 13: Nucleotide sequence of DNA encoding P10-2 Fab heavy chain variable region
SEQ ID NO: 14: Amino acid sequence of P10-2 Fab heavy chain variable region
SEQ ID NO: 15: Nucleotide sequence of DNA encoding P10-1 Fab and P10-2 Fab light chain variable region
SEQ ID NO: 16: Amino acid sequence of P10-1 Fab and P10-2 Fab light chain variable region
SEQ ID NO: 17: Heavy chain signal sequence for PB009-1 Fab, P10-1 Fab and P10-2 Fab
SEQ ID NO: 18: Light chain signal sequence for PB009-1 Fab, P10-1 Fab and P10-2 Fab
SEQ ID NO: 19: Tandem repeat sequence of the extracellular domain of MUC1

The invention claimed is:

1. A pharmaceutical composition comprising a labeling moiety-anti-human antibody Fab fragment conjugate, a buffering agent, a stabilizer and a nonionic surfactant and having a pH of 6.7, wherein
the anti-human antibody Fab fragment is one or more selected from the group consisting of the following (a) and (b):
(a) an anti-human CEACAM5 antibody Fab fragment comprising a heavy chain fragment consisting of the amino acid sequence represented by SEQ ID NO: 2 and a light chain consisting of the amino acid sequence represented by SEQ ID NO: 4; and
(b) an anti-human CEACAM5 antibody Fab fragment comprising a heavy chain fragment derived from a heavy chain fragment consisting of the amino acid sequence represented by SEQ ID NO: 2 by the modification of glutamic acid at amino acid position 1 of SEQ ID NO: 2 into pyroglutamic acid, and a light chain consisting of the amino acid sequence represented by SEQ ID NO: 4, and
the labeling moiety is a group represented by the following formula (I):

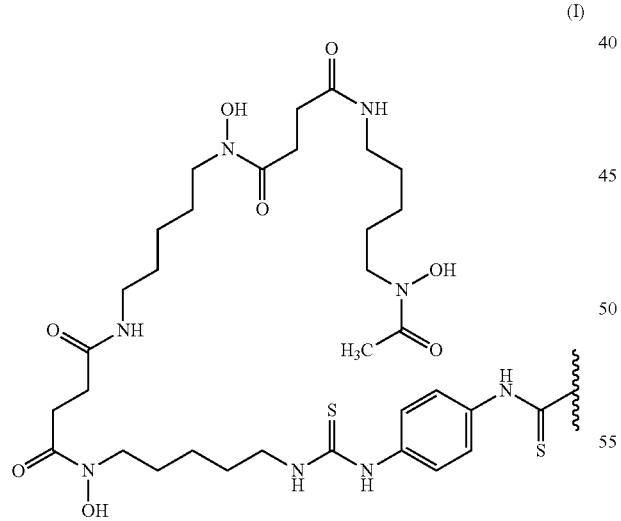

wherein the wavy line represents binding to the anti-human CEACAM5 antibody Fab fragment, where the anti-human CEACAM5 antibody Fab fragment is bound to the carbon atom of a labeling moiety terminal C(=S) group via an amino group in the anti-human CEACAM5 antibody Fab fragment,
the concentration of the labeling moiety-anti-human antibody Fab fragment conjugate is 10 mg/mL,
the nonionic surfactant comprises Polysorbate 80,
the concentration of the nonionic surfactant is 0.05 w/v %,
the buffering agent comprises citric acid,
the concentration of the buffering agent is 20 mmol/L,
the stabilizer comprises sucrose or glycerin, and
the concentration of the stabilizer is 10 to 30 w/v %.

2. A pharmaceutical composition comprising a labeling moiety-anti-human antibody Fab fragment conjugate, a buffering agent, a stabilizer and a nonionic surfactant and having a pH of 6.7, wherein
the anti-human antibody Fab fragment is one or more selected from the group consisting of the following (a) and (b):
(a) an anti-human MUC1 antibody Fab fragment comprising a heavy chain fragment consisting of the amino acid sequence represented by SEQ ID NO: 6 or SEQ ID NO: 8 and a light chain consisting of the amino acid sequence represented by SEQ ID NO: 10; and
(b) an anti-human MUC1 antibody Fab fragment comprising a heavy chain fragment derived from a heavy chain fragment consisting of the amino acid sequence represented by SEQ ID NO: 6 or SEQ ID NO: 8 by the modification of glutamine at amino acid position 1 of SEQ ID NO: 6 or SEQ ID NO: 8 into pyroglutamic acid, and a light chain consisting of the amino acid sequence represented by SEQ ID NO: 10, and
the labeling moiety is a group represented by the following formula (I):

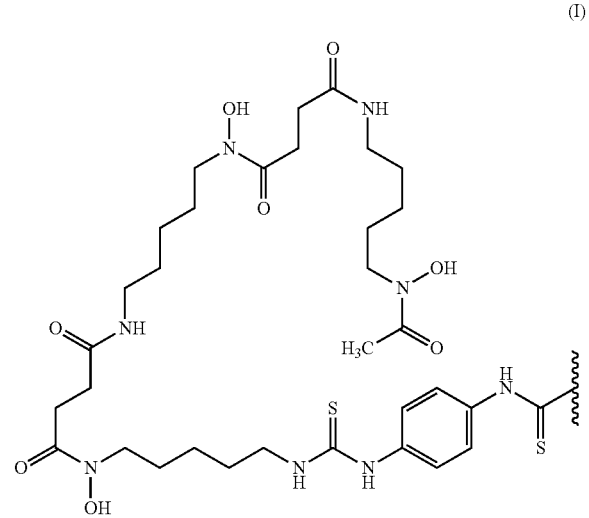 [SMILES: *C(=S)Nc1ccc(NC(=S)NCCCCCN(O)C(=O)CCC(=O)NCCCCCN(O)C(=O)CCC(=O)NCCCCCN(O)C(C)=O)cc1]

wherein the wavy line represents binding to the anti-human MUC1 antibody Fab fragment, where the anti-human MUC1 antibody Fab fragment is bound to the carbon atom of a labeling moiety terminal C(=S) group via an amino group in the anti-human MUC1 antibody Fab fragment, the concentration of the labeling moiety-anti-human antibody Fab fragment conjugate is 10 mg/mL, the nonionic surfactant comprises Polysorbate 80, the concentration of the nonionic surfactant is 0.05 w/v %, the buffering agent comprises citric acid, the concentration of the buffering agent is 20 mmol/L, the stabilizer comprises sucrose or glycerin, and the concentration of the stabilizer is 10 to 30 w/v %.

3. The pharmaceutical composition according to claim 1, wherein the labeling moiety-anti-human antibody Fab fragment conjugate further comprises $^{89}$Zr.

4. A method of diagnosing colorectal cancer or cancer resulting from the metastasis of colorectal cancer, the method comprising administering to a subject the pharmaceutical composition according to claim 3 and detecting the labeling moiety-anti-human antibody Fab fragment conjugate.

5. A method of diagnosing breast cancer or cancer resulting from the metastasis of breast cancer, the method comprising administering to a subject the pharmaceutical composition according to claim 3 and detecting the labeling moiety-anti-human antibody Fab fragment conjugate.

6. The pharmaceutical composition according to claim 1 or claim 2, which is a liquid formulation, a frozen formulation or a lyophilized formulation.

7. A method for producing the pharmaceutical composition according to claim 1 or claim 2, comprising the steps of:
(a) producing and adding the labeling moiety-anti-human antibody Fab fragment conjugate at 10 mg/ml;
(b) adding citric acid at 20 mmol/L as a buffering agent;
(c) adding sucrose or glycerin at 10 to 30 w/v % as a stabilizer;
(d) adding Polysorbate 80 at 0.05 w/v % as a nonionic surfactant; and
(e) adjusting the pH to 6.7.

8. A method for stably preserving a labeling moiety-anti-human antibody Fab fragment conjugate contained in the pharmaceutical composition according to claim 1 or claim 2, comprising the steps of:
(a) adding citric acid at 20 mmol/L as a buffering agent to a solution containing the labeling moiety-anti-human antibody Fab fragment conjugate at 10 mg/mL;
(b) adding sucrose or glycerin at 10 to 30 w/v % as a stabilizer to the solution containing the labeling moiety-anti-human antibody Fab fragment conjugate;
(c) adding Polysorbate 80 at 0.05 w/v % as a nonionic surfactant to the solution containing the labeling moiety-anti-human antibody Fab fragment conjugate; and
(d) adjusting the pH of the solution containing the labeling moiety-anti-human antibody Fab fragment conjugate to 6.7.

9. The pharmaceutical composition according to claim 1 or claim 2, wherein the stabilizer is sucrose.

10. The pharmaceutical composition according to claim 1, wherein
the stabilizer is sucrose, and
the concentration of the stabilizer is 10 w/v %.

11. The pharmaceutical composition according to claim 1 or claim 2, wherein the stabilizer is glycerin.

12. The pharmaceutical composition according to claim 1, wherein
the stabilizer is glycerin, and
the concentration of the stabilizer is 30 w/v %.

13. The pharmaceutical composition according to claim 2, wherein
the stabilizer is sucrose, and
the concentration of the stabilizer is 10 w/v %.

14. The pharmaceutical composition according to claim 2, wherein
the stabilizer is glycerin, and
the concentration of the stabilizer is 30 w/v %.

* * * * *